United States Patent
Luo et al.

(10) Patent No.: US 11,078,528 B2
(45) Date of Patent: Aug. 3, 2021

(54) IN SITU DETECTION OF NUCLEOTIDE VARIANTS IN HIGH NOISE SAMPLES, AND COMPOSITIONS AND METHODS RELATED THERETO

(71) Applicant: Advanced Cell Diagnostics, Inc., Newark, CA (US)

(72) Inventors: Yuling Luo, San Ramon, CA (US); Xingyong Wu, Pleasanton, CA (US); Liuliu Pan, Fremont, CA (US); Xiaoming Wang, Union City, CA (US); Xiao-Jun Ma, Pleasanton, CA (US); Nan Su, San Ramon, CA (US); Steve Chen, Fremont, CA (US)

(73) Assignee: ADVANCED CELL DIAGNOSTICS, INC., Newark, CA (US)

( * ) Notice: Subject to any disclaimer, the term of this patent is extended or adjusted under 35 U.S.C. 154(b) by 128 days.

(21) Appl. No.: 15/291,054

(22) Filed: Oct. 11, 2016

(65) Prior Publication Data

US 2017/0101672 A1    Apr. 13, 2017

Related U.S. Application Data

(60) Provisional application No. 62/240,347, filed on Oct. 12, 2015.

(51) Int. Cl.
*C12Q 1/68* (2018.01)
*C12Q 1/6841* (2018.01)
(Continued)

(52) U.S. Cl.
CPC ........... *C12Q 1/6841* (2013.01); *C12Q 1/682* (2013.01); *C12Q 1/6827* (2013.01)

(58) Field of Classification Search
None
See application file for complete search history.

(56) References Cited

U.S. PATENT DOCUMENTS 3,817,837 A    6/1974   Rubenstein et al.
3,850,752 A    11/1974  Schuurs et al.
(Continued)

FOREIGN PATENT DOCUMENTS

EP    0795610        9/1997
EP    1428892 B1    11/2006
(Continued)

OTHER PUBLICATIONS

"List of sequenced bacterial genomes", Wikipedia.com; accessed Jan. 24, 2014. (Year: 2014).*

(Continued)

*Primary Examiner* — Bradley L. Sisson
(74) *Attorney, Agent, or Firm* — Casimir Jones, S.C.; Anne Reynolds

(57) ABSTRACT

The invention relates to methods of in situ detection of a nucleic acid variation of a target nucleic acid in a sample, including single nucleotide variations, multi-nucleotide variations or splice sites. The method can comprise the steps of contacting the sample with a probe that detects the nucleic acid variation or splice site and a neighbor probe; contacting the sample with pre-amplifiers that bind to the nucleic acid variation probe or splice site probe and neighbor probe, respectively; contacting the sample with a collaboration amplifier that binds to the pre-amplifiers; and contacting the sample with a label probe system, wherein hybridization of the components forms a signal generating complex (SGC) comprising a target nucleic acid with the nucleic acid variation or splice site, the probes and amplifiers; and detecting in situ signal from the SGC on the sample. The invention also provides samples, tissue slides, and kits relating to detection of nucleic acid variations, including
(Continued)

single nucleotide variations, multi-nucleotide variations or splice sites, of a target nucleic acid.

21 Claims, 21 Drawing Sheets

Specification includes a Sequence Listing.

(51) Int. Cl.
*C12Q 1/682* (2018.01)
*C12Q 1/6827* (2018.01)

(56) References Cited

U.S. PATENT DOCUMENTS

| | | |
|---|---|---|
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,853,150 A | 8/1989 | Bezborodov et al. |
| 4,868,105 A | 9/1989 | Urdea et al. |
| 4,888,278 A | 12/1989 | Singer et al. |
| 5,089,499 A | 2/1992 | Baker et al. |
| 5,093,232 A | 3/1992 | Urdea et al. |
| 5,122,599 A | 6/1992 | Barnett et al. |
| 5,124,246 A | 6/1992 | Urdea et al. |
| 5,185,244 A | 2/1993 | Wallace |
| 5,198,149 A | 3/1993 | Gray et al. |
| 5,198,357 A | 3/1993 | Holmovist et al. |
| 5,273,680 A | 12/1993 | Gray et al. |
| 5,328,637 A | 7/1994 | Buchechker et al. |
| 5,334,499 A | 8/1994 | Burdick et al. |
| 5,340,898 A | 8/1994 | Cavezzan et al. |
| 5,374,524 A | 12/1994 | Miller |
| 5,393,672 A | 2/1995 | Ness et al. |
| 5,417,885 A | 5/1995 | Suzuki et al. |
| 5,494,794 A * | 2/1996 | Wallace ............. C12Q 1/6883 435/6.16 |
| 5,523,204 A | 6/1996 | Singer et al. |
| 5,543,075 A | 8/1996 | Parri et al. |
| 5,543,305 A | 8/1996 | Cummins et al. |
| 5,550,236 A | 8/1996 | Schlosser et al. |
| 5,571,670 A | 11/1996 | Urdea et al. |
| 5,614,362 A | 3/1997 | Urdea et al. |
| 5,616,582 A | 4/1997 | Baker |
| 5,624,802 A | 4/1997 | Urdea et al. |
| 5,633,134 A | 5/1997 | Shuber |
| 5,635,352 A | 6/1997 | Urdea et al. |
| 5,641,675 A | 6/1997 | Singer et al. |
| 5,643,715 A | 7/1997 | Lancaster et al. |
| 5,643,893 A | 7/1997 | Benson et al. |
| 5,681,697 A | 10/1997 | Urdea et al. |
| 5,681,702 A | 10/1997 | Collins et al. |
| 5,681,943 A * | 10/1997 | Letsinger ............. C07H 21/00 536/24.5 |
| 5,683,623 A | 11/1997 | Chan et al. |
| 5,693,688 A | 12/1997 | Priou |
| 5,710,264 A | 1/1998 | Urdea et al. |
| 5,728,527 A | 3/1998 | Singer et al. |
| 5,747,244 A | 5/1998 | Sheridan et al. |
| 5,780,227 A | 7/1998 | Sheridan et al. |
| 5,800,733 A | 9/1998 | Kelly |
| 5,804,684 A | 9/1998 | Su |
| 5,814,448 A | 9/1998 | Silverstein et al. |
| 5,827,660 A | 10/1998 | Singer et al. |
| 5,847,149 A | 12/1998 | Fuss et al. |
| 5,849,481 A | 12/1998 | Urdea et al. |
| 5,849,958 A | 12/1998 | Barnes et al. |
| 5,866,331 A | 2/1999 | Singer et al. |
| 5,888,778 A | 3/1999 | Shuber |
| 5,892,131 A | 4/1999 | Barnes et al. |
| 5,945,515 A | 8/1999 | Chomczynski |
| 5,962,332 A | 10/1999 | Singer et al. |
| 5,985,549 A | 11/1999 | Singer et al. |
| 5,998,673 A | 12/1999 | Barnes et al. |
| 6,001,983 A | 12/1999 | Benner |
| 6,007,994 A | 12/1999 | Ward et al. |
| 6,037,120 A | 3/2000 | Benner |
| 6,057,195 A | 5/2000 | Wu |
| 6,068,979 A | 5/2000 | Akhavan-Tafti |
| 6,075,014 A | 6/2000 | Weston et al. |
| 6,096,784 A | 8/2000 | Lerner et al. |
| 6,140,496 A | 10/2000 | Benner |
| 6,174,458 B1 | 1/2001 | Koga et al. |
| 6,177,440 B1 | 1/2001 | Bach et al. |
| 6,203,986 B1 | 3/2001 | Singer et al. |
| 6,218,445 B1 | 4/2001 | Priou et al. |
| 6,221,589 B1 | 4/2001 | Lane et al. |
| 6,232,462 B1 | 5/2001 | Collins et al. |
| 6,242,184 B1 | 6/2001 | Singer et al. |
| 6,261,779 B1 * | 7/2001 | Barbera-Guillem ........................ G01N 33/54306 435/6.11 |
| 6,262,319 B1 | 7/2001 | Barnes et al. |
| 6,268,147 B1 | 7/2001 | Beattie et al. |
| 6,271,015 B1 | 8/2001 | Gilula et al. |
| 6,306,643 B1 | 10/2001 | Gentalen et al. |
| 6,329,152 B1 | 12/2001 | Patterson |
| 6,352,827 B1 | 3/2002 | Lin et al. |
| 6,365,362 B1 | 4/2002 | Terstappen et al. |
| 6,418,382 B2 | 7/2002 | Rothberg et al. |
| 6,423,378 B1 | 7/2002 | Cotting et al. |
| 6,428,957 B1 | 8/2002 | Delenstarr |
| 6,472,187 B1 | 10/2002 | Tonoike et al. |
| 6,503,714 B1 | 1/2003 | Weindel et al. |
| 6,528,802 B1 | 3/2003 | Koenig et al. |
| 6,534,266 B1 | 3/2003 | Singer |
| 6,562,575 B1 | 5/2003 | Dahl |
| 6,586,240 B1 | 7/2003 | Singer et al. |
| 6,600,066 B1 | 7/2003 | Schottek et al. |
| 6,610,475 B1 | 8/2003 | Kacian et al. |
| 6,617,125 B2 | 9/2003 | Adler, Jr. |
| 6,645,731 B2 | 11/2003 | Terstappen et al. |
| 6,670,464 B1 | 12/2003 | Shimkets et al. |
| 6,673,914 B1 | 1/2004 | Hoon |
| 6,753,046 B2 | 6/2004 | Manabe et al. |
| 6,818,260 B2 | 11/2004 | Farrand et al. |
| 6,852,490 B2 | 2/2005 | Gentalen et al. |
| 6,911,235 B2 | 6/2005 | Frances |
| 6,924,269 B2 | 8/2005 | Milijkovic et al. |
| 6,927,216 B2 | 8/2005 | Cherney et al. |
| 7,033,758 B2 | 4/2006 | Kenny et al. |
| 7,037,905 B2 | 5/2006 | Ebdrup et al. |
| 7,037,938 B2 | 5/2006 | Hattori et al. |
| 7,049,304 B2 | 5/2006 | Holmes-Farley et al. |
| 7,064,197 B1 | 6/2006 | Rabbani et al. |
| 7,074,836 B1 | 7/2006 | Kawada et al. |
| 7,101,915 B1 | 9/2006 | Kawada et al. |
| 7,148,219 B2 | 12/2006 | Lou et al. |
| 7,183,447 B2 | 2/2007 | Pauluth et al. |
| 7,214,492 B1 * | 5/2007 | Rublee ................. C12Q 1/6837 435/283.1 |
| 7,220,783 B2 | 5/2007 | Kawada et al. |
| 7,320,972 B2 | 1/2008 | Martinez et al. |
| 7,326,575 B2 | 2/2008 | Capodieci et al. |
| 7,351,452 B2 | 4/2008 | Goodby et al. |
| 7,351,728 B2 | 4/2008 | Brooks et al. |
| 7,399,845 B2 | 7/2008 | Seth et al. |
| 7,411,100 B2 | 8/2008 | Pauluth et al. |
| 7,425,281 B2 | 9/2008 | Wand et al. |
| 7,432,375 B2 | 10/2008 | Graczyk et al. |
| 7,473,767 B2 | 1/2009 | Dimitrov |
| 7,521,455 B2 | 4/2009 | Nagase et al. |
| 7,524,631 B2 | 4/2009 | Patterson et al. |
| 7,553,496 B2 | 6/2009 | Ambati |
| 7,582,681 B2 | 9/2009 | Baker et al. |
| 7,615,351 B2 | 11/2009 | McMaster |
| 7,626,020 B2 | 12/2009 | Butlin et al. |
| 7,645,776 B2 | 1/2010 | Ackermann et al. |
| 7,709,198 B2 | 5/2010 | Luo et al. |
| 7,767,277 B2 | 8/2010 | Lietzau et al. |
| 7,776,922 B2 | 8/2010 | Bruggemeier et al. |
| 7,803,541 B2 | 9/2010 | Luo et al. |

(56) References Cited

U.S. PATENT DOCUMENTS

| | | |
|---|---|---|
| 7,888,032 B2 | 2/2011 | Patterson et al. |
| 7,927,798 B2 | 4/2011 | Zheng et al. |
| 7,951,539 B2 | 5/2011 | McMaster et al. |
| 7,968,327 B2 | 6/2011 | McMaster et al. |
| 7,999,137 B2 | 8/2011 | Kunz et al. |
| 8,017,360 B2 | 9/2011 | Luo et al. |
| 8,389,219 B2 | 3/2013 | Anthony et al. |
| 8,470,535 B2 | 6/2013 | McMaster et al. |
| 8,470,563 B2 | 6/2013 | Kermekchiev et al. |
| 8,557,973 B2 | 10/2013 | Anthony et al. |
| 8,653,250 B2 | 2/2014 | Patterson |
| 8,658,361 B2 | 2/2014 | Wu et al. |
| 8,685,646 B2 | 4/2014 | Battersby et al. |
| 8,986,931 B2 | 3/2015 | Luo et al. |
| 10,081,825 B2* | 9/2018 | Arnold .............. C12Q 2537/162 |
| 2002/0034753 A1 | 3/2002 | Yang et al. |
| 2002/0034754 A1 | 3/2002 | Reed et al. |
| 2002/0164769 A1 | 7/2002 | Curtis et al. |
| 2002/0106644 A1 | 8/2002 | Rosenow |
| 2002/0172950 A1 | 11/2002 | Kenny et al. |
| 2002/0172953 A1 | 11/2002 | Mirkin et al. |
| 2002/0187470 A1 | 12/2002 | Casey et al. |
| 2003/0036065 A1* | 2/2003 | Gellibolian .......... C12Q 1/6837 506/16 |
| 2003/0096854 A1 | 5/2003 | Lin et al. |
| 2003/0165935 A1 | 9/2003 | Vann et al. |
| 2003/0170613 A1 | 9/2003 | Straus et al. |
| 2003/0211489 A1 | 11/2003 | Shen et al. |
| 2004/0023248 A1 | 2/2004 | O'Malley |
| 2004/0023393 A1 | 2/2004 | Monahan et al. |
| 2004/0067907 A1 | 4/2004 | Hagstrom et al. |
| 2004/0072231 A1 | 4/2004 | Mirkin et al. |
| 2004/0076954 A1 | 4/2004 | Caldwell et al. |
| 2004/0086930 A1 | 5/2004 | Tereba et al. |
| 2004/0091880 A1 | 5/2004 | Wiebusch et al. |
| 2004/0115475 A1 | 6/2004 | Hashimoto |
| 2004/0115686 A1 | 6/2004 | Dolginow et al. |
| 2004/0204473 A1 | 10/2004 | Lin et al. |
| 2004/0265934 A1 | 12/2004 | Stender et al. |
| 2005/0003366 A1* | 1/2005 | Getts .................. C12Q 1/6837 435/6.11 |
| 2005/0009063 A1 | 1/2005 | Xia et al. |
| 2005/0019842 A1 | 1/2005 | Prober et al. |
| 2005/0037397 A1 | 2/2005 | Mirkin et al. |
| 2005/0090383 A1 | 4/2005 | Thiele et al. |
| 2005/0170370 A1 | 8/2005 | Rabbani et al. |
| 2005/0181463 A1 | 8/2005 | Rao et al. |
| 2005/0282220 A1 | 12/2005 | Prober et al. |
| 2006/0058527 A1 | 3/2006 | Kirsch et al. |
| 2006/0172284 A1 | 8/2006 | Zheng et al. |
| 2006/0172285 A1 | 8/2006 | Patterson et al. |
| 2006/0199213 A1 | 9/2006 | Capodieci et al. |
| 2006/0211698 A1 | 9/2006 | Boryanski et al. |
| 2006/0263769 A1 | 11/2006 | Luo et al. |
| 2006/0286583 A1 | 12/2006 | Luo et al. |
| 2006/0293502 A1 | 12/2006 | Dreyer et al. |
| 2007/0010559 A1 | 1/2007 | Christiansen et al. |
| 2007/0015003 A1 | 1/2007 | Hwang et al. |
| 2007/0015188 A1 | 1/2007 | Luo et al. |
| 2007/0082877 A1 | 4/2007 | Dunkel et al. |
| 2007/0125712 A1 | 6/2007 | Little et al. |
| 2007/0161015 A1 | 7/2007 | Zheng et al. |
| 2007/0161020 A1 | 7/2007 | Luo et al. |
| 2008/0008994 A1 | 1/2008 | Stender et al. |
| 2008/0038725 A1 | 2/2008 | Luo et al. |
| 2008/0050746 A1 | 2/2008 | McMaster et al. |
| 2008/0176242 A1 | 7/2008 | McMaster et al. |
| 2008/0188371 A1 | 8/2008 | Fischer et al. |
| 2008/0220979 A1 | 9/2008 | Wang et al. |
| 2008/0242708 A1 | 10/2008 | Dunkel et al. |
| 2009/0005321 A1 | 1/2009 | Zimmer et al. |
| 2009/0081688 A1 | 3/2009 | Luo et al. |
| 2009/0170060 A1 | 7/2009 | Kermekchiev |
| 2009/0181360 A1 | 7/2009 | Chen et al. |
| 2009/0298709 A1 | 12/2009 | Luo |
| 2010/0081131 A1 | 4/2010 | Ach et al. |
| 2010/0086925 A1 | 4/2010 | Lee et al. |
| 2010/0190167 A1* | 7/2010 | Getts .................. C12Q 1/682 435/5 |
| 2011/0059442 A1 | 3/2011 | Luo et al. |
| 2011/0059866 A1 | 3/2011 | Luo et al. |
| 2011/0105351 A1 | 5/2011 | Luo et al. |
| 2011/0171644 A1 | 7/2011 | Luo et al. |
| 2011/0223606 A1 | 9/2011 | McMaster et al. |
| 2011/0256536 A1 | 10/2011 | McMaster et al. |
| 2012/0003625 A1 | 1/2012 | Zhang et al. |
| 2012/0003648 A1 | 1/2012 | Ma et al. |
| 2012/0004132 A1 | 1/2012 | Zhang et al. |
| 2012/0009577 A1 | 1/2012 | Luo et al. |
| 2012/0052498 A1 | 3/2012 | Nguyen et al. |
| 2012/0071343 A1 | 3/2012 | Ma et al. |
| 2012/0100540 A1 | 4/2012 | Wu et al. |
| 2012/0157348 A1 | 6/2012 | Zheng et al. |
| 2012/0172246 A1 | 7/2012 | Nguyen et al. |
| 2012/0178081 A1 | 7/2012 | Nguyen et al. |
| 2012/0214152 A1 | 8/2012 | Ma et al. |
| 2012/0301886 A1 | 11/2012 | Farrell et al. |
| 2013/0023433 A1 | 1/2013 | Luo |
| 2013/0171621 A1 | 6/2013 | Luo et al. |
| 2013/0294826 A1 | 11/2013 | Chen |
| 2014/0178869 A1 | 6/2014 | Ma et al. |
| 2014/0194296 A1 | 7/2014 | Luo et al. |
| 2014/0249040 A1 | 9/2014 | Wu et al. |
| 2014/0357509 A1 | 12/2014 | Ma et al. |
| 2015/0045251 A1 | 2/2015 | Wang et al. |

FOREIGN PATENT DOCUMENTS

| | | |
|---|---|---|
| WO | WO 1994/00598 A1 | 1/1994 |
| WO | WO 2001/94632 A2 | 12/2001 |
| WO | WO 2004/020654 A2 | 3/2004 |
| WO | WO 2006/002433 A2 | 1/2006 |
| WO | WO 2006/124771 A2 | 11/2006 |
| WO | WO 2007/001986 A2 | 1/2007 |
| WO | WO 2007/002006 A2 | 1/2007 |
| WO | WO 2010/060103 A1 | 5/2010 |
| WO | WO 2010/129941 A1 | 11/2010 |
| WO | WO 2011/038403 A1 | 3/2011 |
| WO | WO 2011/094669 A1 | 8/2011 |
| WO | WO 2012/040168 A2 | 3/2012 |
| WO | WO 2012/054795 A1 | 4/2012 |
| WO | WO 2012/103414 A2 | 8/2012 |
| WO | WO 2013/134442 A1 | 9/2013 |
| WO | WO 2013/152295 A1 | 10/2013 |
| WO | WO 2014/160949 A1 | 10/2014 |

OTHER PUBLICATIONS

"Viruses", Wikipedia.com, accessed Nov. 24, 2012. (Year: 2012).*
"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
Archaea, Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
Ahern, "Biochemical, Reagents Kits Offer Scientists Good Return on Investment," The Scientist, 9:1-4 (1995).
Alexandrescu et al., "Melanoma-Specific Marker Expression in Skin Biopsy Tissues as a Tool to Facilitate Melanoma Diagnosis," The Journal of Investigative Dermatology, 130(7): 1887-1892 (2010).
Al-Soud et al. "A sample preparation method which facilitates detection of bacteria in blood cultures by the polymerase chain reaction," *J. Microbiol. Meth.*, 32:217-224 (1998).
Amatschek, et al., "CXCL9 induces chemotaxis, chemorepulsion and endothelial barrier disruption through CXCR3-mediated activation of melanoma cells," British J. Cancer, 104:469-479 (2011).

(56) References Cited

OTHER PUBLICATIONS

Anderson et al., "Fully automated RNAscope in situ hybridization assays for formalin-fixed paraffin-embedded cells and tissues," *J. Cell Biochem.*, 117(10):2201-2208 (2016).
Ang et al., "Human papillomavirus and survival of patients with oropharyngeal cancer," *N. Engl. J. Med.*, 363(1):24-35 (2010).
Application Note From Amersham Biosciences, "Whole genome amplification from crude blood lysates," 2003 (4 pages).
Application Note From Applied Biosystems, "Total RNA purification from whole blood," 2002 (6 pages).
Bach et al., "Magnetic capture-hybridization method for purification and probing of mRNA for neutral protease of Bacillus cereus," J Microbiological Methods, 37:187-192 (1999).
Balch, et al., "An Evidence-based Staging System for Cutaneous Melanoma". CA: Cancer J. Clinicians, 54:131-149 (2004).
Balnaves et al., "Direct PCR from CVS and blood lysates for detection of cystic fibrosis and Duchenne muscular dystrophy deletions," Nucl. Acids. Res., 19(5):1155 (1991).
Bastian, et al., "Classifying melanocytic tumors based on DNA copy number changes" Am. J. Pathology, 163:765-770 (2003).
Bobrow et al., "Tyramide signal amplification (TSA) systems for the enhancement of ISH signals in cytogenetics," Current Protocols in Cytometry, John Wiley & Sons, Inc., US, Supplement 11, pp. 8.9.1-8.9.16 (2000).
Böni, et al., "Ca(2+)-binding proteins S100A6 and S100B in primary cutaneous melanoma," J. Cutaneous Pathology, 24:76-80 (1997).
Bortolin et al., "Analytical validation of the tag-it high-throughput microsphere-based universal array genotyping platform: application to the multiplex detection of a panel of thrombophilia-associated single-nucleotide polymorphisms," *Clin. Chem.*, 50(11):2028-2036 (2004).
Borucki et al., "Suspension microarray with dendrimer signal amplification allows direct and high-throughput subtyping of Listeria monocytogenes from genomic DNA," *J. Clin. Microbiol.*, 43(7):3255-3259 (2005).
Brown, et al., "Osteopontin expression and distribution in human carcinomas," Am. J. Pathology, 145:610-623 (1994).
Burris et al., "A novel method for analysis of nuclear receptor function at natural promoters: peroxisome proliferator-activated receptor .gamma. agonist actions on aP2 gene expression detected using branched DNA messenger RNA quantitation," *Mol. Endocrinol.*, 13(3):410-417 (1999).
Bushnell et al., "ProbeDesigner: for the design of probesets for branched DNA (bDNA) signal amplification assays," *Bioinformatics*, 15(5):348-355 (1999).
Chung et al., "Human papillomavirus in head and neck cancer: its role in pathogenesis and clinical implications," *Clin. Cancer Res.*, 15:6758-6762 (2009).
Cole et al., "Monoclonal Antibodies in Cancer Therapy", Allen R. Bliss, Inc., pp. 77-96 (1985).
Collins et al., "A branched DNA signal amplification assay for quantification of nucleic acid targets below 100 molecules/ml," *Nucl. Acids Res.*, 25(15):2979-2984 (1997).
Collins et al., "Branched DNA (bDNA) technology for direct quantification of nucleic acids: design and performance," in Gene Quantification, F. Ferre, ed., pp. 205-223 (1998).
Conway et al., "Gene expression porfilling of paraffin-embedded primary melanoma using the DASL assay idenitifies increased osteopontin expression as predictive of reduced relapse-free survial,," J. Am. Assoc. Cancer Res., 15(22):6939-6949 (2009).
D'Souza et al., "Case-control study of human papillomavirus and oropharyngeal cancer," *N. Engl. J. Med.* , 356(19):1944-1956 (2007).
De Vries et al., "PCR on cell lysates obtained from whole blood circumvents DNA isolation," *Clin. Chem.*, 47(9):1701-1702 (2001).
Deichmann et al., "Ultra-sensative fish is a useful tool for studying chronic HIV-I infection," J. Virological Methods, 65(1):19-25 (1997).
Dimitrov et al., "Prediction of hybridization and melting for double-stranded nucleic acids," *Biophysical J.*, 87(1):215-226 (2004).

Drmanac et al., "Accurate sequencing by hybridization for DNA diagnostics and individual genomics," Nat. Biotechnol.,16:54-58 (1998).
El-Tanani et al., "The regulation and role of osteopontin in malignant transformation and cancer" Cytokine Growth Factor Rev., 17:463-74 (2006).
Finak et al., "Stromal gene expression predicts clinical outcome in breast cancer," Nat. Med., 14:518-527 (2008).
Flagella et al., "A multiplex branched DNA assay for parallel quantitative gene expression profiling," *Anal. Biochem.*, 352(1):50-60 (2006).
Fulton et al., "Advanced multiplexed analysis with the FlowMetrix system," *Clin. Chem.*, 43(9):1749-1756 (1997).
Gaiser et al., "Classifying ambiguous melanocytic lesions with FISH and correlation with clinical long-term follow up," Mod. Pathol., 23:413-419 (2010).
Gentalen and Chee, "A novel method for determining linkage between DNA sequences: hybridization to paired probe arrays," *Nucl. Acids Res.*, 27(6):1485-1491 (1999).
Gerami et al., "Fluorescence in situ hybridization (FISH) as an ancillary diagnostic tool in the diagnosis of melanoma," Am. J. Surg. Pathol., 33:1146-1156 (2009).
Gerlinger et al., "Intratumor heterogeneity and branched evolution revealed by multiregion sequencing," *N. Engl. J. Med.*, 366(10):883-892 (2012).
Glusac, "The melanoma "epidemic", a dermatopathologist's perspective," J. Cutan. Pathol., 38:264-267 (2011).
Hanahan et al., "Hallmarks of Cancer: The Next Generation," Cell, 144:646-674 (2011).
Haqq et al., "The gene expression signatures of melanoma progression," Proc. Natl. Acad. Sci. USA, 102:6092-6097 (2005).
Harlin et al., "Chemokine expression in melanoma metastases associated with CD8+ T-cell recruitment,," Cancer Res., 69(7):3077-3085 (2009).
Hartley et al., "Detection of chemical-induced differential expression of rat hepatic cytochrome P450 mRNA transcripts using branched DNA signal amplification technology," *Drug Metabolism and Disposition*, 28(5):608-616 (2000).
Harvell et al., "High-resolution array-based comparative genomic and melanomas," Diagn. Mol. Pathol., 94305:22-25 (2004).
Henriksen et al., "Dual color CISH and FISH to SISH conversion,"IHC Staining Methods, 5th Edition, 97-101 (2009).
Hicks et al., "In situ hybridization in the pathology laboratory: general principles, automation, and emerging research applications for tissue-based studies of gene expression," *J. Mol. Histol.*, 35(6):595-601 (2004).
Higuchi, "DNA from whole blood for PCR," Amplifications, 2:1-3. [online]. The Jackson Laboratory, 1998. [retrieved on Jul. 24, 2009]. Retrieved from the internet:<URL: http//www.jax.org.imr.whole. sub.--blood.html>.
Hines et al., "Human papillomaviruses: their clinical significance in the management of cervical carcinoma," *Oncology*, 9(4):279-285 (1995).
Ho et al., "Type-specific human papillomavirus oncogene messenger RNA levels correlate with the severity of cervical neoplasia," *Intl. J. Cancer*, 127(3):622-632 (2010).
Hsu et al., "Melanoma development and progression: a conspiracy between tumor and host," Differentiation, 70:522-536 (2002).
Huse et al., "Generation of a large combinatorial library of the immunoglobulin repertoire in phage lambda," Science, 246:1275-1281 (1989).
Iannone, "Multiplexed single nucleotide polymorphism genotyping by oligonucleotide ligation and flow cytometry," *Cytometry*, 39(2):131-140 (2000).
Ikeda et al., "Characterization of an antigen that is recognized on a melanoma showing partial HLA loss by CTL expressing an NK inhbiitory receptor," Immunity, 6(2):199-208 (1997).
Jemal et al., "Cancer Statistics," CA Cancer J. Clin., 60(5):277-300 (2010).
Kashani-Sabet et al.,"A multi-marker assay to distinguish malignant melanomas from benign nevi," Proc. Natl. Acad. Sci. USA, 106:6268-6272 (2009).

(56) References Cited

OTHER PUBLICATIONS

Kenny et al., "Detection of viral infection and gene expression in clinical tissue specimens using branched DNA (bDNA) in situ hybridization," J. Histochem. Cytochem., 50(9):1219-1227 (2002).
Kern et al., "An enhanced-sensitivity branched-DNA assay for quantification of human immunodeficiency virus type 1 RNA in plasma," J. Clin. Microbiol., 34(12):3196-3202 (1996).
Khaitan et al., "The melanoma-upregulated long noncoding RNA SPRY4-IT1 modulates apoptosis and invasion," Cancer Research, 71(11):3852-3862 (2011).
Kjaer et al., "Long-term absolute risk of cervical intraepithelial neoplasia grade 3 or worse following human papillomavirus infection: role of persistence," J. Natl. Cancer Inst., 102(19):1478-1488 (2010).
Koh et al., "Molecular classification of melanomas and nevi using gene expression microarray signatures and formalin-fixed and paraffin-embedded tissue," Mod. Pathol., 22:538-546 (2009).
Kohler and Milstein, "Derivation of specific antibody-producing tissue culture and tumor lines by cell fusion," Eur. J. Immunol., 6:511-519 (1976).
Kozbar et al., "The production of monclonal antibodies from human lymphocytes," Immunol. Today 4:72-79 (1983).
Laakso et al., "Dual-colour chromogenic in situ hybridization for testing of HER-2 oncogene amplification in archival breast tumours," J. Patho., 210:3-9 (2006).
Landis et al., "Cancer statistics, 1999," CA Cancer J. Clin., 49(1):8-31 (1999).
Lewin & Stewart-Haynes, "A simple method for DNA extraction from leukocytes for use in PCR," BioTechniques, 13(4):522-524 (1992).
Lewis et al., "p16 positive oropharyngeal squamous cell carcinoma: an entity with a favorable prognosis regardless of tumor HPV status," Am. J. Surg. Pathol., 34(8):1088-1096 (2010).
Liu et al., "Detection of circulating cancer cells in lung cancer patients with a panel of marker genes," Biochem. Biophys. Res. Comm., 372(4):756-760 (2008).
Lizard et al., "In situ hybridization detection of single-copy human papillomavirus on isolated cells, using a catalyzed singal amplification system: genpoint," Diagnostic Cytopathology, 24(2):112-116 (2001).
Lo et al., "Fetal DNA in maternal plasma: biology and diagnostic applications," Clin. Chem., 46(12):1903-1906 (2000).
Majlessi et al., "Advantages of 2'-O-methyl oligoribonucleotide probes for detecting RNA targets," Nucleic Acids Res., 26(9):2224-2229 (1998).
Malygin et al, Hybridization of two oligodeoxynucleotides to both strands of an RNA hairpin structure increases the efficiency of RNA-DNA duplex formation, FEBS Letters, 392:114-116 (1996).
Manafi et al., "Flourogenic and chromogenic substrates used in bacterial diagnostics," Microbiol. Rev., 55(3):335-348 (1991).
Marur et al., "HPV-associated head and neck cancer: a virus-related cancer epidemic," Lancet Oncol., 11(8):781-789 (2010).
Masand et al., "Adenosquamous carcinoma of the head and neck: relationship to human papillomavirus and review of the literature," Head Neck Pathol.,5(2):108-116 (2011).
Mauerer et al., "Identification of new genes associated with melanoma," Experimental Dermatology 20(6):502-507 (2011).
Maxam et al., "A new method for sequencing DNA," Proc. Natl. Acad. Sci. USA, 74:560-564 (1977).
Meijer et al., "Clinical utility of HPV genotyping," Gynecol. Oncol., 103(1):12-17 (2006).
Mercier et al., "Direct PCR from whole blood, without DNA extraction," Nucl. Acids. Res., 18(19):5908 (1990).
Miller et al., "Melanoma," N. Eng. J. Med., 355:51-65 (2006).
Mocellin et al., "Molecular Detection of Circulating Tumor Cells in an Independent Prognostic Factor in Patients with High-Risk Cutaneous Melanoma," International Journal of Cancer, 111(5): 741-745 (2004).
Mocellin et al., "Sentinel lymph node molecular ultrastaging in patients with melanoma: a systematic review and meta-analysis of prognosis," J. Clin. Oncol., 25:1588-1595 (2007).
Moody et al., "Human papillomavirus oncoproteins: pathways to transformation," Nat. Rev. Cancer, 10(8):550-560.
Narayanan, "Overview of principles and current uses of DNA probes in clinical and laboratory medicine," Ann. Clin. Lab. Sci., 22(6):353-376 (1992).
Naucler et al., "Human papillomavirus and papanicolaou tests to screen for cervical cancer," N. Engl. J. Med., 357(16):1589-1597 (2007).
Nolte, "Branched DNA signal amplification for direct quantitation of nucleic acid sequences in clinical specimens," Adv. Clin. Chem., 33(1):201-235 (1998).
Nordvag et al., "Direct PCR of washed blood cells," BioTechniques, 12(4):490-493 (1992).
Ostor, "Natural history of cervical intraepithelial neoplasia: a critical review," Int. J. Gynecol. Pathol., 12(2):186-192 (1993).
Paik et al., "A multigene assay to predict recurrence of tamoxifen-treated, node-negative breast cancer," N. Eng. J. Med.,351:2817-2826 (2004).
Panici et al., "Predictive value of multiple tumor marker assays in second-look procedures for ovarian cancer," Gyneco. Oncol., 35(3):286-289 (1989).
Peterson et al., "LNA: a versatile tool for therapeutics and genomics," Trends Biotechnol., 21(2):74-81 (2003).
Player et al., "Single-copy gene detection using branched DNA (bDNA) in situ hybridization" J. Histochem. Cytochem., 49:603-611 (2001).
Prieto and Shea "Use of immunohistochemistry in melanocytic lesions," J. Cutan. Pathol., 35(Suppl 2):1-10 (2008).
Qian et al., "Recent developments in signal amplification methods for in situ hybridization," Diagnostic Mol. Pathol., 12(1):1-13 (2003).
Riker et al., "The gene expression profiles of primary and metastatic melanoma yields a transition point of tumor progression and metastasis," BMC Med. Genomics, 1;1-13 (2008).
Robinson et al., "Refining the diagnosis of oropharyngeal squamous cell carcinoma using human papillomavirus testing," Oral Oncol., 46(7):492-496 (2010).
Sagara et al., "Scapinin, the protein phosphatase 1 binding protein, enhances cell spreading and motility by interacting with the actin cytoskeleton," PLoS One 4(1):e4247 (2009).
Sanger et al., "DNA sequencing with chain-termininating inhibitors," Proc. Natl. Acad. Sci USA, 74(12):5463-5467 (1977).
Santalucia, "A unified view of polymer, dumbbell, and oligonucleotide DNA nearest-neighbor thermodynamics," Proc. Natl. Acad. Sci. USA, 95(4):1460-1465 (1998).
Scatolini et al., "Altered molecular pathways in melanocytic lesions," Int. J. Cancer,126:1869-1881 (2010).
Schiffman et al., "Human papillomavirus and cervical cancer," Lancet 370(9590):890-907 (2007).
Schweitzer & Kingsmore, "Combining nucleic acid amplification and detection," Curr. Opin. Biotechnol., 12(1):21-27 (2001).
Shah et al., "Detection of *Mycobacterium tuberculosis* directly from spiked human sputum by Q-beta replicase-amplifiied assay," J. Clin. Microbiol., 33(2):322-328 (1995).
Shah et al., "Novel, ultrasensitive, Q-beta, replicase-amplified hybridization assay for detection of Chlamydia trachomatis," J. Clin. Microbiol., 32(11):2718-2724 (1994).
Shah et al., "Ultra-sensitive and specific detections of porcine endogenous retrovirus (PERV) using a sequence-capture real-time PCR approach," J. Virol.Meth., 109:209-216 (2003).
Shen et al., "Quantification of cytokine mRNA in peripheral blood mononuclear cells using branched DNA (bDNA) technology," J. Immunol. Meth., 215(1-2):123-134 (1998).
Shevde et al.,"Osteopontin: an effector and an effect of tumor metastasis," Curr. Mol. Med., 10:71-81 (2010).
Shi et al., "Comparitive prognostic value of HPV16 E6 mRNA compared with in situ hybridization for human oropharyngeal squamous carcinoma," J. Clin. Oncol., 27(36):6213-6221 (2009).

(56) References Cited

OTHER PUBLICATIONS

Shoo et al., "Discordance in the histopathologic diagnosis of melanoma at a melanoma referral center," J. Am. Acad. Dermatol., 62:751-756 (2010).
Sleijfer et al., "Circulating tumour cell detection on its way to routine diagnostic implementation?" European Journal of Cancer, 43(18):2645-2650 (2007).
Smeets et al., "A novel algorithm for reliable detection of human papillomavirus in paraffin embedded head and neck cancer specimen," Intl. J. Cancer, 121(11):2465-2472 (2007).
Smith et al., "Whole-genome expression profiling of the melanoma progression pathway reveals marked molecular differences between nevi/melanoma in situ and advanced-stage melanomas," Cancer Biol. Ther., 4:1018-1029 (2005).
Smyth, "Linear models for microarray data. Bioinformatics and Computational Biology Solutions using R and Bioconductor," R. Gentleman, V. Carey, S. Dudoit, R. Irizarry, W. Huber (eds.), Springer, New York, pp. 397-420 (2005).
Soikkeli et al., "Systematic search for the best gene expression markers for melanoma micrometastasis detection," J. Pathol., 213:180-189 (2007).
Solomon et al., "Cervical cancer screening rates in the United States and the potential impact of implementation of screening guidelines," CA Cancer J. Clin., 57(2):105-111 (2007).
Speel et al., "Tryamide signal amplification for DNA and mRNA in situ hybridization," Methods Mol. Biol., 326:33-60 (2006).
Speel et al., "A novel triple-color detection procedure for brightfield microscopy, combining in situ hybridization with immunocytochemistry," J. Histochem. Cytochem., 42(10):1299-1307 (1994).
Stoler et al., "Interobserver reproducibility of cervical cytologic and histologic interpretations: realistic estimates from the ASCUS-LSIL Triage Study," JAMA, 285(11):1500-1505 (2001).
Stoler, "In situ hybridization," Clin. Lab. Med., 10(1):215-236 (1990).
Stone et al., "Detection of rRNA from four respiratory pathogens using an automated Qβ replicase assay," Mol. Cell. Probes, 10:359-370 (1996).
Suzuki et al., "In situ hybridization: an informative technique for pigment cell researchers," Pigment Cell Res., 17:10-14 (2004).
Syrjanen, "Spontaneous evolution of intraepithelial lesions according to the grade and type of the implicated human papillomavirus (HPV)," Eur. J. Obstet. Gynecol. Reprod. Biol., 65(1):45-53 (1996).
Taback et al., "The clinical utility of multimarker RT-PCR in the detection of occult metastasis in patients with melanoma," Recent Results in Cancer Res., 158:78-92 (2001).
Talantov et al., "Novel genes associated with malignant melanoma but not benign melanocytic lesions," Clin. Cancer Res., 11:7234-7242 (2005).
Thomison et al., "Human papillomavirus: molecular and cytologic/histologic aspects related to cervical intraepithelial neoplasia and carcinoma," Hum. Pathol., 39(2):154-166 (2008).
Troxel, "Aspects of error in pathology," Arch. Pathol. Lab. Med., 130:617-619 (2006).
Tsai et al., "Nucleic acid capture assay, a new method for direct quantitation of nucleic acids," Nucl. Acids Res., 31(6):e25 (2003).
Ugozzoli et al., "Detection of specific alleles by using allele-specific primer extension followed by capture on solid support," GATA, 9(4):107-112 (1992).
Ugurel et al., "Tumor biomarkers in melanoma," Cancer Control: Journal of the Moffitt Cancer Center 16:219-224 (2009).
Ukpo et al., "High-Risk Human Papillomavirus E6/E7 mRNA Detection by a Novel In-Situ Hybridization Assay Strongly Correlates with p16 Expression and Patient Outcomes in Oropharyngeal Squamous Cell Carcinoma," Am. J. Surg. Pathol., 35:1343-1350 (2011).
Urso et al., "Sensitivity and specificity of histological criteria in the diagnosis of conventional cutaneous melanoma," Melanoma Res., 18:253-258 (2008).
Van Cleve et al, "Direct quantitation of HIV by flow cytometry using branched DNA signal amplification," Molecular and Celluar Probes, 12:243-247 (1998).
Van't Veer et al., "Gene expression profiling predicts clinical outcome of breast cancer," Nature 415:530-536 (2002).
Veenhuizen et al., "Quality assessment by expert opinion in melanoma pathology: experience of the pathology panel of the Dutch Melanoma Working Party," J. Pathol., 182:266-272 (1997).
Vergier et al., "Fluorescence in situ hybridization, a diagnostic aid in ambiguous melanocytic tumors: European study of 113 cases," Mod. Pathol., 24(5):613-623 (2011).
Wai et al., "Osteopontin: regulation in tumor metastasis," Cancer Metastasis Rev., 27:103-118 (2008).
Wang et al., "RNAscope: A novel in situ RNA analysis platform for formalin-fixed, parafiin-embedded tissues," J. Mol. Diagnostics, 14(1):22-29 (2012).
Wang et al., "Multiplex Analysis of Gene Expression in Single Cells for Circulating Tumor Cell Detection," Proceedings of the American Association for Cancer Research Annual Meeting, 49: 1224-1225 (2008).
Wang et al., "Regulation of insulin preRNA splicing by glucose," Proc. Nat. Acad. Sci. USA, 94(9):4360-4365 (1997).
Welch et al., "Overdiagnosis in Cancer," J. Natl. Cancer Inst., 102:605-613 (2010).
Well, "Human papillomavirus associated lesions of the lower female genital tract," Advances in Gynacological Pathology, Lowe and Fox eds., Churchill Livingstone, United Kingdom, 79-97 (1992).
Westekemper et al., "Expression of MCSP and PRAME in conjunctival melanoma," Br. J. Ophtalmol., 94:1322-1327 (2010).
Wilber & Urdea, "Quantification of HCV RNA in clinical specimens by branched DNA (bDNA) technology," Methods in Molecular Medicine: Hepatitis C 19:71-78 (1998).
Wilson et al., "A multiplexed PCR-coupled liquid bead array for the simultaneous detection of four biothreat agents," Mol.Cell. Probes, 19(2):137-144 (2005).
Wright et al., "2006 consensus guidelines for the management of women with cervical intraepithelial neoplasia or adenocarcinoma in situ," Am. J. Obstet. Gynecol., 197(4):340-345 (2007).
Wright et al., "2006 consensus guidelines for the management of women with cervical intraepithelial neoplasia or adenocarcinoma in situ," J. Low Genit. Tract Dis., 11(4):223-239 (2007).
Wright et al., "Precancerous lesions of the cervix," Blausteins pathology of the female genital tract, Kurman ed., 5th ed. New York: Springer, 253-324 (2002).
Wu et al., "Quantification of CYP1A1 and 1B1 mRNA in polycyclic aromatic hydrocarbon-treated human T-47D and HepG2 cells by a modified bDNA assay using fluorescence detection," Analytical Biochemistry, 312:162-166 (2003).
Yang et al., "Artificially expanded genetic information system: a new base pair with an alternative hydrogen bonding pattern," Nucleic Acids Res., 34(21):6095-6101 (2006).
Yang et al., "BADGE, Beads Array for the Detection of Gene Expression, a high-throughput diagnostic bioassay," Genome Res., 11(11):1888-1898 (2001).
Yang et al., "Sensitive detection of human papillomavirus in cervical, head/neck, and schistosomiasis-associated bladder malignancies," Proc. Natl. Acad. Sci. U.S.A., 102(21):7683-7688 (2005).
Zhang et al., "Small interfering RNA and gene expression analysis using a multiplex branched DNA assay without RNA purification," J. Biomolecular Screening, 10(6):549-556 (2005).
Zhou et al., "Osteopontin expression correlates with melanoma invasion," J. Invest. Dermatol., 124:1044-1052 (2005).
Zolg et al., "High salt lysates: a simple method to stores blood samples without refrigeration for subsequent use with DNA probes," Am. J. Trop. Med. Hyg., 39(1):33-40 (1988).
Zheng et al., "Sensitive and quantitative measurement of gene expression directly from a small amount of whole blood," Clin. Chem., 52(7):1294-1302 (2006).
Andras et al., "Strategies for signal amplification in nucleic acid detection,"Mol. Biotech., 19(1):29-44 (2001).

(56) References Cited

OTHER PUBLICATIONS

Antao et al., "in situ hybridization using the bDNA technology," Chapter 6 in Techniques in Quantification and Localization of Gene Efdxpression, Maple-Vail Book Manufactoring Group, York, PA, pp. 81-93 (2000).
Beck et al., "Automated colorimetric in situ hybridization (CISH) detection of immunoglobulin (Ig) light chain mRNA expression in plasma cell (PC) dyscrasias and non-hodgkin lymphoma," *Diagnostic Mol. Pathol.*, 12(1):14-20 (2003).
Begley, "Psst, the human genome was never completely sequenced. Some scientists say it should be," *STATNews*, Jun. 20, 2017.
Engel et al., "Detection of circulating tumour cells in patients with breast or ovarian cancer by molecular cytogenetics," *Br. J. Cancer*, 81(7):1165-1173 (1999).
FDA letter entitled "Summary of safety and effectiveness," for Versant HIV-1 RNA 3.0 Assay (bDNA) which was approved on Sep. 11, 2002.
Femino et al., "Visualization of single RNA transcripts in situ," *Science*, 280:585-590 (1998).
Forster et al., "A human gut bacterial genome and culture collection for improved metagenomic analyses," *Nature Biotechnol.*, 37:186-192 (2019).
GenBank Accesion No. NM_006115.3; GI:46249365 (Aug. 14, 2011) [Retrieved from the Internet: May 5, 2014: <http://www.ncbi.nlm.nih.gov/nuccore/46249365?sat=14&satkey=11322805>].
GenBank Accession No. NM_000582.2; GI:38146097 (Sep. 11, 2011) [Retrieved from the Internet: May 5, 2014: <http://www.ncbi.nlm.nih.gov/nuccore/38146097?sat=14&satkey=11323949>].
GenBank Accession No. NM_001565; GI:323422857(Sep. 11, 2011) [Retrieved from the Internet: May 8, 2014: <http://www.ncbi.nlm.nih.gov/nuccore/323422857?sat=14&satkey=11587839>].
GenBank Accession No. NM_004864.2; GI:153792494 (Sep. 11, 2011) [Retrieved from the Internet: May 5, 2014: <http://www.ncbi.nlm.nih.gov/nuccore/153792494?sat=14&satkey=11014076>].
GenBank Accession No. NM_005511.1; GI:5031912 (Jul. 30, 2011) [Retrieved from the Internet: May 5, 2014: <http://www.ncbi.nlm.nih.gov/nuccore/5031912?sat=14&satkey=11013469>].
GenBank Accession No. NM_006272.2; GI:114520588 (Sep. 11, 2011) [Retrieved from the Internet: May 5, 2014:<http://www.ncbi.nlm.nih.gov/nuccore/114520588?sat=14&satkey=11323733>].
GenBank Accession No. NM_014624.3; GI:52352807 (Aug. 13, 2011) [Retrieved from the Internet: May 5, 2014: <http://www.ncbi.nlm.nih.gov/nuccore/52352807?sat=15&satkey=2395150>].
GenBank Accession No. NM_030948.1; GI:54144630 (Aug. 15, 2011) [Retrieved from the Internet: May 5, 2014: <http://www.ncbi.nlm.nih.gov/nuccore/336391123?sat=15&satkey=2277161>].

GSE3189 study (Gene Expression Omnibus Accession No. GSE3189, ID: 200003189, publicly available Aug. 25, 2005 printed from http://www.ncbi.nlm.nih.gov/geo/query/acc.cgi?acc=GSE3189 as pp. 1 /2-2/2.
Hicks et al.( 2004) "In situ hybridization in the pathology laboratory: General principles, automation, and emerging research applications for tissue-based studies of gene expression," *J Mol. Histol.*, 35(6):595-601.
Lang, "Demonstration of Kappa and Lambda light chains by dual chromogenic in situ hybridization of formalin-fixed, acid-decalcified, and paraffin-embedded bone marrow trephine biopsies," *The J. Histotechnol.*, 33(1):9-13 (2010).
Lewin & Stewart-Haynes (1992) "A simple method for DNA extraction from leukocytes for use in PCR," *BioTechniques*, 13(4):522-524.
McNicol et al., "Comparison of in situ hybridisation and polymerase chain reaction in the diagnosis of B cell lymphoma," *J. Clin. Pathol.*, 51:229-233 (1998).
Miller et al., "The Hypolipidemic and Anti-Inflammatory Activity of Boronated Aromatic Amino Acids in CF(1) Male Mice," *Met. Based Drugs* 6(6):337-344 (1999).
Santalucia Jr. (1998) "A unified view of polymer, dumbbell, and oligonucleotide DNA nearest-neighbor thermodynamics," *PNAS*, 95:1460-1465.
Schweitzer & Kingsmore (2001) "Combining nucleic acid amplification and detection," *Curr. Opin. Biotechnol.*, 12(1):21-27.
Seykora et al., "Gene expression profiling of melanocytic lesions," Am. J. Dermatopathol., 25:6-11 (2003).
Smirnov et al. (2005) "Global gene expression profiling of circulating tumor cells," *Cancer Res.*, 65(12):4993-4997.
Speel et al. (1999) "Amplification methods to increase the sensitivity of in situ hybridization: play card(s),"*J. Histochem. Cytochem.*, 47(3):281-288.
Stone et al. (1996) "Detection of rRNA form four respiratory pathogens using an automated QB replicase assay," *Mol. Cell. Probes*, 10:359.
Tubbs et al., "Ultrasensitive RNA in situ hybridization for detection of restricted clonal expression of low-abundance immunoglobulin light chain mRNA in B-cell lymphoproliferative. disorders," *Am. J. Clin. Pathol.*, 140:736-746 (2013).
Wright et al., "2006 consensus guidelines for the management of women with cervical intraepithelial neoplasia or adenocarcinoma in situ," *J. Low Genit. Tract Dis.*, 11(4):201-222 (2007).
Yao et al. "Multicenter evaluation of the VERSANT Hepatitis B virus DNA 3.0 assay," J. Clin. Microbiol., 42(2):800-806 (2004).

* cited by examiner

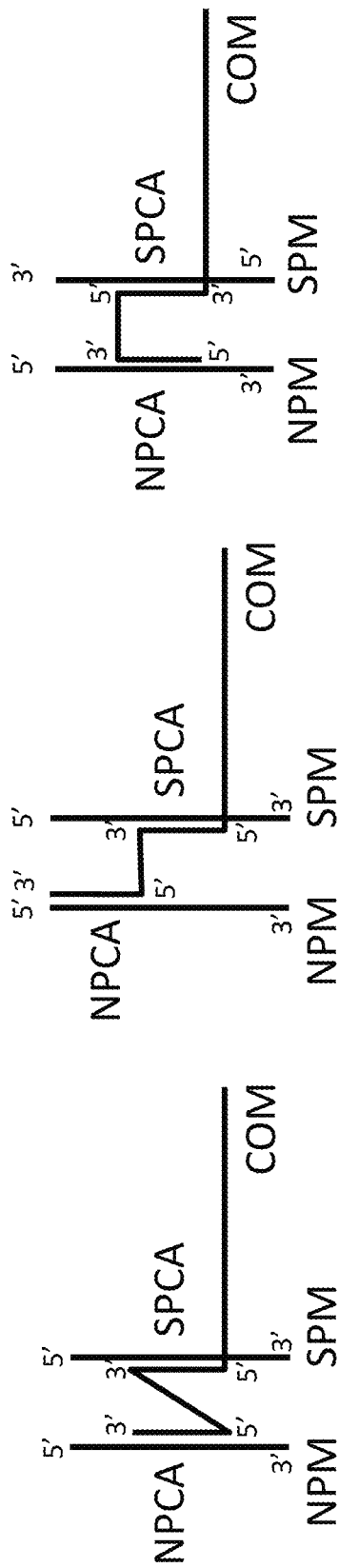

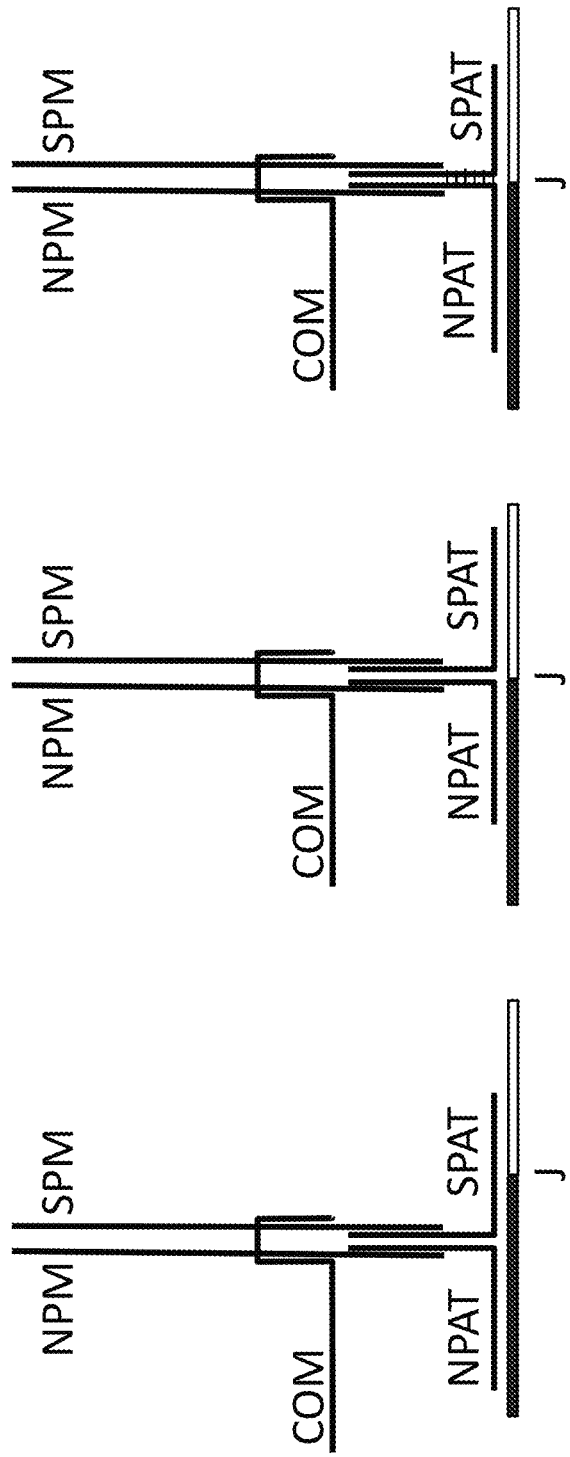

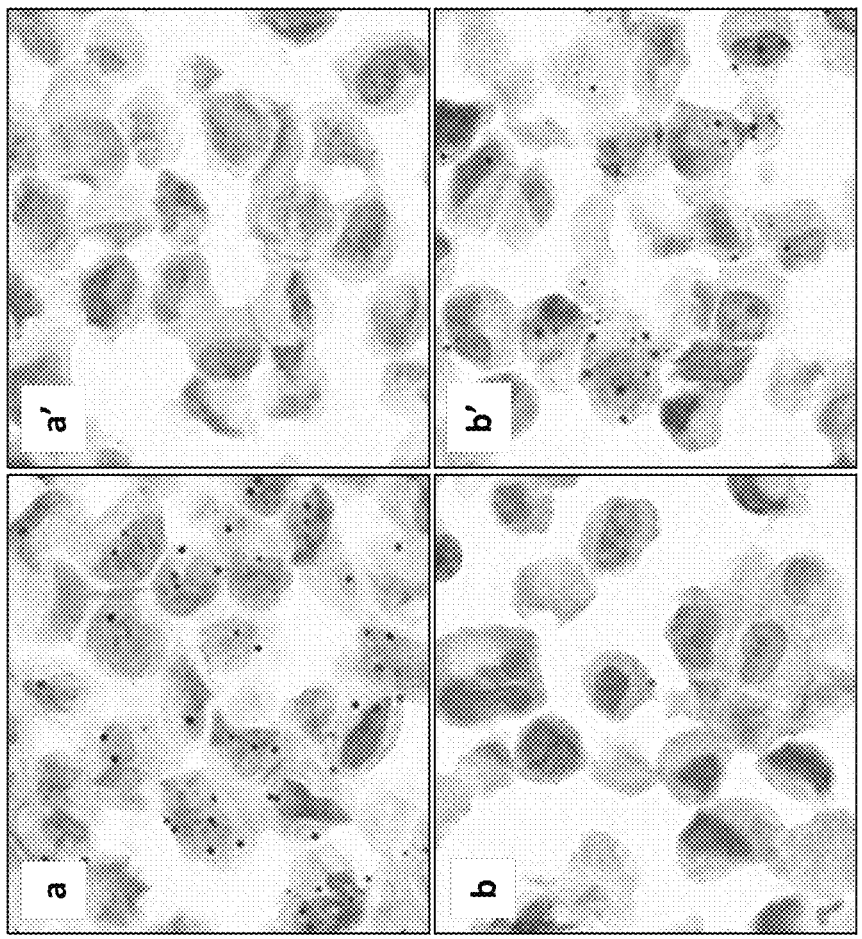

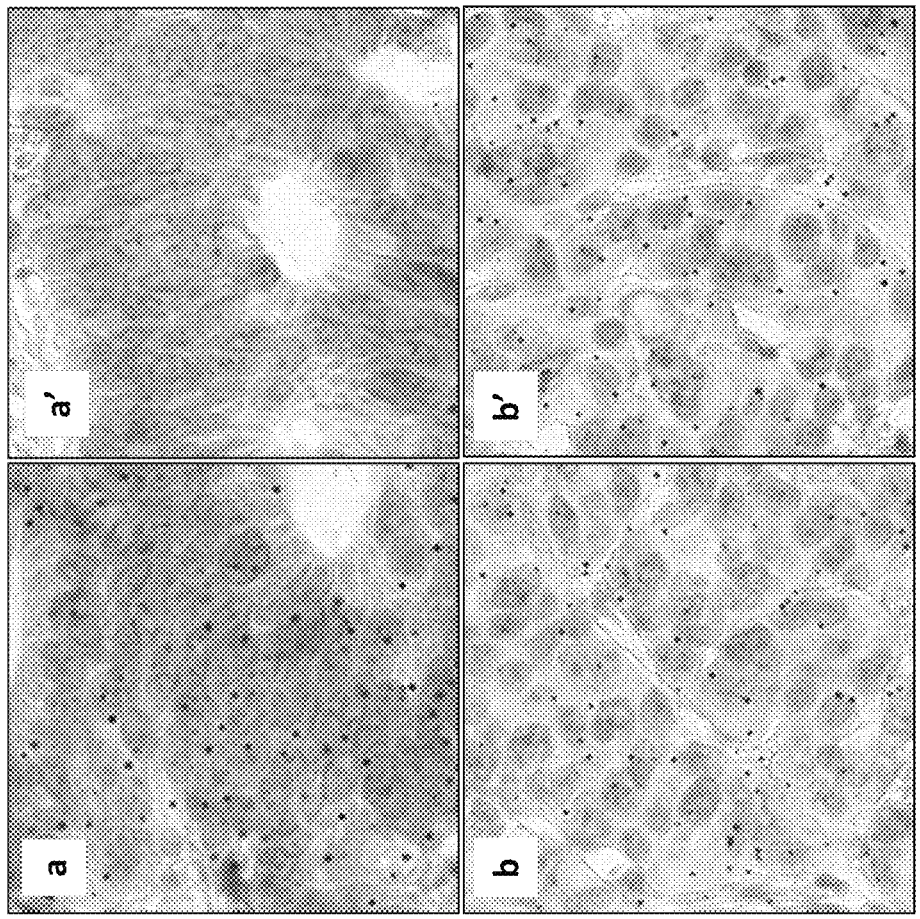

IN SITU DETECTION OF NUCLEOTIDE VARIANTS IN HIGH NOISE SAMPLES, AND COMPOSITIONS AND METHODS RELATED THERETO

CROSS-REFERENCE TO RELATED APPLICATIONS

This application claims the benefit of U.S. Provisional Application No. 62/240,347, filed Oct. 12, 2015, the entire contents of which are incorporated herein by reference.

INCORPORATION BY REFERENCE OF MATERIAL SUBMITTED ELECTRONICALLY

Incorporated by reference in its entirety herein is a computer-readable nucleotide sequence listing submitted concurrently herewith and identified as follows: One 887 Byte ASCII (Text) file named "2020-08-24_38632-202_SQL_ST25" created on Aug. 24, 2020.

FIELD OF THE INVENTION

The present invention relates generally to detection of nucleic acids, and more specifically to in situ detection of nucleic acid variants.

BACKGROUND OF THE INVENTION

Recent studies revealed significant heterogeneity in tumor cells previously regarded as clones of each other (Gerlinger et al., N. Engl. J. Med. 366:883-892, 2012), meaning individual cancer cells in a tumor site or tumor biopsy are not homogenous. In particular, neighboring cancer cells often have single nucleotide variations (SNVs) in DNA or RNA. Precision medicine thus demands in situ detection of SNV in tissue biopsies, in which the cellular structure and contents have to be substantially preserved through the assay. The complex physiochemical structures in cells and overwhelming amount of non-target nucleic acids and other molecules present a "high noise" environment, which can result in high background and which requires a combination of high specificity and high sensitivity that has not been achieved by existing in situ nucleic acid detection techniques.

SNV detection requires a single set of target probes (TPs) to capture a single signal-generating complex (SGC). In the previously described "double-Z" probe design disclosed in U.S. Pat. Nos. 7,709,198 and 8,658,361, however, multiple sets of TPs are hybridized to the target to provide sufficient number of SGCs for generating a detectable signal.

Thus, there exists a need for methods to detect single nucleotide variations or other nucleic acid variations at the single cell level in situ. The present invention satisfies this need, and provides related advantages as well.

SUMMARY OF INVENTION

The invention relates to methods of in situ detection of a nucleic acid variation of a target nucleic acid in a sample, including single nucleotide variations or splice variants, and the like. The method can comprise the steps of contacting the sample with a probe that detects the nucleic acid variation and a neighbor probe; contacting the sample with pre-amplifiers that bind to the nucleic acid variation probe and neighbor probe, respectively; contacting the sample with a collaboration amplifier that binds to the pre-amplifiers; and contacting the sample with a label probe system, wherein hybridization of the components forms a signal generating complex (SGC) comprising a target nucleic acid with the nucleic acid variation, the probes and amplifiers; and detecting in situ signal from the SGC on the sample. The invention also provides samples, tissue slides, and kits relating to detection of nucleic acid variations of a target nucleic acid.

BRIEF DESCRIPTION OF THE DRAWINGS

FIGS. 2A and 2B show in detail the configuration, position and orientation of SP and NP. FIG. 2A shows that SP comprises a target anchor segment (SPAT) complementary to the target sequence containing the SNV, a pre-amplifier anchor segment (SPAP) complementary to a segment on the SP pre-amplifier (SPM); NP comprises a target anchor segment (NPAT) complementary to the target sequence adjacent to the segment on the target that contains the SNV, a pre-amplifier anchor segment (NPAP) complementary to a segment on the NP pre-amplifier (NPM); and an optional spacer between SPAT and SPAP or between NPAT and NPAP. FIG. 2B illustrates examples of different orientations of SP and NP with respect to the target and the entire signal generating complex (SGC).

FIGS. 3A and 3B show two examples of different orientations or positions of SPM and NPM with respect to the SPAP and NPAP. The configuration shown in FIG. 3C is the same as that shown in FIG. 3B, where FIG. 3C reflects the flexibility of nucleic acid molecules and the ability of the configuration in FIG. 3B to provide NPCAs and SPCAs near each other for binding to a COM.

FIGS. 4A, 4B and 4C show different orientations of COM binding sites in collaborative hybridization. FIGS. 4A, 4B and 4C show exemplary configurations where a collaboration amplifier (COM) is hybridized simultaneously to an SP collaboration anchor (SPCA) on SPM and an NP collaboration anchor (NPCA) on NPM. FIGS. 4A and 4B depict the two corresponding segments on COM hybridized to SPCA and NPCA in the same orientation. The configuration depicted in FIG. 4B can be regarded as a special case of that in FIG. 4A. In FIG. 4B, the SPCA and NPCA are positioned with an offset. As a result, the spacer between the two corresponding segments on COM can be shortened or even removed, which can enhance the collaborative hybridization effect. FIG. 4C depicts the two corresponding segments on COM hybridized to SPCA and NPCA in the reverse orientation.

FIG. 5A depicts both SGCs formed and binding to a target nucleic acid. FIG. 5B depicts the binding of one SGC, whereas the second SGC is not bound. The lack of binding of the second SGC can be due to an issue with probe access or target nucleic acid degradation. In the depicted configuration, detectable signal is still generated with one SGC bound to the target nucleic acid.

FIG. 6A shows an embodiment in which the SPM and COM are integrated, and the NPM and COM are integrated. In the depicted embodiment, the SPM is integrated with a COM and the NPM is integrated with a COM using a "branched" molecule. FIG. 6B shows an embodiment in which the SP is integrated with the SPM, the NP is integrated with the NPM, and the COM is integrated with the LM.

FIG. 7A shows an SGC formed with collaborative hybridization between the COM and LM. FIG. 7B shows an SGC formed with collaborative hybridization between the LM and LP.

FIG. 8A shows a first collaborative hybridization between SPM or NPM and the SP and TP, respectively. A second collaborative hybridization is shown between the SPM, NPM and COMs. FIG. 8B shows a first collaborative hybridization between SP, NP and the target nucleic acid, and a second collaborative hybridization between SPM, NPM and COMs.

FIGS. 9A-9C show exemplary embodiments of detecting a specific splice junction in a target nucleic acid sequence. FIG. 9A shows an exemplary embodiment, where the SPAT hybridizes across the splice junction, that is, it hybridizes to both nucleic acid segments brought together at the splice junction, and the NPAT hybridizes to one of the nucleic acid segments. FIG. 9B shows an exemplary embodiment, where the SPAT hybridizes to one of the nucleic acid segments brought together at the splice junction, and the NPAT hybridizes to the other nucleic acid segment at the splice junction. FIG. 9C shows a configuration similar to that depicted in FIG. 9B with respect to hybridization of SPAT and NPAT to respective nucleic acid segments brought together at the splice junction, where there is also hybridization between complementary sections of the NPAT and SPAT.

FIG. 10A shows an exemplary embodiment of RNA specific detection using an exon junction bridging target probe. FIG. 10B shows an exemplary embodiment of RNA specific detection using a target probe set (nucleic acid variation probe and neighbor probe) that collaboratively hybridize to each other. FIG. 10C shows exemplary embodiments of RNA specific detection using a target probe set (nucleic acid variation probe and neighbor probe).

FIG. 12A shows a "pooling" approach where each target has unique SPAT and NPAT in the SP-NP pair but the other elements are the same in the rest of the SGC. A common signal is detected when any one of the target nucleic acids is present. FIG. 12B shows a "multiplexing" approach where each target nucleic acid has a unique SGC, which provides uniquely identifiable signals for each target nucleic acid.

FIGS. 13A-13D show the detection of BRAF V660E in sections of formalin fixed and paraffin embedded (FFPE) pellet of melanoma cell lines. Melanoma cell lines negative (CHL-1, a and a', FIGS. 13A and 13B) and positive (SK-MEL-28, b and b', FIGS. 13C and 13D) for the V600E point mutation of BRAF were assayed. Cells were hybridized to a target probe system (TPS) containing the wild type detection probe (WDP) (a and b, FIGS. 13A and 13C) and a TPS containing a BRAF V600E mutation detection probe (MDP) (a' and b', FIGS. 13B and 13D) separately.

FIG. 14A shows a high number of false positives with the use of a long SPAT. FIG. 14B shows that the assay has low sensitivity if the SPAT is too short.

FIG. 15A shows staining results with normal bases in SPAT. FIG. 15B shows improved results with modified bases used in SPAT.

FIGS. 16A-16D show detection of BRAF V600E in FFPE colon cancer tissues known to be negative (a and a', FIGS. 16A and 16B) and positive (b and b', FIGS. 16C and 16D) for the V600E point mutation. While signals were observed in both samples with probe targeting wild type BRAF mRNA (a and b, FIGS. 16A and 16C), V600E mutation mRNA was detected only in the mutation positive sample with probe designed specifically for V600E mutation (b', FIG. 16D).

FIG. 17A shows low staining of HGF target RNA, which is known to be very low abundant and partially degraded in the sample using RNA detection methods as previously described in U.S. Pat. Nos. 7,709,198 and 8,658,361. FIG. 17B shows improved staining of the same target using a configuration similar to that shown in FIG. 11A.

FIG. 18 shows enhanced sensitivity of an exemplary method of the invention in detecting very short sequences compared to methods disclosed in U.S. Pat. Nos. 7,709,198 and 8,658,361.

DETAILED DESCRIPTION OF THE INVENTION

Figure 1:
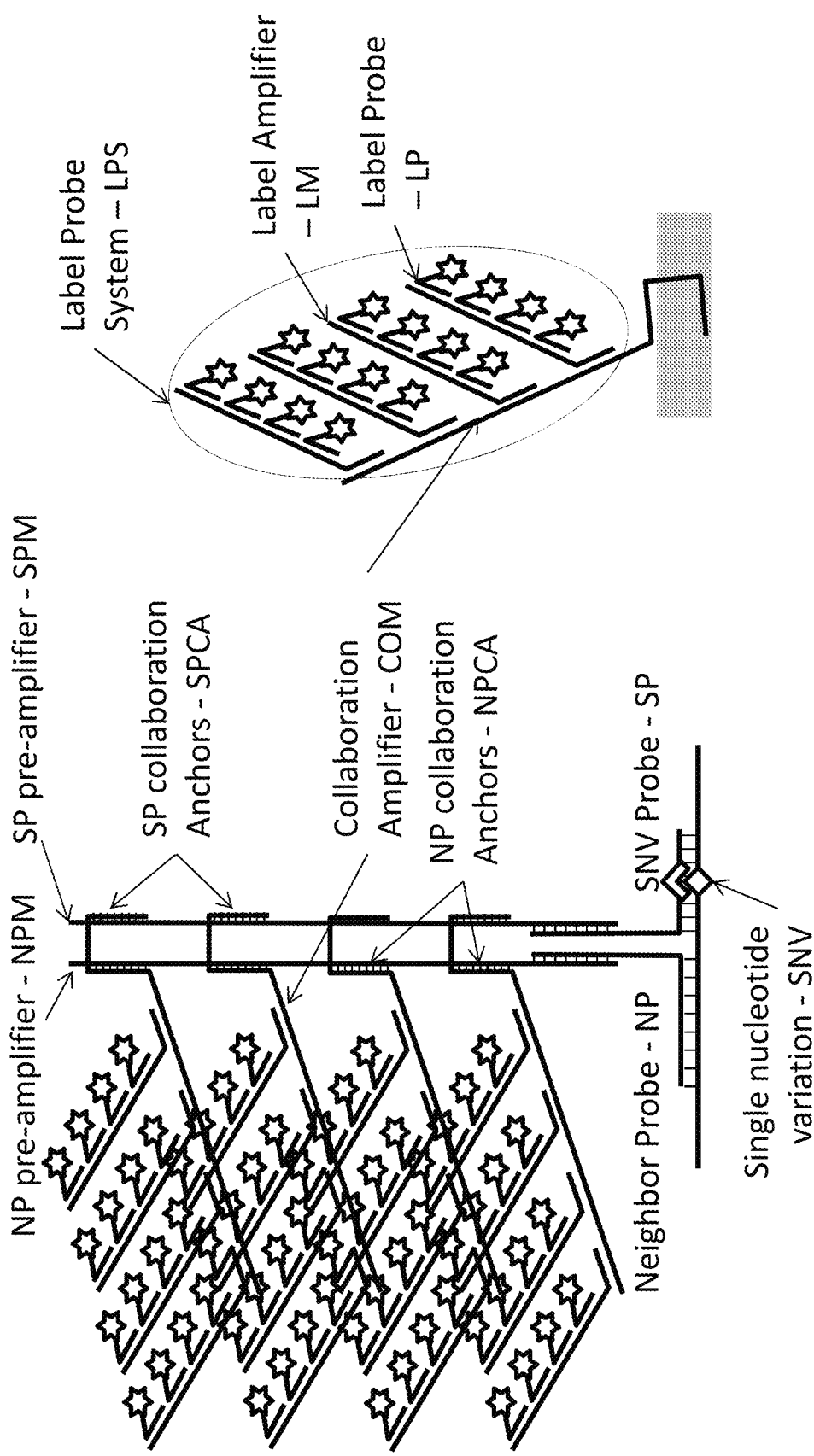
FIG. 1 shows an exemplary configuration of a signal-generating complex (SGC) for in situ detection of a single nucleotide variation (SNV) in a target nucleic acid. The SGC comprises single nucleotide variation probe—SP; neighbor probe—NP; SP pre-amplifier—SPM, which contains multiple SP collaboration anchors—SPCA; NP pre-amplifier—NPM, which contains multiple NP collaboration anchors—NPCA; collaboration amplifier—COM; label probe system—LPS, which can comprise a plurality of label amplifiers—LM and each of which in turn can bind to a plurality of label probes—LP.

The present invention relates to methods that provide for high sensitivity detection of nucleic acid variants in a cell. The methods are useful for detecting nucleic acid variations that can have clinical implications for disease status, disease progression, response to treatment of a disease, and the like.

For example, cancers, including tumors, are not homogeneous but rather can contain various types of cells and/or cells of the same type but having different expression levels of proteins and nucleic acids between the cells. In some cases, there exist nucleic acid variations between the cells. Such nucleic acid variations can include, but are not limited to, single nucleotide variations, insertions and/or deletions (indels), splice variations, gene rearrangements, and the like. The methods and compositions of the invention, as disclosed herein, can be used to detect nucleic acid variants at the single cell level. Thus, the methods provide a highly sensitive and specific assay system to detect nucleic acid variations in clinical specimens, providing more detailed visualizable and clinically relevant information on the expression of nucleic acid variations at the single cell level.

As described below in more detail, a probe is designed to detect nucleic acid variants, such as single nucleotide variations, insertions and/or deletions, splice sites, gene rearrangements, and the like, and such a probe is referred to herein as an SP. In embodiments of the invention, the SP can be a single nucleotide variant (SNV) probe, which can detect a single nucleotide variation in a target nucleic acid, or more generally a probe which can detect a specific nucleic acid variant that involves more than one nucleotide, that is, a multi-nucleotide variant. Such multi-nucleotide variants would include a micro-insertion, micro-deletion, or modification of more than one nucleotide using methods such as CRISPER. In particular, a splice site or junction in a target nucleic acid can be regarded as a special type of multi-nucleotide variant because this junction is specifically related to the nucleotides on each side of the junction. It is understood that the description of an SP herein or depiction in a figure of an SP herein can be applied to any type of SP, with the SP designed to detect the SNV or multi-nucleotide variants such as a splice site. Thus, a description herein or a configuration in a figure depicting the detection of an SNV using an SP can be applied similarly to detection of multi-nucleotide variants including a splice site, or other variant, with the SP designed to detect a multi-nucleotide variant rather than an SNV, with the remainder of the depicted configuration being applicable to detection of the multi-nucleotide variant in a target nucleic acid. Similarly, a description herein or a depiction in a figure of detection of a splice site can be applied to detection of SNV or multi-nucleotide variant, with the difference being whether the SP is designed to detect an SNV or multi-nucleotide variant such as a splice site in a target nucleic acid. Thus, the description herein of an SP is understood to apply to the detection of nucleotide variants in a target nucleic acid, depending on the nature of the target nucleic acid.

The present invention provides a highly sensitive and specific in situ detection of nucleic acid variations in a high noise environment, for example, tumor biopsies. In one embodiment, the nucleic acid variation is a single nucleotide variation (SNV). An exemplary embodiment of the invention is shown in FIG. 1 and described below in more detail.

(1) SNV Probe (SP).

Figure 2B:
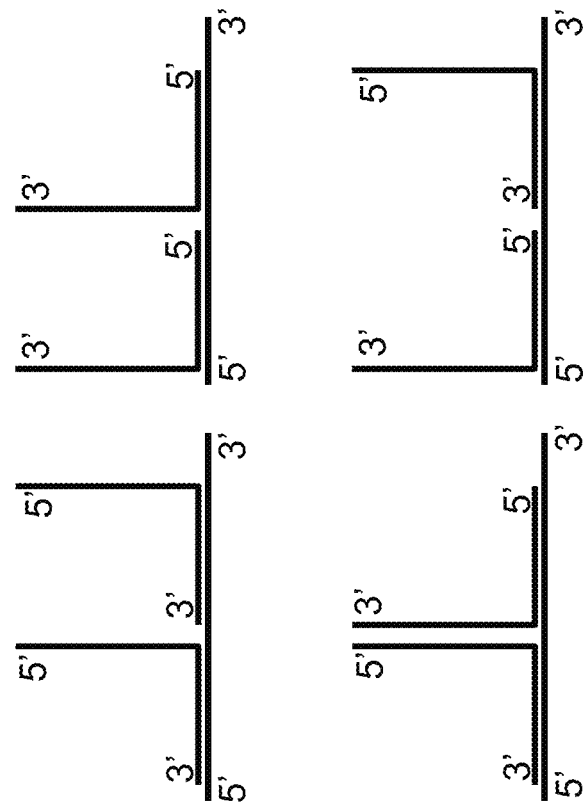
FIGS. 2A and 2B exemplify detail and orientations of SP and NP.
Figure 2A:
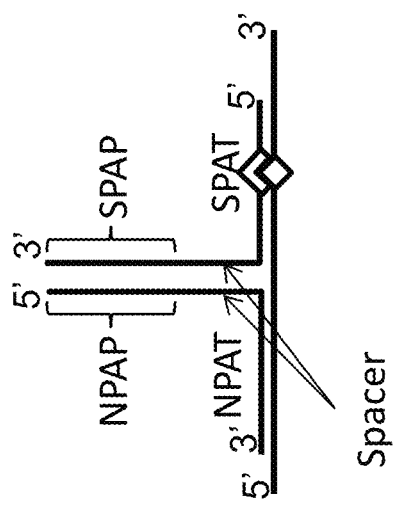

As shown in FIG. 1 and in detail in FIG. 2A, a single nucleotide variation (SNV) probe (SP) comprises two non-overlapping regions, a target anchor segment (SPAT) and a pre-amplifier anchor segment (SPAP), optionally separated by a spacer or linker sequence. An SPAT is complementary to a target nucleic acid sequence encompassing the SNV site and has sufficient discriminating power to distinguish a single base change in the SNV sequence. Its length and other parameters are designed to hybridize to targeted SNV but not to the wild type or non-targeted SNV sequences. An SPAT is generally between about 10 to 20 nucleotides in length, while an SPAP is generally between about 14 to 28 nucleotides in length. The SP probe design can be readily extended to detect insertions and deletions (indels) of 1-10,000 bases.

(2) Neighbor Probe (NP).

Also shown in FIG. 1 and in detail in FIG. 2A, a neighbor probe (NP) comprises two non-overlapping regions, a target anchor segment (NPAT) and a pre-amplifier anchor segment (NPAP), optionally separated by a spacer or linker sequence. An NPAT is complementary to a region of the target nucleic acid that is adjacent to the SNV and is generally between about 12 to 40 nucleotides in length. An NPAP is generally between about 14 to 28 nucleotides in length.

The NP can sit left or right (5' or 3') to the SP bound to the target SNV. In another embodiment, the NP and SP can assume different 5' and 3' orientations in relationship to each other and in relationship to the signal generating complex (SGC), as illustrated in FIG. 2. For example, as shown in FIG. 2B, the NP can have the NPAT on the 3' and the SP can have the SPAT on the 3' end (FIG. 2B, upper left), the NP can have the NPAT on the 5' end and the SP can have the SPAT on the 5' end (FIG. 2B, upper right), the NP can have the NPAT on the 3' end and the SP can have the SPAT on the 5' end (FIG. 2B, lower left), or the NP can have the NPAT on the 5' end and the SP can have the SPAT on the 3' end (FIG. 2B, lower right). It is possible to further enhance the specificity or sensitivity of mutation detection by incorporating multiple NPs in the adjacent region of the SNV. In one embodiment, two NPs sitting left and right (5' or 3', that is, flanking) to the SP bound to the target SNV can be used to capture one or multiple SGCs and generate a detectable signal (see FIG. 5A, showing two NPs flanking the SP).

Figure 8B:
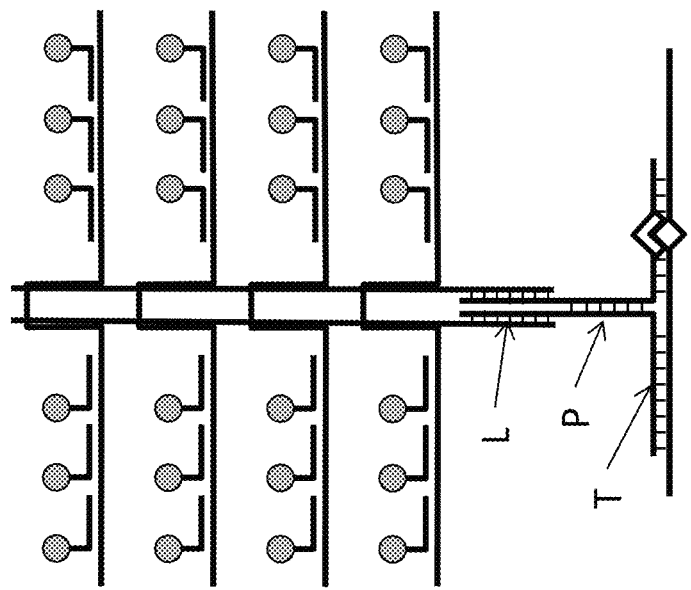
FIGS. 8A and 8B show an exemplary embodiment incorporating more than one collaborative hybridization steps in the assembly of the SGC during the assay.

The NP can bind stably to its complementary regions of the target nucleic acid under the hybridization conditions employed. On the other hand, the SPAT of SP is generally short (10-20 nucleotides) in order to enhance its power to discriminate SNV against non-SNV sequence. In one embodiment, SPAT is shorter than NPAT or the melting temperature of SPAT is lower than NPAT. A short SP can still hybridize to the target nucleic acid containing the SNV at the presence of NP due to the collaborative hybridization effect, that is, the melting temperature of the target nucleic acid hybridizing to SP and NP simultaneously is higher than the melting temperature of the target nucleic acid hybridizing to SP or NP alone. The collaborative hybridization effect can be enhanced by target probe set configurations depicted in FIGS. 5 and 8, where in FIG. 5A, the SP is flanked by two NPs on both sides. In FIG. 8B, both SP and NP have a third non-overlapping segment, that are complementary to each other. In these cases, the melting temperature of the target nucleic acid hybridizing to SP and NP simultaneously is substantially higher than the melting temperature of the target nucleic acid hybridizing to SP or NP alone. A detectable signal is generated when SP and NP are hybridized to adjacent regions of a single target nucleic acid, whereas there is only weak or undetectable signal when SP and NP are not hybridizing to adjacent regions of a single target nucleic acid.

(3) Pre-Amplifier for SP (SPM).

Figures 3A, 3B, 3C:
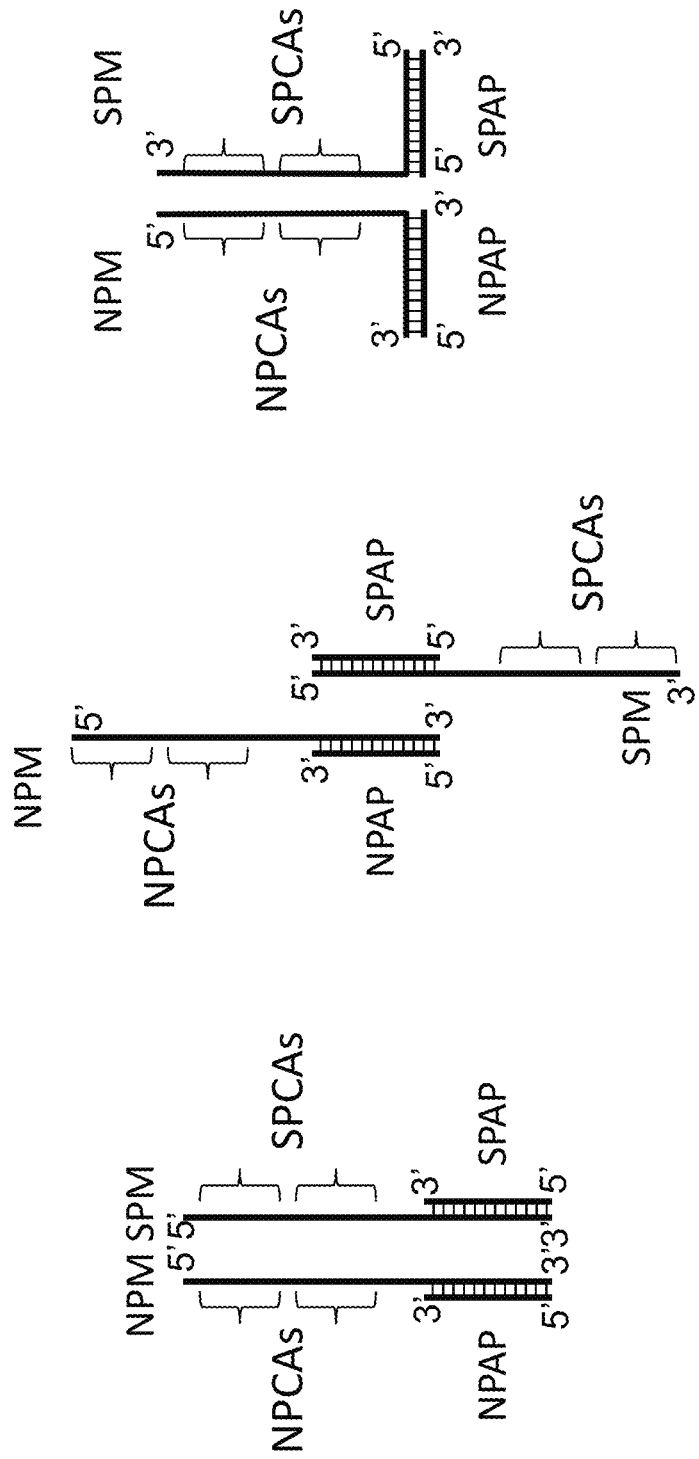
FIGS. 3A-3C show different orientations or positions of SPM and NPM.

As shown in FIG. 1 and in detail in FIG. 3, a pre-amplifier for SP (SPM) comprises a single stranded nucleic acid of between about 50 and 500 nucleotides in length. The SPM comprises a plurality of repeat sequences between 10 and 20 nucleotides in length called an SP collaboration anchor (SPCA). SPM is linked to SP by hybridization. SPM comprises a segment complementary to the pre-amplifier anchor segment of SP (SPAP), which is designed to bind to SPAP in different positions or orientations as shown in FIG. 3. In a preferred embodiment, SPCA is repeated between 2 and 20 times in the SPM.

(4) Pre-Amplifier for NP (NPM).

As shown in FIG. 1 and in detail in FIG. 3, a pre-amplifier for NP (NPM) comprises a single stranded nucleic acid of between about 50 and 500 nucleotides in length. The NPM comprises a plurality of repeat sequence between 10 and 20 nucleotides in length called an NP collaboration anchor (NPCA). NPM is linked to NP by hybridization. NPM comprises a segment complementary to the pre-amplifier anchor segment of NP (NPAP), which is designed to bind to NPAP in different positions or orientations as shown in FIG. 3. In a preferred embodiment, NPCA is repeated between 2 and 20 times in the NPM.

(5) Collaboration Amplifier (COM).

A collaboration amplifier (COM) comprises a single stranded nucleic acid of between about 60 and 900 nucleotides in length. As shown in FIG. 1 and in more detail in FIG. 4, the COM comprises three non-overlapping segments, a segment complementary to the SP collaboration anchor (SPCA) of the SP pre-amplifier (SPM), a segment complementary to the NP collaboration anchor (NPCA) of the NP pre-amplifier (NPM), and a segment containing repeated sections, each of which can hybridize to a Label Probe System (LPS) that gives out signal for detection. The SPCA and NPCA hybridize to COM in collaboration, that is, the melting temperature of COM hybridizing to SPCA and NPCA simultaneously is significantly higher than the melting temperature of COM hybridizing to SPCA or NPCA alone. That is, the hybridization condition employed in the assay is set as that a COM cannot bind stably to either SPCA or NPCA alone. Since SPM and NPM binds stably to SP and NP, respectively, COMs can stably bind to the target sequence when and only when both SP and NP are hybridized to the target nucleic acid and adjacent to each other. Since it is extremely unlikely that such a unique configuration and positioning will occur non-specifically, this collaboration hybridization significantly reduces false positive signal caused by non-specific binding of NPM or SPM in a high noise environment. The two segments complementary to SPCA and NPCA can hybridize to them in different orientations, as depicted in FIG. 4. The segment of the COM that hybridizes to the LPS generally comprises a plurality of repeat sequences between about 15 and 30 nucleotides in length, referred to as label amplifier anchor segments, that are capable of hybridizing to the LPS. In addition, the label amplifier anchor segments can be located on either side or both sides of the segments complementary to SPCA and NPCA.

(6) Label Probe System (LPS).

As shown in FIG. 1, a label probe system (LPS) hybridizes to COM. The label probe system (LPS) comprises a plurality of amplifiers, which are nucleic acids comprising a segment that can hybridize to complementary repeat sequences of the COM. The amplifier also comprises a plurality of repeat sequences that can hybridize to a label probe (LP). The label probe comprises a nucleic acid comprising a segment that can hybridize to complementary repeat sequences of the amplifier. The label probe also comprises a detectable label. The label probe system thus provides a plurality of label probes bound to amplifiers, and a plurality of amplifiers can bind to a COM.

In more detail, an LPS comprises a plurality of label amplifiers (LMs) and a plurality of label probes (LPs), wherein each LM comprises a segment that can bind to a label amplifier anchor segment of the COM. The LM also comprises a plurality of label probe anchor segments. Each LP comprises a detectable label and a segment that hybridizes to the label probe anchor segment of the LM. When hybridizations occur between the components, a signal generating complex (SGC) is formed. The SGC comprises a target nucleic acid with the single nucleotide variation, an SP, an NP, an SPM, an NPM, a plurality of COMs, a plurality of LMs, and a plurality of LPs (see FIG. 1).

The invention provides an assay of high specificity and sensitivity such that in situ detection of nucleic acid variations, including SNV, multi-nucleotide variants such as splice sites, and other variants, can be performed in high noise samples. As illustrated in FIG. 1, an SGC provides for very sensitive and specific detection of an SNV in a target nucleic acid. As further illustrated in FIG. 1, a false signal can be generated if a COM with LPS hybridized to it binds non-specifically to a component of the cell. However, the nature of the collaborative hybridization of the invention, as described herein, provides high sensitivity and specificity because the signal generated when bound to the actual target is greater than the signal of COM bound non-specifically. As described above, the SPCA is repeated at least 2 times in the SPM, and the NPCA is repeated at least 2 times in the NPM. Such a configuration provides for a detectable signal of the actual target that is at least 2 times greater than that of a COM bound non-specifically. The differential signal between COM-LPS bound to the actual target can be increased further, as described herein, by increasing the number of SPCA repeats in the SPM and the number of NPCA repeats in the NPM (see also FIG. 1). In general, the number of SPCA repeats in the SPM will be the same as the number of NPCA repeats in the NPM, so that the COM can hybridize collaboratively to both the SPM and NPM. Therefore, the differential signal between binding of LPS to the actual target compared to non-specific binding can be increased to provide a greater enhancement of signal to noise ratio, thereby providing a higher specificity and higher sensitivity method to detect single nucleotide variations in individual cells in situ.

In one embodiment, the invention provides a method of in situ detection of nucleic acid variations, for example, a single nucleotide variation, of a target nucleic acid. In an embodiment of the invention, provided is a method of in situ detection of a single nucleotide variation of a target nucleic acid in a sample of fixed and permeabilized cells. The method can comprise the steps of: (A) contacting the sample with a single nucleotide variation probe (SP) and a neighbor probe (NP), wherein the SP comprises a target anchor segment (SPAT) that can specifically hybridize to a region of the target nucleic acid comprising the single nucleotide variation and a pre-amplifier anchor segment (SPAP), and wherein the NP comprises a target anchor segment (NPAT) that can hybridize to a region of the target nucleic acid adjacent to the binding site of the SP and a pre-amplifier anchor segment (NPAP); (B) contacting the sample with an SP pre-amplifier (SPM) and an NP pre-amplifier (NPM), wherein the SPM comprises a segment that can bind to the SP and comprises two or more SP collaboration anchors (SPCAs), and wherein the NPM comprises a segment that can bind to the NP and comprises two or more NP collaboration anchors (NPCAs); (C) contacting the sample with a collaboration amplifier (COM), wherein the COM comprises a first segment complementary to the SPCA, a second segment complementary to the NPCA, and a third segment comprising a plurality of label amplifier anchor segments; (D) contacting the sample with a label probe system (LPS), wherein the LPS comprises a plurality of label amplifiers (LMs) and a plurality of label probes (LPs), wherein each LM comprises a segment that can bind to a label amplifier anchor segment of the COM and a plurality of label probe anchor segments, wherein each LP comprises a detectable label and a segment that hybridizes to the label probe anchor segment of LM, wherein the aforesaid hybridizations form a signal generating complex (SGC) comprising a target nucleic acid with the single nucleotide variation, an SP, an NP, an SPM, an NPM, a plurality of COMs, a plurality of LMs, and a plurality of LPs; and (E) detecting in situ signal from the SGC on the sample.

As described herein, the methods of the invention generally relate to in situ detection of nucleic acid variations. Methods for in situ detection of nucleic acids are well known to those skilled in the art (see, for example, US 2008/0038725; US 2009/0081688; Hicks et al., *J. Mol. Histol.* 35:595-601 (2004)). As used herein, "in situ hybridization" or "ISH" refers to a type of hybridization that uses a directly or indirectly labeled complementary DNA or RNA strand, such as a probe, to bind to and localize a specific nucleic acid, such as DNA or RNA, in a sample, in particular a portion or section of tissue (in situ). The probe types can be double stranded DNA (dsDNA), single stranded DNA (ssDNA), single stranded complimentary RNA (sscRNA), messenger RNA (mRNA), micro RNA (miRNA), ribosomal RNA, mitochondrial RNA, and/or synthetic oligonucleotides. The term "fluorescent in situ hybridization" or "FISH" refers to a type of ISH utilizing a fluorescent label. The term "chromogenic in situ hybridization" or "CISH" refers to a type of ISH with a chromogenic label. ISH, FISH and CISH methods are well known to those skilled in the art (see, for example, Stoler, *Clinics in Laboratory Medicine* 10(1):215-236 (1990); *In situ hybridization. A practical approach*, Wilkinson, ed., IRL Press, Oxford (1992); Schwarzacher and Heslop-Harrison, *Practical in situ hybridization*, BIOS Scientific Publishers Ltd, Oxford (2000)).

For in situ detection of nucleic acid targets in a cell, the cell is optionally fixed and permeabilized before hybridization of the target probes. Fixing and permeabilizing cells can facilitate retaining the nucleic acid targets in the cell and permit the target probes, label probes, amplifiers, preamplifiers, and so forth, to enter the cell. The cell is optionally washed to remove materials not captured to a nucleic acid target. The cell can be washed after any of various steps, for example, after hybridization of the target probes to the nucleic acid targets to remove unbound target probes, after hybridization of the preamplifiers, amplifiers, and/or label probes to the target probes, and/or the like. Methods for fixing and permeabilizing cells for in situ detection of nucleic acids, as well as methods for hybridizing, washing and detecting target nucleic acids, are also well known in the art (see, for example, US 2008/0038725; US 2009/0081688; Hicks et al., *J. Mol. Histol.* 35:595-601 (2004); Stoler, *Clinics in Laboratory Medicine* 10(1):215-236 (1990); *In situ hybridization. A practical approach*, Wilkinson, ed., IRL Press, Oxford (1992); Schwarzacher and Heslop-Harrison, *Practical in situ hybridization*, BIOS Scientific Publishers Ltd, Oxford (2000)).

As used herein, the term "plurality" is understood to mean two or more. Thus, a plurality can refer to, for example, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 55 or more, 60 or more, 65 or more, 70 or more, 75 or more, 80 or more, 85 or more, 90 or more, 95 or more, 100 or more, 110 or more, 120 or more, 130 or more, 140 or more, 150 or more, 160 or more, 170 or more, 180 or more, 190 or more, 200 or more, 300 or more, 400 or more, 500 or more, 600 or more, 700 or more, 800 or more, 900 or more, or 1000 or more, or even a greater number, if desired for a particular use.

In one embodiment of the invention, the methods can be used to detect a single nucleotide variation of a target nucleic acid. Such a single nucleotide variation (SNV) can be a point mutation or a single-nucleotide polymorphism (SNP). In an embodiment of a method of the invention, a sample containing cells is contacted with a single nucleotide variation probe (SP) and a neighbor probe (NP). The SP comprises a target anchor segment (SPAT) that can specifically hybridize to a region of the target nucleic acid comprising the single nucleotide variation. As used herein, an SP that can "specifically hybridize" to a region of the target nucleic acid comprising the SNV refers to an SP that can specifically hybridize to a target nucleic acid that contains the SNV but not to a nucleic acid having a different nucleotide at the position of the SNV. Thus, an SP can distinguish between a nucleic acid that contains the SNV and a nucleic acid that does not contain the SNV. It is understood that an SP used in the methods and compositions of the invention is designed such that, under the assay conditions utilized, the SP can specifically hybridize to a target nucleic acid containing a specific nucleotide, such as the SNV, but will not hybridize to a nucleic acid sequence containing a different nucleotide at that position, for example, a wild type nucleic acid sequence. Thus, an SP is selected to have an SPAT of a desired length suitable for exhibiting specific hybridization to the target nucleic acid containing the SNV under the temperature and buffers used for the in situ hybridization assay. The length of the SPAT can be chosen to be sufficiently short in length such that it will not remain stably bound to the target nucleic acid in the absence of binding of the NP. In general, the SPAT is relatively short in length, for example, about 10 to 20 nucleotides in length, but can be somewhat shorter or longer depending on the assay conditions used, such as about 9 to 21 nucleotides in length. Thus, in general, an SPAT can be 9, 10, 11, 12, 13, 14, 15, 16, 17, 18, 19, 20 or 21 nucleotides in length.

In the SP, the base complementary to the nucleotide variation on the target nucleic acid can be anywhere within the SPAT of the SP but is generally near the center of the SPAT. It is important that the SP be able to discriminate between the target nucleic acid having the nucleotide variation and a wild-type or other sequence that does not contain the nucleotide variation. The SP should provide good sensitivity and specificity. To achieve this, the melting temperature difference between binding of the SP to a nucleic acid having the nucleotide variation and to a wild-type or other sequence that does not contain the nucleotide variation ("$dT_m$") should be maximized. The position of the base within SPAT that is complementary to the nucleotide variation can be selected to maximize $dT_m$. This can be done by using melting temperature calculation algorithms known in the art (see, for example, SantaLucia, *Proc. Natl. Acad. Sci. U.S.A.* 95:1460-1465 (1998)). In addition, artificial modified bases such as Locked Nucleic Acid (LNA) or bridged nucleic acid (BNA) and naturally occurring 2'-O-methyl RNA are known to enhance the binding strength between complementary pairs (Petersen and Wengel, *Trends Biotechnol.* 21:74-81 (2003); Majlessi et al., *Nucl. Acids Res.* 26:2224-2229 (1998)). These modified bases can be strategically introduced into the SPAT of the SP to further increase the $dT_m$ to enhance the detection sensitivity and specificity of SP.

One approach is to make all bases in the SPAT of the SP with modified nucleotides (LNA, BNA or 2'-O-methyl RNA). Because each modified base can increase the melting temperature, the length of SPAT can be substantially shortened, which makes the SP more sensitive to a single base difference. Alternatively, only the base complementary to the nucleotide variation in the target nucleic acid is changed to the modified nucleotide. Because the binding strength of a modified base to its complement is stronger, the difference in melting temperatures ($dT_m$) is increased between the binding of SP to the nucleotide variation in the target nucleic acid and the wild type or sequence that does not contain the nucleotide variation. Yet another embodiment is to use three modified bases (for example, three LNA, BNA or 2'-O-methyl RNA bases, or a combination of two or three different modified bases) in the SPAT centered around the base complementary to the nucleotide variation in the target nucleic acid.

An SP also comprises a pre-amplifier anchor segment (SPAP). The SPAP is complementary to a segment of the SP pre-amplifier (SPM) and provides for binding of the SPM to the SP bound to the target nucleic acid. The SPAP is of a length that provides stable hybridization between the SP and SPM under the assay conditions used. Thus, the SPAP is generally longer than the SPAT, for example, about 14 to 28 nucleotides in length, but can be somewhat shorter or longer depending on the assay conditions used, such as about 10 to 30 nucleotides in length. Thus, in general, an SPAP can be 10, 11, 12, 13, 14, 15, 16, 17, 18, 19, 20, 21, 22, 23, 24, 25, 26, 27, 28, 29 or 30 nucleotides in length.

The SP can optionally include a spacer between the SPAT and the SPAP. Thus, it is understood that an SP can have no spacer between the SPAT and the SPAP. Generally, however, the SP will have a spacer between the SPAT and the SPAP. Such a configuration allows for a desired spatial separation of the target nucleic acid from the SGC formed. A spacer between the SPAT and the SPAP will generally be 1 to 10 nucleotides in length, but it is understood that the spacer can be longer, if desired. Thus, an optional spacer between the SPAT and the SPAP can be, for example, 1, 2, 3, 4, 5, 6, 7, 8, 9, or 10 nucleotides in length. In a particular embodiment, the spacer is 5 nucleotides in length.

In an embodiment of the invention, the sample is also contacted with a neighbor probe (NP). The NP comprises a target anchor segment (NPAT) that can hybridize to a region of the target nucleic acid adjacent to the binding site of the SP. The region of the target nucleic acid adjacent to the SPAT binding site can be immediately adjacent, that is, it can bind with no gap between the SPAT binding site and the NPAT binding site. However, generally, there will be a gap of 1 to a few nucleotides between the SPAT binding site and the NPAT binding site, for example a gap of 1 to 50 nucleotides, and such binding sites will still be considered as adjacent binding sites for the SP and NP binding to the target nucleic acid.

The NP is selected to have an NPAT of a desired length suitable for exhibiting specific hybridization to the target nucleic acid adjacent to the SPAT binding site under the temperature and buffers used for the in situ hybridization assay. Since the NP does not have to discriminate single nucleotide variation, the NPAT can be relatively longer than SPAT to provide stability, for example, about 16 to 30 nucleotides in length, but can be somewhat shorter or longer depending on the assay conditions used, such as about 12 to 40 nucleotides in length. Thus, in general, an NPAT can be 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

An NP also comprises a pre-amplifier anchor segment (NPAP). The NPAP is complementary to a segment of the NP pre-amplifier (NPM) and provides for binding of the NPM to the NP bound to the target nucleic acid. The NPAP is of a length that provides stable hybridization between the NP and NPM under the assay conditions used. Thus, the NPAP is generally about 14 to 28 nucleotides in length, but can be somewhat shorter or longer depending on the assay conditions used, such as about 10 to 30 nucleotides in length. Thus, in general, an NPAP can be 10, 11, 12, 13, 14, 15, 16, 17, 18, 19, 20, 21, 22, 23, 24, 25, 26, 27, 28, 29 or 30 nucleotides in length.

The NP can optionally include a spacer between the NPAT and the NPAP. Thus, it is understood that an NP can have no spacer between the NPAT and the NPAP. Generally, however, the NP will have a spacer between the NPAT and the NPAP. Such a configuration allows for a desired spatial separation of the target nucleic acid from the SGC formed. A spacer between the NPAT and the NPAP will generally be 1 to 10 nucleotides in length, but it is understood that the spacer can be longer, if desired. Thus, an optional spacer between the NPAT and the NPAP can be, for example, 1, 2, 3, 4, 5, 6, 7, 8, 9, or 10 nucleotides in length. In a particular embodiment, the spacer is 5 nucleotides in length.

In an embodiment of a method of the invention, the sample is contacted with an SP pre-amplifier (SPM) and an NP pre-amplifier (NPM). The SPM comprises a segment that can bind to the SP by way of the SPAP. Thus, the segment of the SPM is complementary to the SPAP of the SP. As disclosed herein, the SPAP is generally of a length that provides stable hybridization between the SP and SPM under the assay conditions used. Thus, the segment of the SPM that is complementary to the SPAP is generally about 14 to 28 nucleotides in length, but can be somewhat shorter or longer depending on the length of the SPAP and the assay conditions used, such as about 10 to 30 nucleotides in length. Thus, in general, the segment is complementary to the SPAP and can be 10, 11, 12, 13, 14, 15, 16, 17, 18, 19, 20, 21, 22, 23, 24, 25, 26, 27, 28, 29 or 30 nucleotides in length.

The SPM also comprises two or more SP collaboration anchors (SPCAs). The SPCA provides a binding site for a collaboration amplifier (COM). The length of the SPCA is generally chosen to be sufficiently short in length such that it will not remain stably bound to the COM in the absence of binding of the COM to the NPCA of the NPM (see FIG. 1). In general, the SPCA is relatively short in length, for example, about 10 to 20 nucleotides in length. Thus, in general, an SPCA can be 10, 11, 12, 13, 14, 15, 16, 17, 18, 19 or 20 nucleotides in length. In a particular embodiment, the SPCA is 14 nucleotides in length.

The NPM comprises a segment that can bind to the NP by way of the NPAP. Thus, the segment of the NPM is complementary to the NPAP of the NP. As disclosed herein, the NPAP is generally of a length that provides stable hybridization between the NP and NPM under the assay conditions used. Thus, the segment of the NPM that is complementary to the NPAP is generally about 14 to 28 nucleotides in length, but can be somewhat shorter or longer depending on the length of the NPAP and the assay conditions used, such as about 10 to 30 nucleotides in length. Thus, in general, the segment is complementary to the NPAP and can be 10, 11, 12, 13, 14, 15, 16, 17, 18, 19, 20, 21, 22, 23, 24, 25, 26, 27, 28, 29 or 30 nucleotides in length.

The NPM also comprises two or more NP collaboration anchors (NPCAs). The NPCA provides a binding site for a collaboration amplifier (COM). The length of the NPCA is generally chosen to be sufficiently short in length such that it will not remain stably bound to the COM in the absence of binding of the COM to the SPCA of the SPM (see FIG. 1). In general, the NPCA is relatively short in length, for example, about 10 to 20 nucleotides in length. Thus, in general, an NPCA can be 10, 11, 12, 13, 14, 15, 16, 17, 18, 19 or 20 nucleotides in length. In a particular embodiment, the NPCA is 14 nucleotides in length.

The SPM or NPM can optionally include a spacer between the SPCAs or NPCAs. Thus, it is understood that an SPM can have no spacer between the SPCAs, and an NPM can have no spacer between the NPCAs. Generally, however, the SPM and NPM will have a spacer between the SPCAs and NPCAs. An optional spacer between the SPCAs and NPCAs will generally be 1 to 10 nucleotides in length, but it is understood that the spacer can be longer, if desired. Thus, an optional spacer between the SPCAs and NPCAs can be independently, for example, 1, 2, 3, 4, 5, 6, 7, 8, 9, or 10 nucleotides in length. In a particular embodiment, the spacer is 5 nucleotides in length. It is understood that the use of a spacer between any SPCAs of an SPM and NPCAs of an NPM is independent, and the length of the spacer between the SPCAs and NPCAs is independent. For example, if an NPM contains 4 NPCAs, there would be 3 optional spacers, and those spacers do not have to be the same length as each other, that is, the lengths are independent.

As described herein, the SPM and NPM can be designed to contain two or more SPCAs and NPCAs, respectively. To increase the signal associated with an SGC, the number of SPCAs and NPCAs can be increased (see FIG. 1). The number of SPCAs and NPCAs can be selected to give a desired signal strength or increased signal to noise ratio. As shown in FIG. 1, each SPCA and NPCA can bind to a COM, which in turn binds to a label probe system (LPS). Increasing the number of SPCAs and NPCAs on the SPM and NPM, respectively, will result in a corresponding increase in the number of label probe systems (LPSs) bound to the target nucleic acid. Each COM that can bind to a nucleic acid target via collaboration hybridization in the methods of the invention increase the target-specific signal over non-specific binding of a COM to a component of the cell (see FIG. 1). The number of SPCAs and NPCAs in a SPM and NPM pair will generally be the same between the pair, will generally have the same spacing between the pairs, and will generally have 2 to 20 SPCAs and NPCAs per pair, although it is understood that a higher number can be used, if desired. Thus, an SPM and NPM will generally have 2, 3, 4, 5, 6, 7, 8, 9, 10, 11, 12, 13, 14, 15, 16, 17, 18, 19 or 20 SPCAs and NPCAs, respectively.

In an embodiment of a method of the invention, the sample is contacted with a collaboration amplifier (COM). The COM comprises a first segment complementary to the SPCA, a second segment complementary to the NPCA, and a third segment comprising a plurality of label amplifier anchor segments. As described herein and shown in FIG. 1, the COM provides collaboration hybridization between the SPM and NPM, which are bound to the target nucleic acid via the SP and NP, respectively. The collaboration hybridization configuration of the COM provides additional specificity and a greater signal to noise ratio since the label probe system (LPS) will not bind to the target nucleic acid unless the COM is bound to both the SPM and NPM. As discussed above, a further increase in signal is provided by increasing the number of SPCAs and NPCAs on the SPM and NPM, respectively. The collaborative hybridization of multiple COMs is enhanced further by having multiple collaborative hybridization reactions occur when the complex is specifically bound to the target nucleic acid (see FIG. 1).

The COM also comprises a third segment, which comprises a plurality of label amplifier anchor segments. The label amplifier anchor segments are complementary to segments of the label amplifiers (LMs). The binding of the COM to the label amplifiers (LMs) is generally a stable hybridization. Thus, the label amplifier anchor segments are generally of a length that provides stable hybridization between the COM and the LMs under the assay conditions used. The label amplifier anchor segments are generally about 20 to 28 nucleotides in length, but can be somewhat shorter or longer depending on the assay conditions used, such as about 15 to 30 nucleotides in length. Thus, in general, the label amplifier anchor segments can be 15, 16, 17, 18, 19, 20, 21, 22, 23, 24, 25, 26, 27, 28, 29 or 30 nucleotides in length.

The length of a COM is selected based on the desired characteristics of the assay. As described above, the COM will contain a first segment complementary to the SPCA, a second segment complementary to the NPCA, and a third segment comprising a plurality of label amplifier anchor segments. The label amplifier anchor segments provide binding sites for label amplifiers (LMs). As shown in FIG. 4, the COM can optionally contain a spacer independently between the first, second and/or third segments. The length of the spacer and orientation of the first and second segment among SPCA and NPCA can be selected to maximize the collaborative hybridization effect. The first and second segments of COM can hybridize to SPCA and NPCA in the same or different orientations as shown in FIGS. 4A, 4B and 4C, respectively. The spacer is generally and independently 1 to 10 nucleotides in length. Thus, a spacer between the first, second and/or third segments of a COM generally can be, independently, 1, 2, 3, 4, 5, 6, 7, 8, 9 or 10 nucleotides in length, depending on the configuration of the SGC.

The modified bases, such as LNA or BNA, can be used in SPCA, NPCA or their complementary sequences in COM, which increases the binding strength of the base to its complementary base, allowing an increase of the melting temperature of the hybridization between SPM and COM or between NPM and COM individually, or a reduction in the length of the anchoring segments (see, for example, Petersen and Wengel, *Trends Biotechnol.* 21:74-81 (2003); U.S. Pat. No. 7,399,845). More importantly, such an approach substantially increases the difference between the melting temperatures of individual SPM-COM or NPM-COM hybridization and the SPM-NPM-COM collaborative hybridization. Such a difference can be important to the enhancement of the signal to noise ratio in the assay of the invention because the binding of COM to an individual SPM or NPM is significantly more unstable than the binding of COM to a SPM/NPM pair. This ensures that an SGC can only be assembled when it is specifically associated in the presence of the target.

Similarly, the third segment of a COM contains a plurality of label amplifier anchor segments. The label amplifier anchor segments can also optionally and independently have a spacer between them. Thus, a spacer between the label amplifier anchor segments can be, independently, 1, 2, 3, 4, 5, 6, 7, 8, 9 or 10 nucleotides in length. Therefore, depending on the length of the first, second and third segments, a COM will generally be about 60 to 900 nucleotides in length.

In an embodiment of a method of the invention, the sample is contacted with a label probe system (LPS). The LPS comprises a plurality of label amplifiers (LMs). Each LM comprises a segment that can bind to a label amplifier anchor segment of the COM. The LM also comprises a plurality of label probe anchor segments. The binding of the LMs to the label probes (LPs) is generally a stable hybridization. Thus, the label probe anchor segments are generally of a length that provides stable hybridization between the LM and the LPs under the assay conditions used. The label probe anchor segments are generally about 15 to 28 nucleotides in length, but can be somewhat shorter or longer depending on the assay conditions used, such as about 12 to 30 nucleotides in length. Thus, in general, the label probe anchor segments can be 12, 13, 14, 15, 16, 17, 18, 19, 20, 21, 22, 23, 24, 25, 26, 27, 28, 29 or 30 nucleotides in length.

As described herein, to further increase the signal associated with an SGC, the number of LMs bound to a COM can be increased (see FIG. 1). The number of LMs can be selected to give a desired signal strength or increased signal to noise ratio. As shown in FIG. 1, a plurality of LMs can bind to a COM via the label amplifier anchor segments. Increasing the number of label amplifier anchor segments on the COM will increase the number of LMs bound to the COM. This in turn will result in a corresponding increase in the number of label probes bound to the target nucleic acid. The number of LMs bound to the COM will generally be 2 to 20, although it is understood that a higher number can be used, if desired. Thus, a COM will generally have 2, 3, 4, 5, 6, 7, 8, 9, 10, 11, 12, 13, 14, 15, 16, 17, 18, 19 or 20 label amplifier anchor segments, providing binding for 2, 3, 4, 5, 6, 7, 8, 9, 10, 11, 12, 13, 14, 15, 16, 17, 18, 19 or 20 LMs per COM.

The LPS also comprises a plurality of label probes (LPs). Each LP comprises one or more detectable labels and a segment that hybridizes to the label probe anchor segment of LM. As used herein, a "label" is a moiety that facilitates detection of a molecule. Common labels in the context of the present invention include fluorescent, luminescent, light-scattering, and/or colorimetric labels. Suitable labels include enzymes, and fluorescent and chromogenic moieties, as well as radionuclides, substrates, cofactors, inhibitors, chemiluminescent moieties, magnetic particles, rare earth metals, and the like. In a particular embodiment of the invention, the label is an enzyme. Exemplary enzyme labels include, but are not limited to Horse Radish Peroxidase (HRP), Alkaline Phosphatase (AP), β-galactosidase, glucose oxidase, and the like, as well as various proteases. Other labels include, but are not limited to, fluorophores, Dinitrophenyl (DNP), and the like. Labels are well known to those skilled in the art, as described, for example, in Hermanson, *Bioconjugate Techniques*, Academic Press, San Diego (1996), and U.S. Pat. Nos. 3,817,837; 3,850,752; 3,939,350; 3,996,345; 4,277,437; 4,275,149; and 4,366,241. Many labels are commercially available and can be used in methods and assays of the invention, including detectable enzyme/substrate combinations (Pierce, Rockford Ill.; Santa Cruz Biotechnology, Dallas Tex.; Invitrogen, Carlsbad Calif.). In a particular embodiment of the invention, the enzyme can utilize a chromogenic or fluorogenic substrate to produce a detectable signal, as described herein. Exemplary labels are described herein.

Any of a number of enzymes or non-enzyme labels can be utilized so long as the enzymatic activity or non-enzyme label, respectively, can be detected. The enzyme thereby produces a detectable signal, which can be utilized to detect a target nucleic acid. Particularly useful detectable signals are chromogenic or fluorogenic signals. Accordingly, particularly useful enzymes for use as a label include those for which a chromogenic or fluorogenic substrate is available. Such chromogenic or fluorogenic substrates can be converted by enzymatic reaction to a readily detectable chromogenic or fluorescent product, which can be readily detected and/or quantified using microscopy or spectroscopy. Such enzymes are well known to those skilled in the art, including but not limited to, horseradish peroxidase, alkaline phosphatase, β-galactosidase, glucose oxidase, and the like (see Hermanson, *Bioconjugate Techniques*, Academic Press, San Diego (1996)). Other enzymes that have well known chromogenic or fluorogenic substrates include various peptidases, where chromogenic or fluorogenic peptide substrates can be utilized to detect proteolytic cleavage reactions. The use of chromogenic and fluorogenic substrates is also well known in bacterial diagnostics, including but not limited to the use of α- and β-galactosidase, β-glucuronidase, 6-phospho-β-D-galatoside 6-phosphogalactohydrolase, β-gluosidase, α-glucosidase, amylase, neuraminidase, esterases, lipases, and the like (Manafi et al., *Microbiol. Rev.* 55:335-348 (1991)), and such enzymes with known chromogenic or fluorogenic substrates can readily be adapted for use in methods of the present invention.

Various chromogenic or fluorogenic substrates to produce detectable signals are well known to those skilled in the art and are commercially available. Exemplary substrates that can be utilized to produce a detectable signal include, but are not limited to, 3,3'-diaminobenzidine (DAB), 3,3',5,5'-tetramethylbenzidine (TMB), Chloronaphthol (4-CN)(4-chloro-1-naphthol), 2,2'-azino-bis(3-ethylbenzothiazoline-6-sulphonic acid) (ABTS), o-phenylenediamine dihydrochloride (OPD), and 3-amino-9-ethylcarbazole (AEC) for horseradish peroxidase; 5-bromo-4-chloro-3-indolyl-1-phosphate (BCIP), nitroblue tetrazolium (NBT), Fast Red (Fast Red TR/AS-MX), and p-Nitrophenyl Phosphate (PNPP) for alkaline phosphatase; 1-Methyl-3-indolyl-O-D-galactopyranoside and 2-Methoxy-4-(2-nitrovinyl)phenyl β-D-galactopyranoside for β-galactosidase; 2-Methoxy-4-(2-nitrovinyl)phenyl β-D-glucopyranoside for β-glucosidase; and the like. Exemplary fluorogenic substrates include, but are not limited to, 4-(Trifluoromethyl)umbelliferyl phosphate for alkaline phosphatase; 4-Methylumbelliferyl phosphate bis (2-amino-2-methyl-1,3-propanediol), 4-Methylumbelliferyl phosphate bis (cyclohexylammonium) and 4-Methylumbelliferyl phosphate for phosphatases; QuantaBlu™ and QuantaRed™ for horseradish peroxidase; 4-Methylumbelliferyl β-D-galactopyranoside, Fluorescein di(β-D-galactopyranoside) and Naphthofluorescein di-(β-D-galactopyranoside) for β-galactosidase; 3-Acetylumbelliferyl β-D-glucopyranoside and 4-Methylumbelliferyl-β-D-glucopyranoside for β-glucosidase; and 4-Methylumbelliferyl-α-D-galactopyranoside for α-galactosidase. Exemplary enzymes and substrates for producing a detectable signal are also described, for example, in US publication 2012/0100540. Various detectable enzyme substrates, including chromogenic or fluorogenic substrates, are well known and commercially available (Pierce, Rockford Ill.; Santa Cruz Biotechnology, Dallas Tex.; Invitrogen, Carlsbad Calif.; 42 Life Science; Biocare). Generally, the substrates are converted to products that form precipitates that are deposited at the site of the target nucleic acid. Other exemplary substrates include, but are not limited to, HRP-Green (42 Life Science), Betazoid DAB, Cardassian DAB, Romulin AEC, Bajoran Purple, Vina Green, Deep Space Black™, Warp Red™, Vulcan Fast Red and Ferangi Blue from Biocare (Concord Calif.; biocare.net/products/detection/chromogens).

Biotin-avidin (or biotin-streptavidin) is a well known signal amplification system based on the fact that the two molecules have extraordinarily high affinity to each other and that one avidin/streptavidin molecule can bind four biotin molecules. Antibodies are widely used for signal amplification in immunohistochemistry and ISH. Tyramide signal amplification (TSA) is based on the deposition of a large number of haptenized tyramide molecules by peroxidase activity. Tyramine is a phenolic compound. In the presence of small amounts of hydrogen peroxide, immobilized Horse Radish Peroxidase (HRP) converts the labeled substrate into a short-lived, extremely reactive intermediate. The activated substrate molecules then very rapidly react with and covalently bind to electron-rich moieties of proteins, such as tyrosine, at or near the site of the peroxidase binding site. In this way, a lot of extra hapten molecules conjugated to tyramide can be introduced at the hybridization site in situ. Subsequently, the deposited tyramide-hapten molecules can be visualized directly or indirectly. Such a detection system is described in more detail, for example, in U.S. publication 2012/0100540.

Embodiments described herein can utilize enzymes to generate a detectable signal using appropriate chromogenic or fluorogenic substrates. It is understood that, alternatively, a label probe can have a detectable label directly coupled to the nucleic acid portion of the label probe. Exemplary detectable labels are well known to those skilled in the art, including but not limited to chromogenic or fluorescent labels (see Hermanson, *Bioconjugate Techniques*, Academic Press, San Diego (1996)). Exemplary fluorophores useful as labels include, but are not limited to, rhodamine derivatives, for example, tetramethylrhodamine, rhodamine B, rhodamine 6G, sulforhodamine B, Texas Red (sulforhodamine 101), rhodamine 110, and derivatives thereof such as tetramethylrhodamine-5-(or 6), lissamine rhodamine B, and the like; 7-nitrobenz-2-oxa-1,3-diazole (NBD); fluorescein and derivatives thereof; napthalenes such as dansyl (5-dimethylaminonapthalene-1-sulfonyl); coumarin derivatives such as 7-amino-4-methylcoumarin-3-acetic acid (AMCA), 7-diethylamino-3-[(4'-(iodoacetyl)amino)phenyl]-4-methylcoumarin (DCIA), Alexa fluor dyes (Molecular Probes), and the like; 4,4-difluoro-4-bora-3a,4a-diaza-s-indacene (BODIPY™) and derivatives thereof (Molecular Probes; Eugene Oreg.); pyrenes and sulfonated pyrenes such as Cascade Blue™ and derivatives thereof, including 8-methoxypyrene-1,3,6-trisulfonic acid, and the like; pyridyloxazole derivatives and dapoxyl derivatives (Molecular Probes); Lucifer Yellow (3,6-disulfonate-4-aminonaphthalimide) and derivatives thereof; CyDye™ fluorescent dyes (Amersham/GE Healthcare Life Sciences; Piscataway N.J.), and the like. Exemplary chromophores include, but are not limited to, phenolphthalein, malachite green, nitroaromatics such as nitrophenyl, diazo dyes, dabsyl (4-dimethylaminoazobenzene-4'-sulfonyl), and the like.

Well known methods such as microscopy, cytometry (mass cytometry, CyTOF), or spectroscopy can be utilized to visualize chromogenic or fluorescent detectable signals associated with the respective target nucleic acids. In general, either chromogenic substrates or fluorogenic substrates, or chromogenic or fluorescent labels, will be utilized for a particular assay, if different labels are used in the same assay, so that a single type of instrument can be used for detection of nucleic acid targets in the same sample.

As described herein, to further increase the signal associated with an SGC, the number of LPs bound to an LM can be increased (see FIG. 1). The number of LPs can be selected to give a desired signal strength or increased signal to noise ratio. As shown in FIG. 1, a plurality of LPs can bind to an LM via the label probe anchor segments. Increasing the number of label probe anchor segments on the LM will increase the number of LPs bound to the LM. This results in an increase in the number of label probes bound to the target nucleic acid. The number of LPs bound to the LM will generally be 2 to 20, although it is understood that a higher number can be used, if desired. Thus, an LM will generally have 2, 3, 4, 5, 6, 7, 8, 9, 10, 11, 12, 13, 14, 15, 16, 17, 18, 19 or 20 label probe anchor segments, providing binding for 2, 3, 4, 5, 6, 7, 8, 9, 10, 11, 12, 13, 14, 15, 16, 17, 18, 19 or 20 LPs per LM.

When the components described above hybridize, a signal generating complex (SGC) is formed. The SGC comprises a target nucleic acid with the nucleotide variation, for example, single nucleotide variation, multi-nucleotide variation, splice site, insertion/deletion, rearrangement, and the like, an SP, an NP, an SPM, an NPM, a plurality of COMs, a plurality of LMs, and a plurality of LPs. Once the SGC is formed, the in situ signal can be detected from the SGC on the sample. After assembling each component, the sample can be optionally washed to remove unbound component prior to adding the next layer of component to the sample.

The modified bases, such as LNA or BNA, can be used in the anchoring segments of selected components of SGC, which increases the binding strength of the base to its complementary base, allowing a reduction in the length of the anchoring segments (see, for example, Petersen and Wengel, *Trends Biotechnol.* 21:74-81 (2003); U.S. Pat. No. 7,399,845). Artificial bases that expand the natural 4-letter alphabet such as the Artificially Expanded Genetic Information System (AEGIS; Yang et al., *Nucl. Acids Res.* 34 (21): 6095-6101 (2006)) can be incorporated into the binding sites among the interacting components of the SGC (for example, SPAP~SPM, NPAP~NPM, SPCA~COM, NPCA~COM, and LP~LM hybridization sites). These artificial bases can increase the specificity of the interacting components, which in turn can allow lower stringency hybridization reactions to yield a higher signal.

Figure 5B:
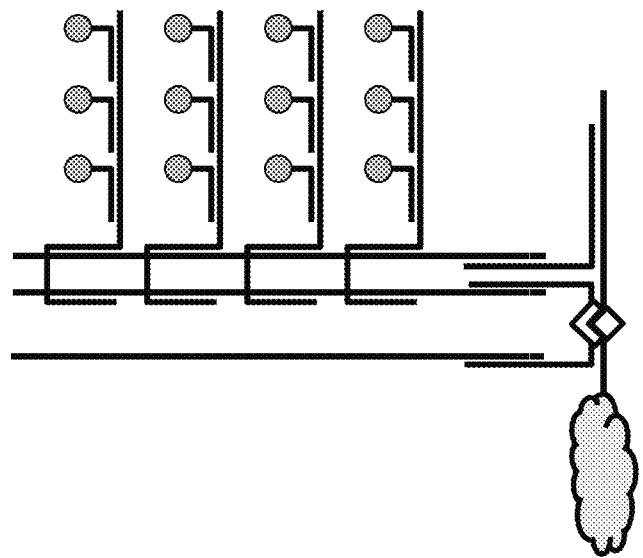
FIGS. 5A and 5B show an exemplary configuration where two signal-generating complexes(SGCs) are captured to a single nucleotide variation (SNV).
Figure 5A:
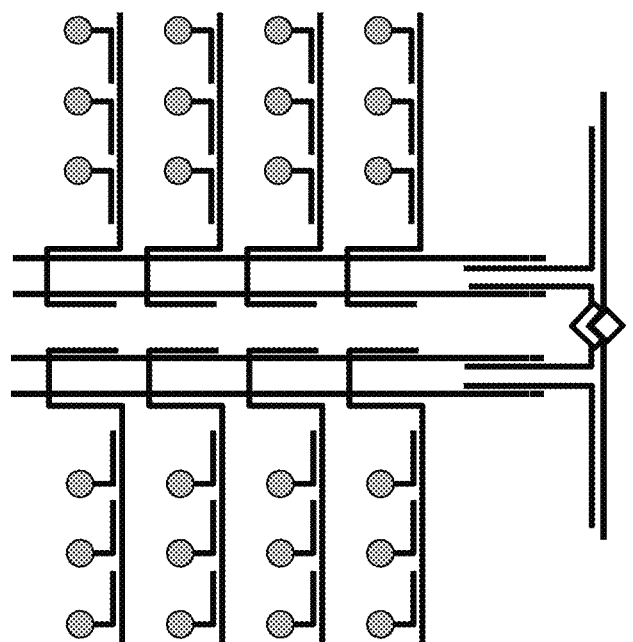

It can be useful to use a configuration with an NP on each side of the SP, as shown in FIG. 5. Such a configuration provides for capture of two SGCs to a target nucleic acid containing a nucleotide variant such as an SNV, a multi-nucleotide variant, splice site, insertion/deletion, rearrangement, and the like. Such a configuration can additionally be used to double the signal. Alternatively, it can also be used to enhance the robustness of the assay. For example, as shown in FIG. 5B, if the access of one NP is blocked due to insufficient permeablization, or if the binding site to the target nucleic acid is lost due to RNA degradation, a detectable signal can still be generated by the SGC bound to the other NP.

In an embodiment of the invention, the nucleic acid detected by the methods of the invention can be any nucleic acid present in the cell sample, including but not limited to, RNA, including messenger RNA (mRNA), micro RNA (miRNA), ribosomal RNA (rRNA), mitochondrial RNA, and the like, or DNA, and the like. In a particular embodiment, the nucleic acid is RNA.

In a further embodiment of the invention, the fixed and permeabilized cells are immobilized on a tissue slide. Methods for fixing and permeabilizing cells for immobilizing on a tissue slide are well known in the art, as disclosed herein.

As disclosed herein, the invention is based on building a signal-generating complex (SGC) bound to a target nucleic acid in order to detect the presence of the target nucleic acid in the cell. The components for building an SGC generally comprise nucleic acids such that nucleic acid hybridization reactions are used to bind the components of the SGC to the target nucleic acid. Methods of selecting appropriate regions and designing specific and selective reagents that bind to the target nucleic acids, in particular oligonucleotides or probes that specifically and selectively bind to a target nucleic acid, or other components of the SGC, are well known to those skilled in the art (see Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999)). A desired specificity can be achieved using appropriate selection of regions of a target nucleic acid as well as appropriate lengths of a binding agent such as an oligonucleotide or probe, and such selection methods are well known to those skilled in the art. Thus, one skilled in the art will readily understand and can readily determine appropriate reagents, such as oligonucleotides or probes, that can be used to target one particular target nucleic acid over another target nucleic acid, or to provide binding to the components of the SGC such as SP, NP, SPM, NPM, COM, LM and LP.

As disclosed herein, the steps of the methods of the invention, whereby components are assembled into an SGC bound to a target nucleic acid, can be performed concurrently or sequentially, in any order, so long as the target nucleic acid can be detected. In some cases, it can be desirable to reduce the number of assay steps, for example, reduce the number of hybridization and wash steps. One way of reducing the number of assay steps is to pre-assemble some or all components of the SGC prior to contacting with a cell. Such a pre-assembly can be performed by hybridizing some or all of the components of the SGC together prior to contacting the target nucleic acid. It is also possible to reduce the assay steps by pre-making some part of the SGC to integrate multiple components of the SGC through chemical synthesis. One exemplary embodiment is depicted in FIG. 6A. FIG. 6A shows the integration of SPM with COM and NPM with COM using a pre-fabricated amplification molecule with a "branched" structure. In this depicted embodiment, the SPM and NPM use a nucleic acid "branch" to connect to the COM, rather than an SPCA or NPCA as depicted in FIG. 6A. In this case, collaborative or collaboration hybridization occurs at the binding of LM to the COM of the SPM-COM branched molecule.

Figure 6B:
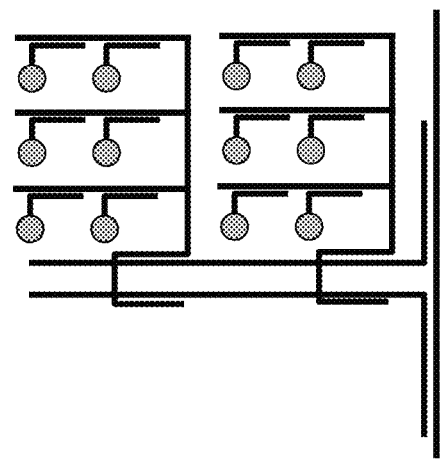
FIGS. 6A and 6B show exemplary embodiments where the number of assay steps are reduced. The assay steps can be reduced by pre-assembling components of the SGC.
Figure 6A:
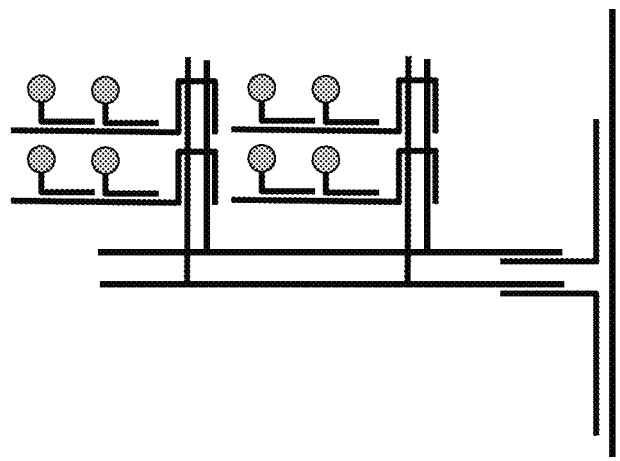

Another embodiment is depicted in FIG. 6B. FIG. 6B shows integration of SP and NP with the SMP and NPM, respectively, by extending the SP and NP to a longer sequence that includes SPCAs and NPCAs. The SGC can then be assembled with COMs, LMs and LPs, as depicted in FIG. 1, with the COMs bound to the SPCAs and NPCAs of the extended SP and NP, as depicted in FIG. 6B. Alternatively, the SGC can be assembled with the configuration depicted in FIG. 6B, in which the COM and LM are integrated by using a "branched" configuration, as described above. The LM is connected to the COM as a branched nucleic acid, rather than being bound by way of the label amplifier anchor segments, as depicted in FIG. 1. In this depicted embodiment, the collaborative hybridization occurs between the COM portion of the COM-LM branched molecule and the extended SP and NP, which contain SPCAs and NPCAs, respectively.

Large molecules are more prone to bind non-specifically or get stuck in the cellular matrix during in situ assays. This is a potential disadvantage of using a "branched" molecule that provide large molecules for in situ detection assays. However, methods of the invention, as disclosed herein, overcome this problem because a single large amplification molecule cannot form the SGC alone. For example, in the embodiment shown in FIG. 6A, the SGC cannot form without the presence of its pair (SP and NP bound to the target nucleic acid), so it will not generate noise or a false positive signal. In FIG. 6B, although a single "branched" large molecule can generate background noise if non-specifically bound, the intensity level of a true signal can be adjusted so that the number of labels bound to a target nucleic acid are greater than than that of a COM-LM branched molecule with bound label probes, as described herein (for example, increasing the number of SPCAs and NPCAs on the extended SP and TP).

Thus, it is understood that, if desired, an intermediary component can be included such that the binding of one component to another is pre-assembled by chemical link. For example, in another embodiment, the LM can be a large pre-made molecule comprising many labels. In still another embodiment, the COM+LPS (COM/LM/LP) can be a chemically synthesized as a single large molecule. The use of such pre-made large molecules can effectively reduce the number of assay steps. Methods of making such nucleic acid configurations, including branched nucleic acid configurations as discussed above and shown in FIGS. 6A and 6B, are well known in the art (see, for example, U.S. Pat. Nos. 5,635,352 and 5,681,697, which are incorporated herein by reference).

As disclosed herein, the components are generally bound directly to each other. In the case of nucleic acid containing components, the binding reaction is generally by hybridization. In the case of a hybridization reaction, the binding between the components is direct. If desired, an intermediary component can be included such that the binding of one component to another is indirect, for example, the intermediary component contains complementary binding sites to bridge two other components.

It is understood that the invention can be carried out in any desired order, so long as the variant target nucleic acid is detected. Thus, in a method of the invention, the steps of contacting a cell with an SP, NP, SPM, NPM, COM and/or LPS can be performed in any desired order, can be carried out sequentially, or can be carried out simultaneously, or some steps can be performed sequentially while others are performed simultaneously, as desired, so long as the target nucleic acid is detected. It is further understood that embodiments disclosed herein can be independently combined with other embodiments disclosed herein, as desired, in order to utilize various configurations, component sizes, assay conditions, assay sensitivity, and the like.

The methods of the invention, and related compositions, utilize collaboration hybridization to increase specificity and to reduce background in in situ detection of nucleic acid targets, where a complex physiochemical environment and the presence of an overwhelming number of non-target molecules generates high noise. FIG. 1 illustrates an exemplary embodiment, where the collaboration hybridization is provided by the binding of a COM to an SPM and NPM. Using such a collaboration hybridization method, the binding of two or more COMs only occurs when the complex is bound to the target nucleic acid. As illustrated in FIG. 1, this allows the method to be readily modified to provide a desired signal to noise ratio by increasing the number of COMs that can bind to the target nucleic acid (that is, by increasing the number of SPCAs and NPCAs on the SPM and NPM, respectively).

In another embodiment, the collaboration hybridization can be applied to other components of the SGC as well. For example, the binding of LMs to the COMs can be a stable reaction, as described herein, or the binding can be configured to require a collaboration hybridization. In such a case, the LM is designed such that the LM contains two segments that bind to separate COMs. This configuration would be similar to the relationship of a COM to the SPM and NPM, but instead the LM would bind to a COM-1 and a COM-2. The LM and COMs are designed to have appropriate complementary segments, as with the COM, SPM and NPM depicted in FIG. 7A, to provide collaboration hybridization.

Similarly, a further layer of collaboration hybridization can be utilized for binding of the LPs to the LM. In such a case, the LP is designed such that the LP contains two segments that bind to separate LMs. This configuration would be similar to the relationship of a COM to the SPM and NPM, but instead the LP would bind to an LM-1 and an LM-2. The LP and LMs are designed to have appropriate complementary segments, as with the COM, SPM and NPM depicted in FIG. 7B, to provide collaboration hybridization.

Thus, the methods for detecting a target nucleic acid variation can utilize collaboration hybridization for the binding reactions between any one or all of the components in the detection system that provides an SGC specifically bound to a target nucleic acid. The number of components, and which components, to apply collaboration hybridization can be selected based on the desired assay conditions, the type of sample being assayed, a desired assay sensitivity, and so forth. Any one or combination of collaboration hybridization binding reactions can be used to increase the sensitivity and specificity of the assay.

Figure 8A:
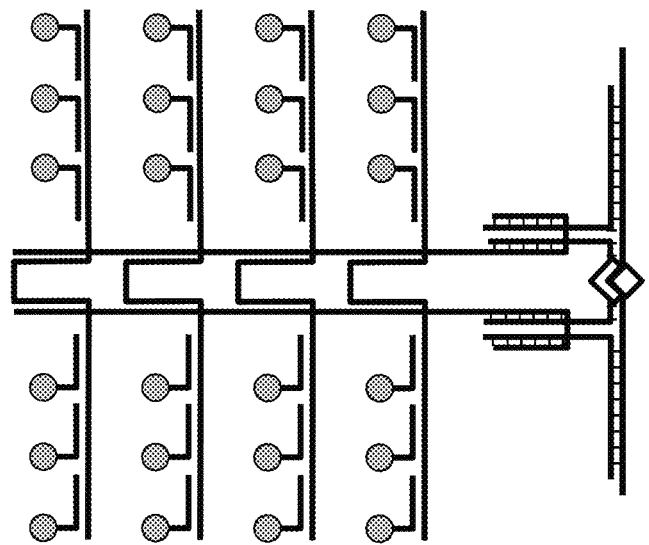

FIG. 8 depicts two examples of SGC configurations that use collaborative hybridization between more than two components in the complex. In the configuration depicted in FIG. 8A, two collaborative hybridization steps have to occur in order to build a stable SGC scaffold. In the depicted configuration, the SP is flanked by two NPs. A first collaborative hybridization occurs between the SPM/NPM and the SP and two NPs bound to the target nucleic acid. A second collaborative hybridization occurs between the COMs and SPM/NPM. Since collaborative hybridization enhances specificity and signal to noise ratio, as described herein, two collaborative hybridization steps can further increase the assay robustness in a high noise environment. FIG. 8B shows a different approach of utilizing two collaborative hybridization steps to improve specificity. In this embodiment, the first collaborative hybridization occurs between the SP and NP, where the SP and NP are designed to have complementary sections. In this configuration, the SP and NP have three segments, a first segment containing an SPAT or NPAT, which binds to the target nucleic acid (labeled "T" in FIG. 8B), a second segment that contains a complementary sequence to the respective NP or SP (labeled "P" in FIG. 8B), and a third segment containing an SPAP or NPAP, which can bind to the COM (labeled "L" in FIG. 8B). The SP and NP hybridize to the target nucleic acid and to each other collaboratively in order for the target probe set (SP and NP) and the target nucleic acid to form a stable scaffold. Then SMP and NMP hybridize individually onto SP and NP, respectively, and the COMs hybridize collaboratively to the SP and NP.

As described herein, the configuration of various components can be selected to provide a desired stable or collaboration hybridization binding reaction. It is understood that, even if a binding reaction is exemplified herein as a stable or unstable reaction, any of the binding reactions can be modified, as desired, so long as the target nucleic acid is detected. It is further understood that the configuration can be varied and selected depending on the assay and hybridization conditions to be used. In general, if a binding reaction is desired to be stable, the segments of complementary nucleic acid sequence between the components is generally in the range of 16 to 30 nucleotides, or greater. If a binding reaction is desired to be relatively unstable, such as when a collaboration hybridization binding reaction is employed, the segments of complementary nucleic acid sequence between the components is generally in the range of 10 to 18 nucleotides. It is understood that the nucleotide lengths can be somewhat shorter or longer for a stable or unstable hybridization, depending on the conditions employed in the assay. It is further understood, as disclosed herein, that modified nucleotides such as LNA or BNA can be used to increase the binding strength at the modified base, thereby allowing length of the binding segment to be reduced. Thus, it is understood that, with respect to the length of nucleic acid segments that are complementary to other nucleic acid segments, the lengths described herein can be reduced further, if desired. For example, microRNA is known to have short sequence of about 22nt. In order to use a SP-NP pair, a certain number of modified nucleotides such as LNA or BNA can be incorporated in the SPAT and/or NPAT to reduce their length so that one or more SGCs can be assembled on a target microRNA.

The assay sensitivity can be further enhanced by selecting the number of components and binding reactions employed in the assay. As described herein, in addition to providing one or more collaboration hybridization binding reactions, the signal can be increased by increasing the number of SPCAs and NPCAs on the SPM and NPM, respectively. An increased number of SPCAs and NPCAs provides for an increased number of COMs bound to the target nucleic acid. Similarly, the signal can also be increased by increasing the number of label amplifier anchor segments on the COM. An increased number of label amplifier anchor segments provides for an increased number of LMs bound to a COM. Further, the signal can be increased by increasing the number of label probe anchor segments on the LM. An increased number of label probe anchor segments provide for an increased number of LPs bound to an LM. It is understood that any of these options for increasing signal can be applied, as desired. Similarly and depending on application, the signal can be reduced by appropriately reducing the number of anchor segments mentioned above. Thus, the invention provides great flexibility for modifying the configuration of components of the assay to provide very sensitive detection of a target nucleic acid. Alternatively, the signal level can also be reduced by eliminating a layer of such intermediary amplification molecules. For example, a plurality of LP can bind directly to COM, eliminating LM. On the other hand, the signal level can also be increased by adding one or more layers of such intermediary amplification molecules.

Figure 7A:
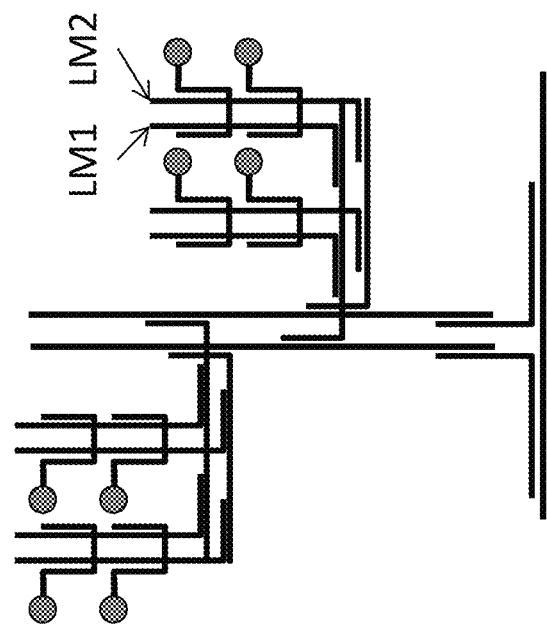
FIGS. 7A and 7B show exemplary embodiments where collaborative hybridization is moved to different layers within SGC.
Figure 7B:
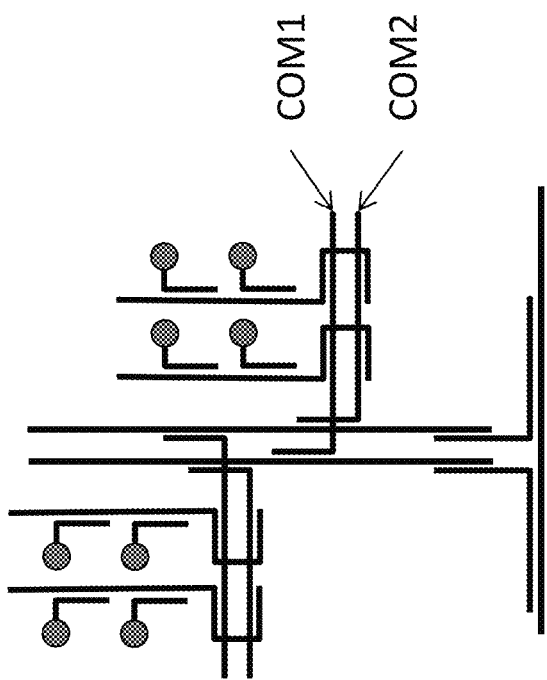

As described herein, the present invention involves building a SGC around a target nucleic acid containing a nucleotide variant such as an SNV, multi-nucleotide variant, splice site, or other nucleic acid variation. The SGC comprises at least an SP that can specifically and sensitively bind to the nucleotide variant such as an SNV, multi-nucleotide variant, splice site, or other nucleic acid variation, of the target nucleic acid and that has sufficient discrimination such that the SP does not bind to non-target nucleic acids such as non-SNV sequences, non-multi-nucleotide variant sequences, non-spliced sequences, and the like. Once the SP binds to the SNV of the target nucleic acid along with an NP, a large SGC is assembled with multiple layers of amplification components, such as SPM/NPM, COM and LM on top of them, providing a large number of LPs to build up in the SGC to generate sufficient signal to be detected. Such signal can present as a distinct "dot" in an imaging system. For example, if each SPM/NPM pair can carry A1 number of COM molecules, each COM can bind A2 number of LM molecules, and each LM can bind A3 number of LP molecules, the total number of LPs in an SGC is A1×A2×A3. Considering A1, A2 and A3 can each be as large as 20 or above, the total number of LPs in a SGC can be up to 8,000 and above. For the present invention, a "dot" in the staining image distinctively represents a target nucleic acid containing a nucleotide variant such as an SNV, multi-nucleotide variant, splice site, or other nucleotide variant, in the cell. The minimum number of LPs needed in an SGC is determined by the sensitivity of the detection instrument as well as the amount of signal that can be generated by each LP. In one embodiment where LP comprises fluorescent dyes, the minimum number of LPs in an SGC is at least 800, at least 1200, at least 1500, at least 2000, at least 2500 or at least 3000 to produce sufficient signal to be detected by an instrument. In another embodiment, LP comprises additional signal amplification, as described herein. The minimum number of LPs needed in an SGC can be reduced to at least 300, at least 600, at least 1000 or at least 1500. Some components of the SGC scaffold may bind non-specifically or get stuck in a cell which may "collect" a certain number of LPs and generate a false positive signal. An important aspect of the invention is the collaborative hybridization mechanisms built into the SGC structure so that any one component within the SGC scaffold that is non-specifically bound or stuck in a cell cannot generate detectable signal or at least only weak signal that can be distinguished by the system as background noise. For example, if the collaborative hybridization is built between COM and SPM+NPM, the maximum level of noise is generated when a COM molecule is non-specifically bound or stuck with a false signal level at A2×A3 LPs. The theoretical signal to noise ratio of the assay is A1 (=A1×A2×A3/A2×A3). If the collaborative hybridization is built between LM and COM, as shown in FIGS. 6A and 7A, the maximum false signal level is generated when an LM is stuck with A3 number of LPs. The theoretical signal to noise ratio of the assay becomes A1×A2. Similarly, the assay signal to noise ratio is A1×A2×A3 with the configuration shown in FIG. 7B. In specific embodiments, this theoretical signal to noise ratio is at least 2, 4, 7, 10, 20, 30, 40, 50, 60, 70, 80, 90, 100 or 200.

As described previously, longer molecules with more repeats are needed to increase the signal generated by the SGC. However, larger molecules may have more difficulty penetrating into the cellular matrix to reach its hybridization sites and are harder to be washed out when they are stuck non-specifically in cell structures, thereby generating background noise. In addition, larger molecules are also more expensive to produce. It is therefore important to find optimized sizes for each layer of amplification within. In one embodiment, A1 is relatively large because, as discussed previously, non-specific binding of SPM or NPM alone will not produce false signal and larger A1 leads to a higher signal-to-noise ratio. In one embodiment of this invention, A1 is in the range of 4 to 20. In another embodiment, A1 is preferably in the range of 6 to 16. Optionally, A2 is relatively smaller because non-specific binding or trapping of a single COM can result in an assembly of A2×A3 LPs generating an equivalent level of background noise. In one embodiment, A2 is in the range of 3 to 15. In another embodiment, A2 is preferably in the range of 5 to 12. Optionally, A3 can be relatively large compared to A2, because non-specific binding or trapping of an LM molecule would produce a relatively low level of noise proportional to A3. Another method is to add one or more additional amplification layer in SGC in order to reduce the length of molecule in individual layers.

In another embodiment, the invention provides a sample of fixed and permeabilized cells, comprising (A) at least one fixed and permeabilized cell containing a target nucleic acid with a single nucleotide variation; (B) a single nucleotide variation probe (SP) comprising a target anchor segment (SPAT) hybridized to a region of the target nucleic acid comprising the single nucleotide variation, and, a neighbor probe (NP) comprising a target anchor segment (NPAT) hybridized to a region of the target nucleic acid adjacent to the binding site of the SP; (C) an SP pre-amplifier (SPM) hybridized to the SP, wherein the SPM comprises a plurality of SP collaboration anchors (SPCAs), and, an NP pre-amplifier (NPM) hybridized to the NP, wherein the NPM comprises a plurality of NP collaboration anchors (NPCAs); (D) a plurality of collaboration amplifiers (COMs) each hybridized to the SPM and the NPM, wherein each COM comprises a first segment complementary to the SPCA, a second segment complementary to the NPCA, and third segment comprising a plurality of label amplifier anchor segments; (E) a plurality of label amplifiers (LMs) each hybridized to a label amplifier anchor segment of the COM, wherein the LM comprises a plurality of label probe anchor segments; and (F) a plurality of label probes (LPs) each hybridized to a label probe anchor segment of the LM, wherein the LP comprises a detectable label; wherein the aforesaid hybridizations form a signal generating complex (SGC) comprising the target nucleic acid with the single nucleotide variation, an SP, an NP, an SPM, an NPM, a plurality of COMs, a plurality of LMs, and a plurality of LPs, and wherein the SGC provides a signal that is detectable and distinguishable from the background noise.

In an additional embodiment, the invention provides a tissue slide, comprising (A) a slide having immobilized thereon a plurality of fixed and permeabilized cells comprising at least one fixed and permeabilized cell containing a target nucleic acid with a single nucleotide variation; (B) a single nucleotide variation probe (SP) comprising a target anchor segment (SPAT) hybridized to a region of the target nucleic acid comprising the single nucleotide variation, and, a neighbor probe (NP) comprising a target anchor segment (NPAT) hybridized to a region of the target nucleic acid adjacent to the binding site of the SP; (C) an SP pre-amplifier (SPM) hybridized to the SP, wherein the SPM comprises a plurality of SP collaboration anchors (SPCAs), and, an NP pre-amplifier (NPM) hybridized to the NP, wherein the NPM comprises a plurality of NP collaboration anchors (NPCAs); (D) a plurality of collaboration amplifiers (COMs) each hybridized to the SPM and the NPM, wherein each COM comprises a first segment complementary to the SPCA, a second segment complementary to the NPCA, and a third segment comprising a plurality of label amplifier anchor segments; (E) a plurality of label amplifiers (LMs) each hybridized to a label amplifier anchor segment of the COM, wherein the LM comprises a plurality of label probe anchor segments; and (F) a plurality of label probes (LPs) each hybridized to a label probe anchor segment of the LM, wherein the LP comprises a detectable label; wherein the aforesaid hybridizations form a signal generating complex (SGC) comprising the target nucleic acid with the single nucleotide variation, an SP, an NP, an SPM, an NPM, a plurality of COMs, a plurality of LMs, and a plurality of LPs, and wherein the SGC provides a signal that is detectable and distinguishable from the background noise.

In still another embodiment, the invention provides a kit for in situ detection of a single nucleotide variation of a target nucleic acid in a sample of fixed and permeabilized cells, comprising (A) at least one reagent for permeabilizing cells; (B) a set of target hybridizing probes comprising a single nucleotide variation probe (SP) comprising a target anchor segment (SPAT) capable of hybridizing to a region of the target nucleic acid comprising the single nucleotide variation, and, a neighbor probe (NP) comprising a target anchor segment (NPAT) capable of hybridizing to a region of the target nucleic acid adjacent to the binding site of the SP; (C) a set of pre-amplifiers comprising an SP pre-amplifier (SPM) comprising a segment capable of hybridizing to the SP, wherein the SPM comprises a plurality of SP collaboration anchors (SPCAs), and, an NP pre-amplifier (NPM) comprising a segment capable of hybridizing to the NP, wherein the NPM comprises a plurality of NP collaboration anchors (NPCAs); (D) a collaboration amplifier (COM) capable of hybridizing to the SPM and the NPM, wherein the COM comprises a first segment complementary to the SPCA, a second segment complementary to the NPCA, and a third segment comprising a plurality of label amplifier anchor segments; (E) a label amplifier (LM) capable of hybridizing to the label amplifier anchor segment of the COM, wherein the LM comprises a plurality of label probe anchor segments; and (F) a label probe (LP) capable of hybridizing to the label probe anchor segment of the LM, wherein the LP comprises a detectable label; wherein, upon contacting a sample of fixed and permeabilized cells comprising a cell containing a target nucleic acid with the single nucleotide variation, the components in aforesaid (B)-(F) form a signal generating complex (SGC) comprising the target nucleic acid with the single nucleotide variation, an SP, an NP, an SPM, an NPM, a plurality of COMs, a plurality of LMs, and a plurality of LPs, and wherein the SGC provides a signal that is detectable and distinguishable from the background noise. The components of the kit can optionally be in a container, and optionally instructions for using the kit can be provided.

As disclosed herein, the invention provides methods for detecting nucleic acid variations, such as single nucleotide variations (SNVs). Since the SP has the sensitivity and specificity to detect a single nucleotide variation in a target sequence, it is understood that a similar principle can be applied to detect other variations in target nucleic acid or short sequences that involves more than one nucleotide such as RNA splicing variants, insertions, deletions, gene rearrangements and micro RNAs. Therefore, although exemplified as detecting an SNV as a single nucleotide variation, it is understood that the methods can be applied to other types of nucleic acid variations. For example, the invention can be adopted to detect a unique junction, J, formed by two segments of nucleic acid sequences spliced together. As depicted in FIG. 9, a SP-NP probe set can be designed with SPAT spanning over the junction (FIG. 9A) or positioning the junction between NPAT and SPAT (FIG. 9B). FIG. 9C depicts another design similar to that in FIG. 8B, in which SPAT is shortened and both NP and SP have a segment that are complementary to each other. In this way, SP can only stably hybridize to target when NP is present at the adjacent position. Alternatively, NPAT or both NPAT and SPAT can be shortened in this design to achieve the same effect. In all three designs depicted in FIG. 9, SP can only stably hybridize right next to NP to form SGC and generate detectable signal when and only when the two segments in the target splices together at the junction.

The capacity to detect the splicing of two nucleic acid segments has many applications. In the case of transcript or RNA splicing, a gene is transcribed into RNA, which is processed by RNA splicing to remove introns and produce mRNA with contiguous exons providing a coding sequence. Some genes undergo alternative splicing, which can occur naturally or in a disease state. In the case of an alternatively spliced gene, different exons are spliced together, resulting in a different sequence. As with the detection of SNV, the methods of the invention can be readily applied to detection of an alternatively spliced mRNA. As described herein, the methods are based on using a probe that is specific to a target nucleic acid that detects the nucleic acid variation. In the case of SNV, the variation is a single nucleotide, whereas in the case of an alternatively spliced gene, the sequence variation can include numerous different nucleotides, that is, a different sequence, as a result of a different junction between two exons. In this case, the SP probe can be designed to span the variant junction sequence, preferably placing the junction near the center of SPAT. Alternatively, the variant junction point can be placed between NPAT and SPAT.

In addition, to detecting splice variants, the methods of the invention can be used to detect gene rearrangements. It is well known that many cancers are characterized by gene rearrangements, in which oncogenes are activated or growth repressors are inactivated. Similar to transcript/RNA splicing, the gene rearrangement results in a sequence variation from a non-rearranged gene. When transcribed, the mRNA also contains the sequence variation as fusion transcripts. As with detecting RNA splicing, the methods of the invention can be readily applied to detect gene rearrangements or fusion transcripts. For example, the SP probe can be designed to span the variant junction sequence in the rearranged DNA or the fusion transcript, preferably placing the junction point near the center of SPAT. Alternatively, the variant junction can be placed between NPAT and SPAT. A similar strategy can be employed to detect insertions and deletions. For example, the point of an insertion or deletion can be placed within SPAT, preferably near the center of SPAT. Alternatively, the point of insertion or deletion can be placed between NPAT and SPAT.

Figure 10A:
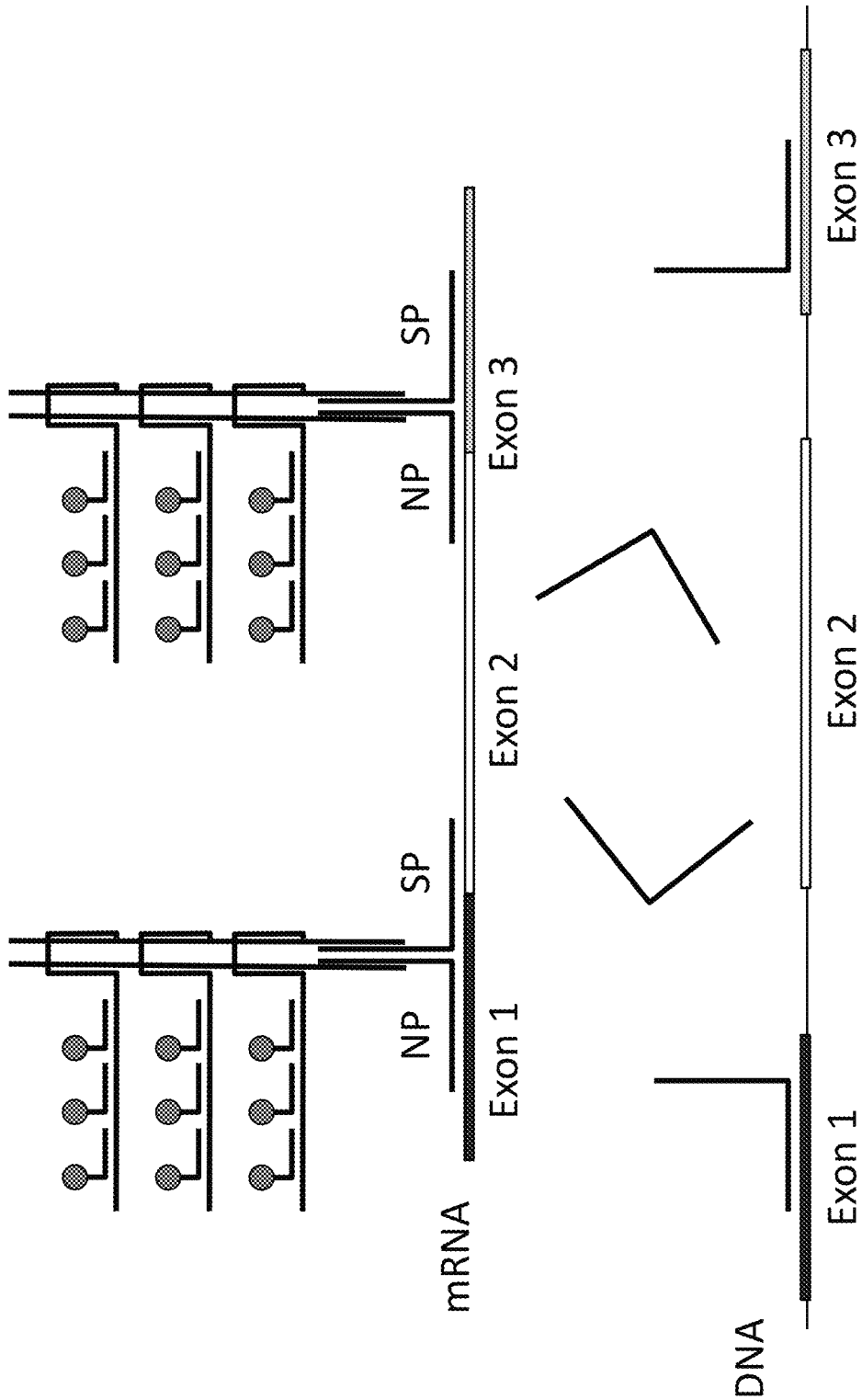
FIGS. 10A-10C show exemplary embodiments of utilizing splice junction detection methods to detect RNA molecules while avoiding the detection of corresponding DNA.

In a similar manner as detecting splice variants and gene rearrangements, the methods of the invention can be adopted to detect RNA specifically without detecting the corresponding DNA in the same cell. FIG. 10A shows a different approach, where the SPAT on SP bridges across the junction of two adjacent exons. With the exons adjacent to each other in the mRNA, SP can bind to the target nucleic acid right next to the NP, providing for assembly of the SGC on the target nucleic acid. With the exons spaced widely apart in DNA, the SP cannot bind to the target nucleic acid, and therefore SGC cannot form, leading to the absence of signal.

Figure 10B:
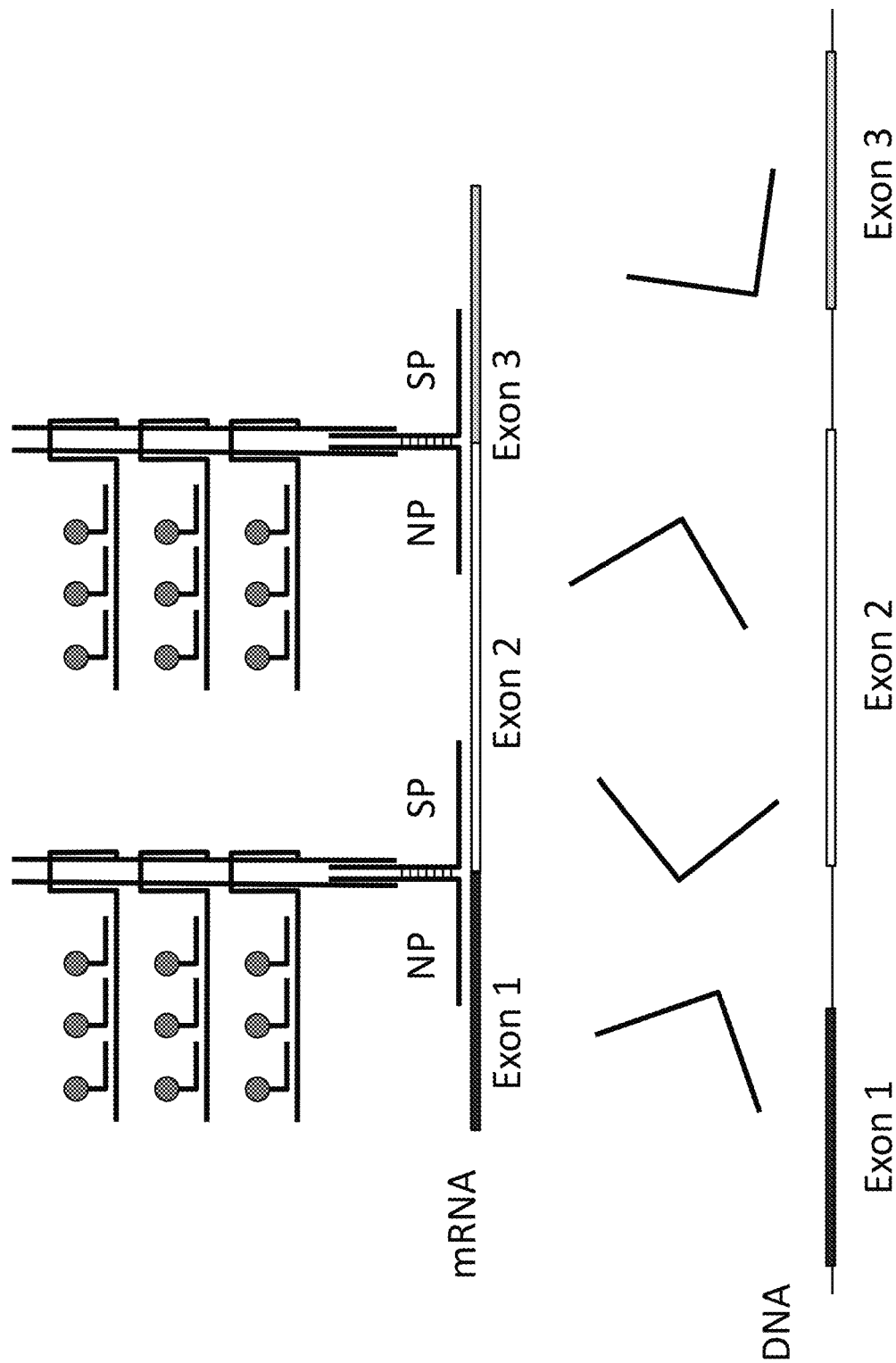
Figure 10C:
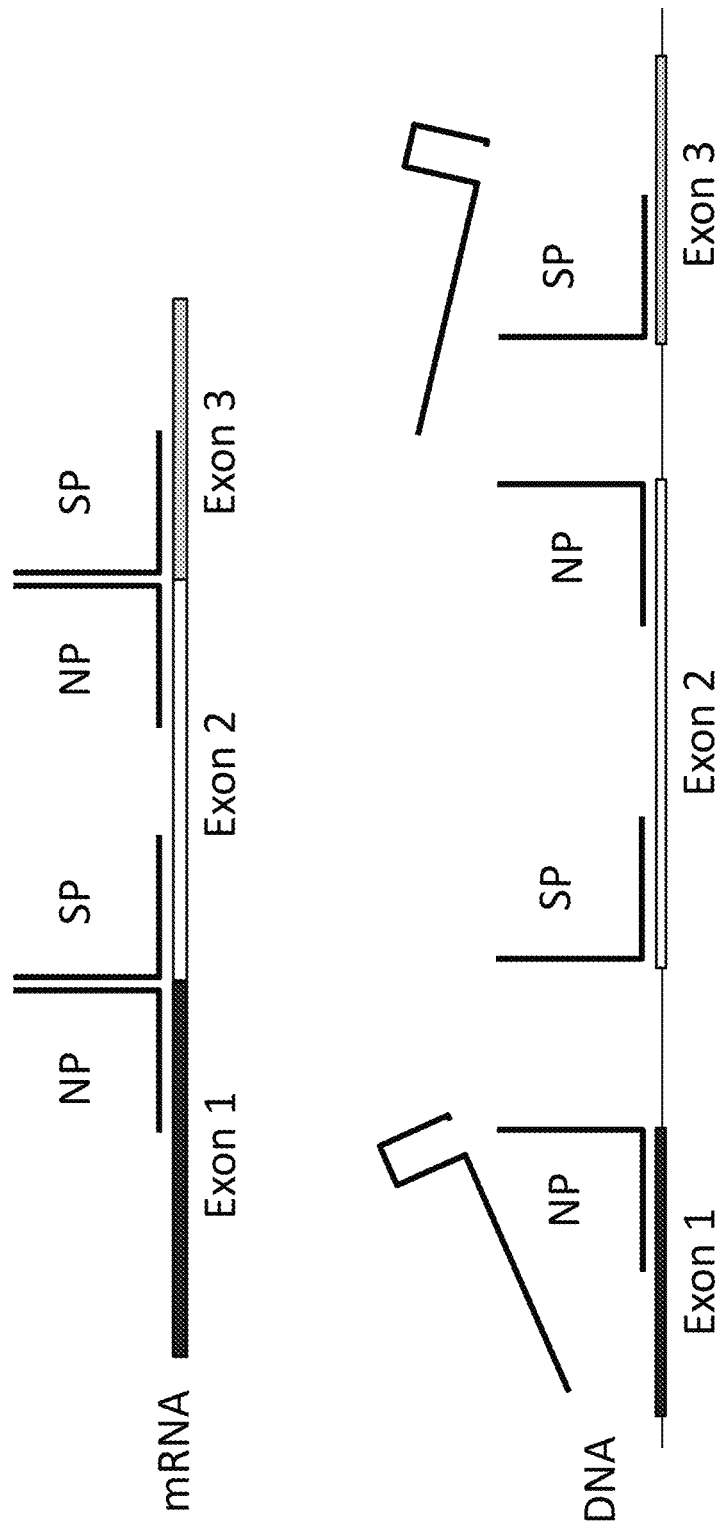

Another embodiment is illustrated in FIG. 10B. In this embodiment, the SP and NP have collaborative hybridization with each other, as depicted in FIG. 8B, where the SP and NP can only stably bind to the target nucleic acid when they hybridize to the target nucleic acid and each other simultaneously. The SP and NP cannot bind to the DNA because the SP and NP binding sites are not adjacent as in the mRNA. As shown in FIG. 10B, the SP and NP are designed to each bind to separate exons at the site of an exon junction. The SP and NP can only bind stably to an mRNA target because the exons to which the SP and NP bind are only adjacent in the mRNA. Therefore, a stable SGC can be formed on the mRNA, leading to detectable signal. In the case of the DNA, the SP and NP cannot stably bind to the target nucleic acid, because the respective SP and NP binding sites are not adjacent in the DNA. In this situation, no SGC can be formed (see FIG. 10B). Another embodiment is shown in FIG. 10C, where the splice junction of exons are placed between SP and NP. As shown in FIGS. 10A, 10B and 10C, exons are separated in DNA but spliced together in the mRNA transcript, forming unique junctions in mRNA, which can be readily detected using the methods depicted in FIG. 9. Since the exons are separated in DNA, no stable SP-NP set will be hybridized adjacent to each other; no SGC can be formed, which leads to no detectable signal, as shown in FIG. 10C.

In another embodiment, the invention provides a method of in situ detection of a spliced target nucleic acid in a sample of fixed and permeabilized cells, comprising (A) contacting the sample with a splice site probe (SP) and a neighbor probe (NP), wherein the SP comprises a target anchor segment (SPAT) that can specifically hybridize to a region of the target nucleic acid comprising the splice site and a pre-amplifier anchor segment (SPAP), and wherein the NP comprises a target anchor segment (NPAT) that can hybridize to a region of the target nucleic acid adjacent to the binding site of the SP and a pre-amplifier anchor segment (NPAP); (B) contacting the sample with an SP pre-amplifier (SPM) and an NP pre-amplifier (NPM), wherein the SPM comprises a segment that can bind to the SP and comprises two or more SP collaboration anchors (SPCAs), and wherein the NPM comprises a segment that can bind to the NP and comprises two or more NP collaboration anchors (NPCAs); (C) contacting the sample with a collaboration amplifier (COM), wherein the COM comprises a first segment complementary to the SPCA, a second segment complementary to the NPCA, and a third segment comprising a plurality of label amplifier anchor segments; (D) contacting the sample with a label probe system (LPS), wherein the LPS comprises a plurality of label amplifiers (LMs) and a plurality of label probes (LPs), wherein each LM comprises a segment that can bind to a label amplifier anchor segment of the COM and a plurality of label probe anchor segments, wherein each LP comprises a detectable label and a segment that hybridizes to the label probe anchor segment of LM, wherein the aforesaid hybridizations form a signal generating complex (SGC) comprising a target nucleic acid with the splice site, an SP, an NP, an SPM, an NPM, a plurality of COMs, a plurality of LMs, and a plurality of LPs; and (E) detecting in situ signal from the SGC on the sample. In one embodiment, the SPAT can specifically hybridize to one of the two spliced nucleic acid segments. In another embodiment, the SPAT can specifically hybridize to both of the two spliced nucleic acid segments.

In another embodiment, the invention provides a sample of fixed and permeabilized cells, comprising (A) at least one fixed and permeabilized cell containing a spliced target nucleic acid; (B) a splice site probe (SP) comprising a target anchor segment (SPAT) hybridized to a region of the target nucleic acid comprising the splice site, and, a neighbor probe (NP) comprising a target anchor segment (NPAT) hybridized to a region of the target nucleic acid adjacent to the binding site of the SP; (C) an SP pre-amplifier (SPM) hybridized to the SP, wherein the SPM comprises a plurality of SP collaboration anchors (SPCAs), and, an NP pre-amplifier (NPM) hybridized to the NP, wherein the NPM comprises a plurality of NP collaboration anchors (NPCAs); (D) a plurality of collaboration amplifiers (COMs) each hybridized to the SPM and the NPM, wherein each COM comprises a first segment complementary to the SPCA, a second segment complementary to the NPCA, and third segment comprising a plurality of label amplifier anchor segments; (E) a plurality of label amplifiers (LMs) each hybridized to a label amplifier anchor segment of the COM, wherein the LM comprises a plurality of label probe anchor segments; and (F) a plurality of label probes (LPs) each hybridized to a label probe anchor segment of the LM, wherein the LP comprises a detectable label; wherein the aforesaid hybridizations form a signal generating complex (SGC) comprising the target nucleic acid with the splice site, an SP, an NP, an SPM, an NPM, a plurality of COMs, a plurality of LMs, and a plurality of LPs, and wherein the SGC provides a signal that is detectable and distinguishable from the background noise.

In another embodiment, the invention provides a tissue slide, comprising (A) a slide having immobilized thereon a plurality of fixed and permeabilized cells comprising at least one fixed and permeabilized cell containing a spliced target nucleic acid; (B) a splice site probe (SP) comprising a target anchor segment (SPAT) hybridized to a region of the target nucleic acid comprising the splice site, and, a neighbor probe (NP) comprising a target anchor segment (NPAT) hybridized to a region of the target nucleic acid adjacent to the binding site of the SP; (C) an SP pre-amplifier (SPM) hybridized to the SP, wherein the SPM comprises a plurality of SP collaboration anchors (SPCAs), and, an NP pre-amplifier (NPM) hybridized to the NP, wherein the NPM comprises a plurality of NP collaboration anchors (NPCAs); (D) a plurality of collaboration amplifiers (COMs) each hybridized to the SPM and the NPM, wherein each COM comprises a first segment complementary to the SPCA, a second segment complementary to the NPCA, and a third segment comprising a plurality of label amplifier anchor segments; (E) a plurality of label amplifiers (LMs) each hybridized to a label amplifier anchor segment of the COM, wherein the LM comprises a plurality of label probe anchor segments; and (F) a plurality of label probes (LPs) each hybridized to a label probe anchor segment of the LM, wherein the LP comprises a detectable label; wherein the aforesaid hybridizations form a signal generating complex (SGC) comprising the target nucleic acid with the splice site, an SP, an NP, an SPM, an NPM, a plurality of COMs, a plurality of LMs, and a plurality of LPs, and wherein the SGC provides a signal that is detectable and distinguishable from the background noise.

In another embodiment, the invention provides a kit for in situ detection of a spliced target nucleic acid in a sample of fixed and permeabilized cells, comprising (A) at least one reagent for permeabilizing cells; (B) a set of target hybridizing probes comprising a splice site probe (SP) comprising a target anchor segment (SPAT) capable of hybridizing to a region of the target nucleic acid comprising the splice site, and, a neighbor probe (NP) comprising a target anchor segment (NPAT) capable of hybridizing to a region of the target nucleic acid adjacent to the binding site of the SP; (C) a set of pre-amplifiers comprising an SP pre-amplifier (SPM) comprising a segment capable of hybridizing to the SP, wherein the SPM comprises a plurality of SP collaboration anchors (SPCAs), and, an NP pre-amplifier (NPM) comprising a segment capable of hybridizing to the NP, wherein the NPM comprises a plurality of NP collaboration anchors (NPCAs); (D) a collaboration amplifier (COM) capable of hybridizing to the SPM and the NPM, wherein the COM comprises a first segment complementary to the SPCA, a second segment complementary to the NPCA, and a third segment comprising a plurality of label amplifier anchor segments; (E) a label amplifier (LM) capable of hybridizing to the label amplifier anchor segment of the COM, wherein the LM comprises a plurality of label probe anchor segments; and (F) a label probe (LP) capable of hybridizing to the label probe anchor segment of the LM, wherein the LP comprises a detectable label; wherein, upon contacting a sample of fixed and permeabilized cells comprising a cell containing a target nucleic acid with the splice site, the components in aforesaid (B)-(F) form a signal generating complex (SGC) comprising the target nucleic acid with the splice site, an SP, an NP, an SPM, an NPM, a plurality of COMs, a plurality of LMs, and a plurality of LPs, and wherein the SGC provides a signal that is detectable and distinguishable from the background noise.

Figure 11A:
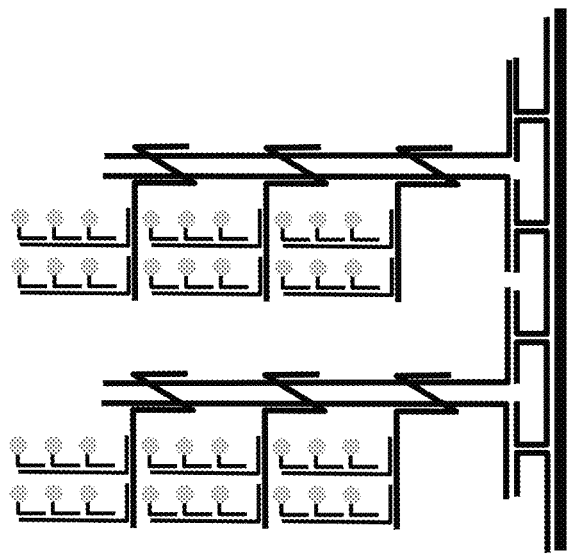
FIGS. 11A, 11B and 11C show exemplary embodiments of detection of short sequence.
Figure 11B:
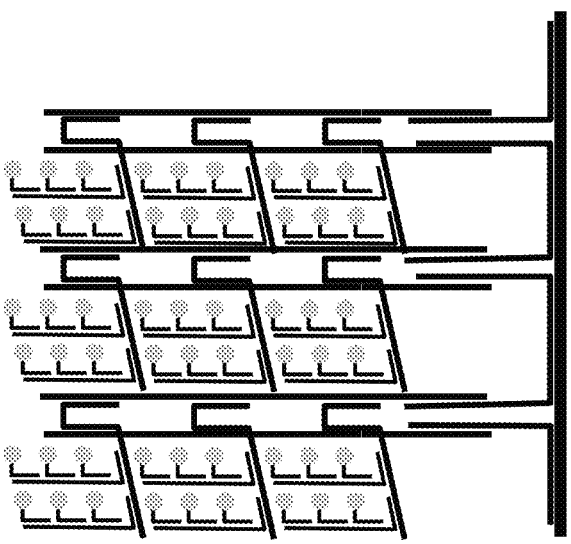
Figure 11C:
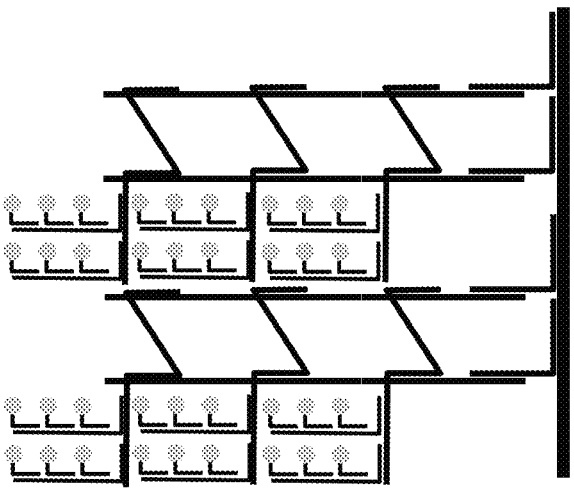

Previously described in situ nucleic acid detection methods have difficulty detecting nucleic acid sequences shorter than 300 to 150 bases. In the present invention, since a detectable signal can be generated with a single SGC and the combined length of SPAT and NPAT can be as short as 20 bases, the methods of the invention can be readily adapted to detect short or substantially broken nucleic acid sequence, such as microRNA, micro-insertion or micro-deletion. For detection of short or substantially broken nucleic acid sequence, target probe (TP) sets, analogous to the SP-NP sets described herein, are designed to hybridize specifically to adjacent, non-overlapping regions on the target nucleic acid, similar to the function of target probe sets containing both SP and NP, as described herein. In general, the segment of the target probe that binds to the target nucleic acid, TPAT, analogous to SPAT and NPAT, have the same or similar length. If the target sequence is longer, multiple TP sets can be used with multiple SGCs as shown in FIG. 11. The use of multiple SGCs in this situation can be used either to increase the detection sensitivity or to increase the detection robustness since any one of the multiple SGCs successfully formed on the target can generate a detectable signal. Such configurations are particularly useful in detecting long but highly degraded nucleic acid targets. Many sets of TPs can be designed to be complementary to non-overlapping regions of the target nucleic acid. Because the target nucleic acid is in a highly degraded state, only a limited number of short segments are accessible. A detectable signal can be generated as long as one TP pair can be successfully hybridized to the target sequence. FIG. 11 depicts three exemplary configurations. In FIG. 11A, there is one TP pair in an SGC. The maximum number of SGCs that can be accommodated has to be at least multiple lengths of SPAT+ NPAT. In FIG. 11B, at least one TP of one SGC contains two TPAT segments that bind to non-overlapping regions of the target nucleic acid, analogous to the integration of an SP and NP into a single probe. In the configuration depicted in FIG. 11B, the maximum number of SGCs within the same length of target sequence can be increased compared to the configuration shown in FIG. 11A, improving the sensitivity and/or robustness of the detection. All single SGC configuration and component orientation options shown in FIGS. 1 to 8 can similarly be expanded to a multiple SGC setting to detect longer target sequences. For example, FIG. 11C depicts multiple SGCs in a similar configuration to that shown in FIG. 8A when the spatial flexibility of nucleic acid molecules are taken into consideration.

Figures 12A, 12B:
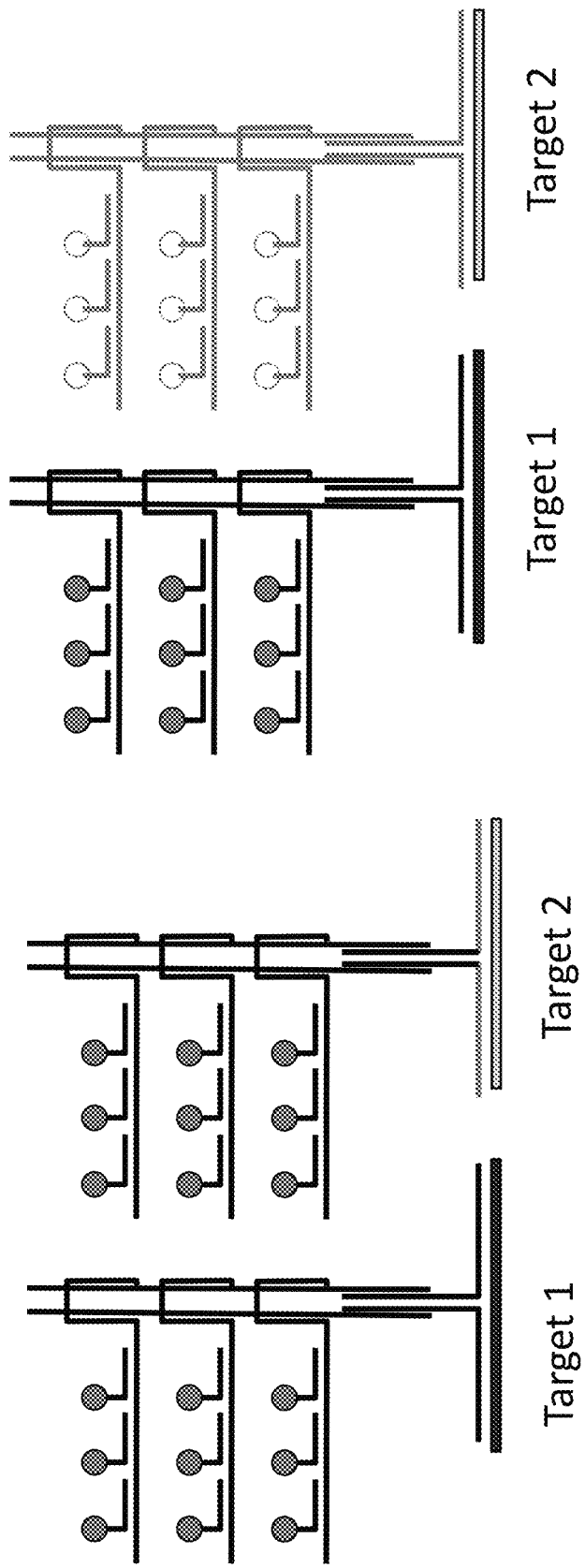
FIGS. 12A and 12B show exemplary embodiments of detection of multiple targets.

In many applications, it is highly desirable to detect multiple targets in the same assay. This present invention provides two different approaches to meet this requirement. The first approach is pooling, where, as shown in FIG. 12A, a SGC is assembled for each target, in which unique NPAT and SPAT are provided for each target, and NPAP and SPAP are the same across different NP and SP sets for each target. This allows all other components of the SGC, that is, NPM, SPM, COM and LPS, to be the same for all SGCs. The pooling provides one detectable signal when any one of multiple targets are present in the sample and is very useful when a group of targets provide the same or similar biological or clinical utility. The second approach is multiplexing, where, as shown in FIG. 12B, a SGC is assembled for each target and components of each SGC are unique for that SGC and sequences of these components are designed to ensure that there is no cross-hybridization between different SGCs. Since the label probe (LP) in each SGC has a unique, distinguishable label, a different, uniquely distinguishable signal can be detected for the presence of each target. The multiplexing approach is useful in applications where different targets provide different biological or clinical utility. It is understood that the pooling and multiplexing approaches can be used in combination to detect multiple groups of targets.

In another embodiment, the invention provides a method of in situ detection of a target nucleic acid, wherein the target nucleic acid is 300 or fewer bases in length, in a sample of fixed and permeabilized cells. Such a method can comprise the steps of (A) contacting the sample with a set of target probes (TPs), wherein the set comprises at least two target probes, wherein each TP comprises a target anchor segment (TPAT) that can specifically hybridize to a region of the target nucleic acid and a pre-amplifier anchor segment (TPAP), wherein the set comprises pairs of TPs that can bind to adjacent, non-overlapping regions of the target nucleic acid; (B) contacting the sample with a set of TP pre-amplifiers (TPMs), wherein the set comprises at least one pair of TPMs, wherein each TPM comprises a segment that can bind to one member of the pair of TPs that bind to adjacent regions of the target nucleic acid, and wherein each TPM comprises two or more TP collaboration anchors (TPCAs); (C) contacting the sample with a collaboration amplifier (COM), wherein the COM comprises a first segment complementary to the TPCA of one member of the pair of TPMs, a second segment complementary to the TPCA of the second member of the pair of TPMs, and a third segment comprising a plurality of label amplifier anchor segments; (D) contacting the sample with a label probe system (LPS), wherein the LPS comprises a plurality of label amplifiers (LMs) and a plurality of label probes (LPs), wherein each LM comprises a segment that can bind to a label amplifier anchor segment of the COM and a plurality of label probe anchor segments, wherein each LP comprises a detectable label and a segment that hybridizes to the label probe anchor segment of LM, wherein the aforesaid hybridizations form a signal generating complex (SGC) comprising the target nucleic acid, at least one pair of TPs, at least one pair of TPMs, a plurality of COMs, a plurality of LMs, and a plurality of LPs; and (E) detecting in situ signal from the SGC on the sample.

In a particular embodiment, the target probe set comprises a splice site probe, SP and a neighbor probe, NP. The SP comprises a SPAT capable of hybridizing to a region of the target nucleic acid containing a splice site, J, and another region, SPAP, capable of hybridizing to a segment on the SP pre-amplifier (SPM). The NP comprises an NPAT capable of hybridizing to a region of the target nucleic acid adjacent to the region hybridized to SPAT and another region, NPAP, capable of hybridizing to a segment on the NP pre-amplifier (NPM). The SPM and NPM additionally comprise one or more segments of SPCAs and NPCAs, respectively. One or more collaboration amplifiers, COM, are provided, wherein each comprises a first segment complementary to the SPCA, a second segment complementary to the NPCA, and a third segment comprising a plurality of label amplifier anchor segments. Each COM can attach to NPM and SPM stably when, and only when, the NPCA and SPCA are present close together so that it hybridizes to NPCA and SPCA collaboratively. Multiple label amplifiers (LM) capable of hybridizing to the label amplifier anchor segment of the COM are provided, wherein the LM comprises a plurality of label probe anchor segments. Multiple label probes (LP) are provided capable of hybridizing to the label probe anchor segment of the LM, wherein the LP comprises a detectable label. The SPM, NPM, COM, LM and LP form a signal generating complex (SGC) that contain sufficient number of labels capable being detected. Each SGC can appear in an imaging system as a signal focus. If the specific splice junction does not exist, that is, the two target segments are not spliced together, SP will not hybridize adjacent to NP, SPM will not be present close to NPM, which will not allow COM to be stably captured to the target, and SGC will not be formed; thus, no signal can be detected.

In one embodiment, the invention provides method of in situ detection of a nucleotide variation of a target nucleic acid in a sample of fixed and permeabilized cells, comprising: (A) contacting the sample with a nucleotide variation probe (SP) and a neighbor probe (NP), wherein the SP comprises a target anchor segment (SPAT) that can specifically hybridize to a region of the target nucleic acid comprising the nucleotide variation and a pre-amplifier anchor segment (SPAP), and wherein the NP comprises a target anchor segment (NPAT) that can hybridize to a region of the target nucleic acid adjacent to the binding site of the SP and a pre-amplifier anchor segment (NPAP); (B) contacting the sample with an SP pre-amplifier (SPM) and an NP pre-amplifier (NPM), wherein the SPM comprises a segment that can bind to the SP and comprises two or more SP collaboration anchors (SPCAs), and wherein the NPM comprises a segment that can bind to the NP and comprises two or more NP collaboration anchors (NPCAs); (C) contacting the sample with a collaboration amplifier (COM), wherein the COM comprises a first segment complementary to the SPCA, a second segment complementary to the NPCA, and a third segment comprising a plurality of label amplifier anchor segments; (D) contacting the sample with a label probe system (LPS), wherein the LPS comprises a plurality of label amplifiers (LMs) and a plurality of label probes (LPs), wherein each LM comprises a segment that can bind to a label amplifier anchor segment of the COM and a plurality of label probe anchor segments, wherein each LP comprises a detectable label and a segment that hybridizes to the label probe anchor segment of LM, wherein the aforesaid hybridizations form a signal generating complex (SGC) comprising a target nucleic acid with the nucleotide variation, an SP, an NP, an SPM, an NPM, a plurality of COMs, a plurality of LMs, and a plurality of LPs; and (E) detecting in situ signal from the SGC on the sample.

In another embodiment, the invention provides a sample of fixed and permeabilized cells, comprising: (A) at least one fixed and permeabilized cell containing a target nucleic acid with a nucleotide variation; (B) a nucleotide variation probe (SP) comprising a target anchor segment (SPAT) hybridized to a region of the target nucleic acid comprising the nucleotide variation, and, a neighbor probe (NP) comprising a target anchor segment (NPAT) hybridized to a region of the target nucleic acid adjacent to the binding site of the SP; (C) an SP pre-amplifier (SPM) hybridized to the SP, wherein the SPM comprises a plurality of SP collaboration anchors (SPCAs), and, an NP pre-amplifier (NPM) hybridized to the NP, wherein the NPM comprises a plurality of NP collaboration anchors (NPCAs); (D) a plurality of collaboration amplifiers (COMs) each hybridized to the SPM and the NPM, wherein each COM comprises a first segment complementary to the SPCA, a second segment complementary to the NPCA, and third segment comprising a plurality of label amplifier anchor segments; (E) a plurality of label amplifiers (LMs) each hybridized to a label amplifier anchor segment of the COM, wherein the LM comprises a plurality of label probe anchor segments; and (F) a plurality of label probes (LPs) each hybridized to a label probe anchor segment of the LM, wherein the LP comprises a detectable label; wherein the aforesaid hybridizations form a signal generating complex (SGC) comprising the target nucleic acid with the nucleotide variation, an SP, an NP, an SPM, an NPM, a plurality of COMs, a plurality of LMs, and a plurality of LPs, and wherein the SGC provides a signal that is detectable and distinguishable from the background noise.

In another embodiment, the invention provides a tissue slide, comprising: (A) a slide having immobilized thereon a plurality of fixed and permeabilized cells comprising at least one fixed and permeabilized cell containing a target nucleic acid with a nucleotide variation; (B) a nucleotide variation probe (SP) comprising a target anchor segment (SPAT) hybridized to a region of the target nucleic acid comprising the nucleotide variation, and, a neighbor probe (NP) comprising a target anchor segment (NPAT) hybridized to a region of the target nucleic acid adjacent to the binding site of the SP; (C) an SP pre-amplifier (SPM) hybridized to the SP, wherein the SPM comprises a plurality of SP collaboration anchors (SPCAs), and, an NP pre-amplifier (NPM) hybridized to the NP, wherein the NPM comprises a plurality of NP collaboration anchors (NPCAs); (D) a plurality of collaboration amplifiers (COMs) each hybridized to the SPM and the NPM, wherein each COM comprises a first segment complementary to the SPCA, a second segment complementary to the NPCA, and a third segment comprising a plurality of label amplifier anchor segments; (E) a plurality of label amplifiers (LMs) each hybridized to a label amplifier anchor segment of the COM, wherein the LM comprises a plurality of label probe anchor segments; and (F) a plurality of label probes (LPs) each hybridized to a label probe anchor segment of the LM, wherein the LP comprises a detectable label; wherein the aforesaid hybridizations form a signal generating complex (SGC) comprising the target nucleic acid with the nucleotide variation, an SP, an NP, an SPM, an NPM, a plurality of COMs, a plurality of LMs, and a plurality of LPs, and wherein the SGC provides a signal that is detectable and distinguishable from the background noise.

In another embodiment, the invention provides a kit for in situ detection of a nucleotide variation of a target nucleic acid in a sample of fixed and permeabilized cells, comprising: (A) at least one reagent for permeabilizing cells; (B) a set of target hybridizing probes comprising a nucleotide variation probe (SP) comprising a target anchor segment (SPAT) capable of hybridizing to a region of the target nucleic acid comprising the nucleotide variation, and, a neighbor probe (NP) comprising a target anchor segment (NPAT) capable of hybridizing to a region of the target nucleic acid adjacent to the binding site of the SP; (C) a set of pre-amplifiers comprising an SP pre-amplifier (SPM) comprising a segment capable of hybridizing to the SP, wherein the SPM comprises a plurality of SP collaboration anchors (SPCAs), and, an NP pre-amplifier (NPM) comprising a segment capable of hybridizing to the NP, wherein the NPM comprises a plurality of NP collaboration anchors (NPCAs); (D) a collaboration amplifier (COM) capable of hybridizing to the SPM and the NPM, wherein the COM comprises a first segment complementary to the SPCA, a second segment complementary to the NPCA, and a third segment comprising a plurality of label amplifier anchor segments; (E) a label amplifier (LM) capable of hybridizing to the label amplifier anchor segment of the COM, wherein the LM comprises a plurality of label probe anchor segments; and (F) a label probe (LP) capable of hybridizing to the label probe anchor segment of the LM, wherein the LP comprises a detectable label; wherein, upon contacting a sample of fixed and permeabilized cells comprising a cell containing a target nucleic acid with the nucleotide variation, the components in aforesaid (B)-(F) form a signal generating complex (SGC) comprising the target nucleic acid with the nucleotide variation, an SP, an NP, an SPM, an NPM, a plurality of COMs, a plurality of LMs, and a plurality of LPs, and wherein the SGC provides a signal that is detectable and distinguishable from the background noise. In particular embodiments of the above described embodiments of the invention, the nucleotide variation is selected from the group consisting of a single nucleotide variation, a multi-nucleotide variation, a splice site, an insertion, a deletion, a rearrangement, and the like.

It is understood that modifications which do not substantially affect the activity of the various embodiments of this invention are also provided within the definition of the invention provided herein. Accordingly, the following examples are intended to illustrate but not limit the present invention.

Example I

Detection of Point Mutations

This example describes two exemplary applications of the invention in detecting point mutations in tissue samples.

FIG. 13 shows detection of BRAF mRNA in sections of formalin fixed and paraffin embedded (FFPE) pellet of melanoma cell lines. Melanoma cell lines negative (CHL-1, a and a') and positive (SK-MEL-28, b and b') for the V600E point mutation of BRAF were assayed. Cells were hybridized to a target probe system (TPS) containing the wild type detection probe (WDP, sequence: gagatttcA*ctgtagc (SEQ ID NO: 1), A* is a BNA modified base) (a and b) and a TPS containing a BRAF V600E mutation detection probe (MDP, sequence: gagatttcT*ctgtagc (SEQ ID NO: 2), T* is a BNA modified base) (a' and b') separately. An SGC configuration substantially similar to the one shown in FIG. 1 was used. Signal with probe targeting wild type BRAF was observed in wild type cells only (a) while V600E mutation was detected in V600E positive cells only with V600E MDP (b').

Figures 14A, 14B:
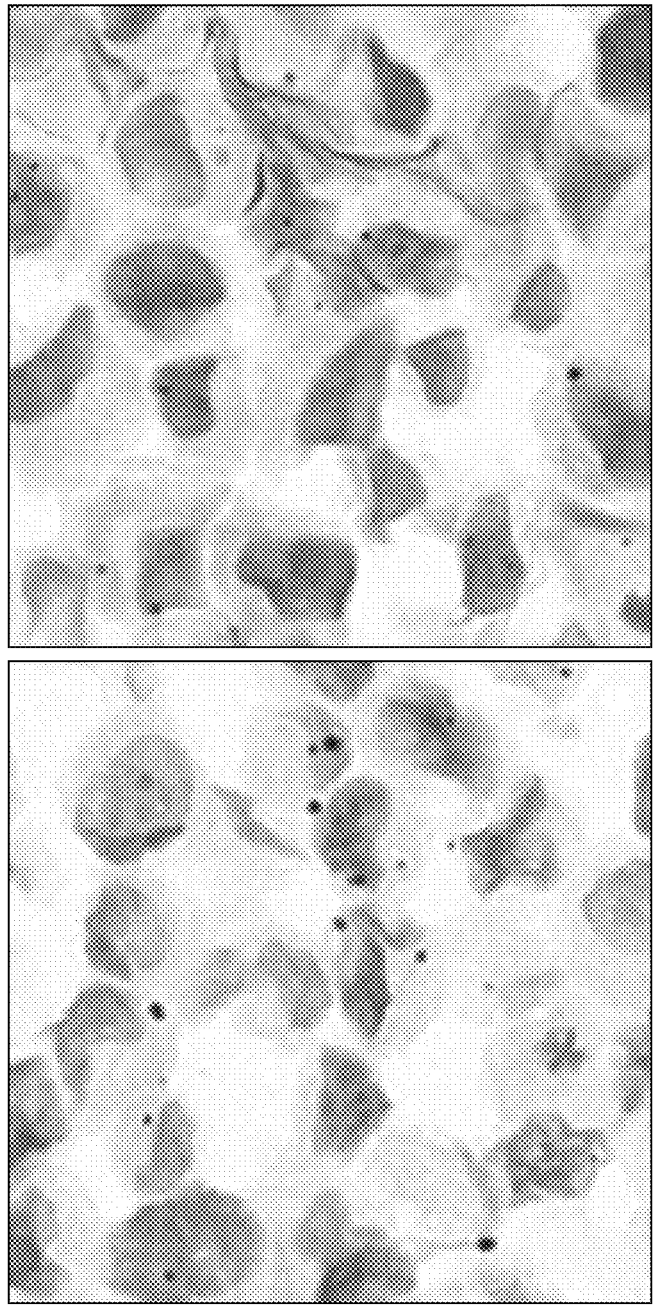
FIGS. 14A and 14B show the effect of SPATs of various lengths.

FIG. 14 shows the effect of SPATs of various lengths, where an SGC configuration substantially similar to the one shown in FIG. 1 was used. In FIG. 14A, CHL-1 cells (no V600E mutation) were hybridized with a V600E mutation probe having a 22 nucleotide (nt) SPAT and showed false positive signal. Thus, FIG. 14A shows a high number of false positives with the use of a long SPAT. In FIG. 14B, SK-MEL-28 cells containing a V600E mutation were hybridized with a 15nt SPAT V600E mutation probe, and it showed specific signals. Thus, FIG. 14B shows that the assay has higher specificity with shorter SPAT.

Figures 15A, 15B:
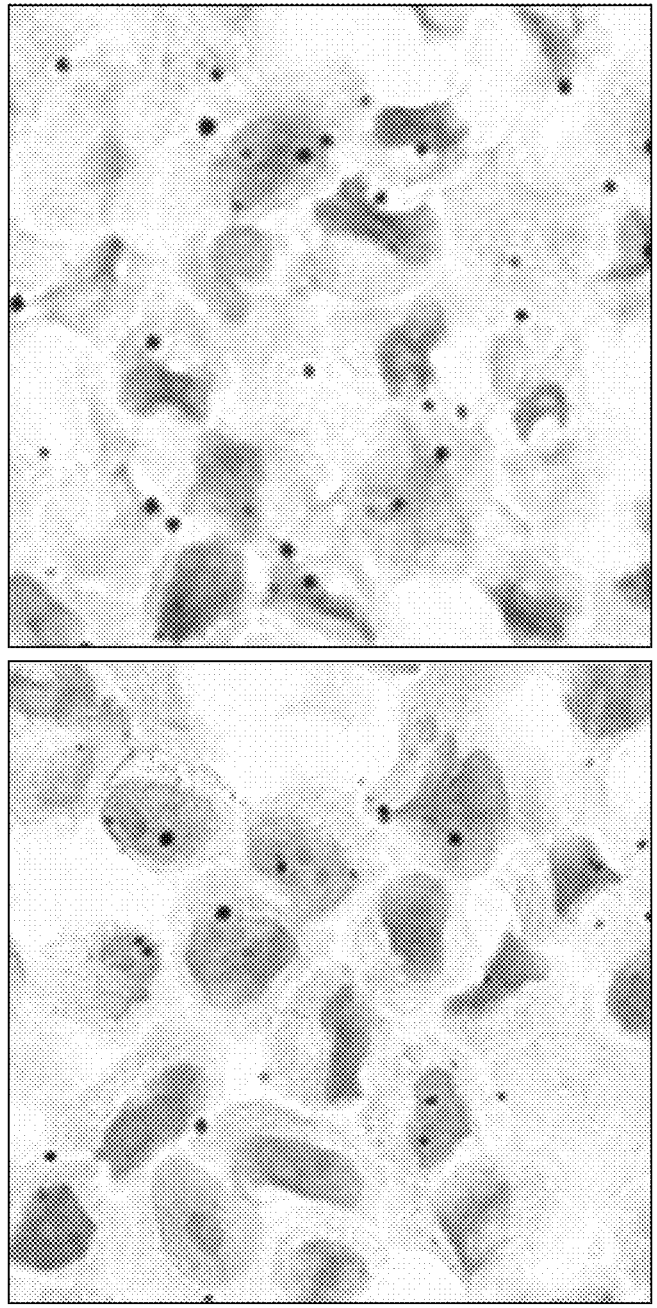
FIGS. 15A and 15B show the effect of including modified bases in a SPAT.

FIG. 15 shows the effect of including modified bases in a SPAT, where an SGC configuration substantially similar to the one shown in FIG. 1 was used. In FIG. 15A, SK-MEL-28 cells (containing V600E mutation) were hybridized with a 16nt SPAT V600E probe with normal bases. FIG. 15A thus shows staining results with normal bases in SPAT. In FIG. 15B, SK-MEL-28 cells were hybridized with a 16nt SPAT V600E mutation probe containing a single modified BNA base complementary to the mutation and showed improved sensitivity with more signals (dots). FIG. 15B thus shows improved results with modified bases used in SPAT.

FIG. 16 shows detection of BRAF mRNA in 2 FFPE colon cancer tissues known to be negative (a and a') and positive (b and b') for the V600E point mutation, where an SGC configuration substantially similar to the one shown in FIG. 1 was used. While signals were observed in both samples with probe targeting wild type BRAF mRNA (a and b), V600E mutation mRNA was detected only in the mutation positive sample with probe designed specifically for V600E mutation (b'). The presence of WDP signals in the second sample indicated that it had a heterozygous BRAF V600E mutation. In all SNV probes designed in the examples shown in FIG. 16, a single BNA modified base was incorporated in SPAT at the location complementary to the mutation site.

Figures 17A, 17B:
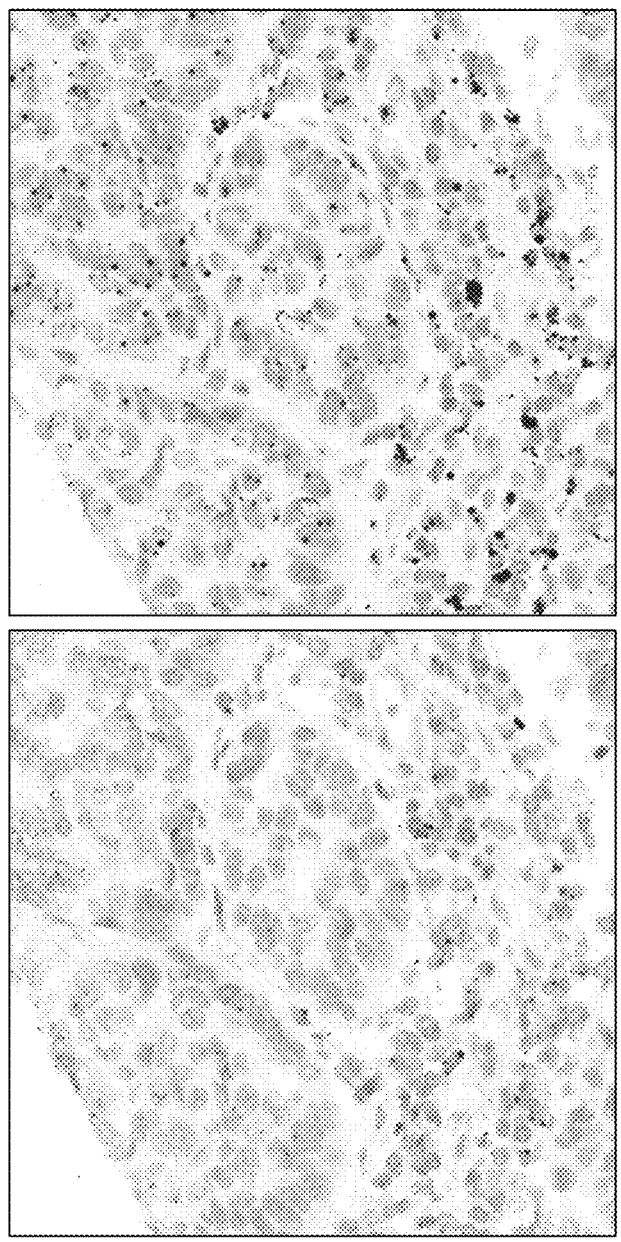
FIGS. 17A and 17B show the detection of very low abundant and/or degraded RNA target.

FIG. 17 shows the detection of very low abundant and degraded RNA. The target was HGF mRNA, which is more than 1000nt in length but was known to be expressed at a very low level. In addition, the RNA was known to be at least partially degraded in this sample, which is lung cancer in formalin-fixed, paraffin embedded (FFPE) tissue sections. FIG. 17A shows the staining image using methods as described in U.S. Pat. Nos. 7,709,198 and 8,658,361 and a target probe set containing 30 pairs of TPs. The detection sensitivity was low due to a combination of low expression and partial RNA degradation. FIG. 17B shows improved staining using the method of the invention with 30 pairs of TPs and an SGC configuration similar to that shown in FIG. 11A.

Figures 18A, 18B:
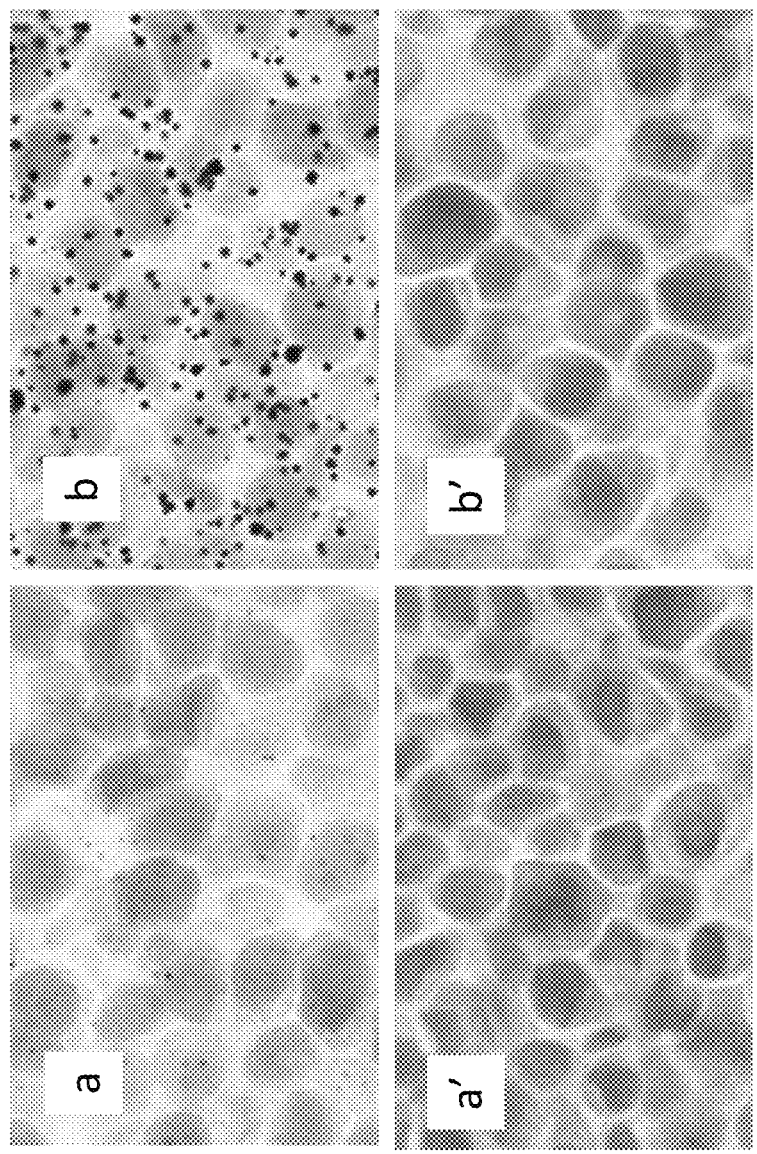
In FIG. 18A, the detection system of U.S. Pat. Nos. 7,709,198 and 8,658,361 was used with a single pair of target probes to detect 50nt sequence on POLR2A mRNA in Hela cell pellet.
In FIG. 18B, a single SGC with a configuration similar to that shown in FIG. 11A was used to detect the same target in the same sample type.

FIG. 18 demonstrates that the invention disclosed herein provides enhanced performance in detection of short nucleic acid targets compared to previously disclosed methods. In FIG. 18A, the detection system disclosed in U.S. Pat. Nos. 7,709,198 and 8,658,361 was used with a single pair of target probes to detect an approximately 50nt sequence on POLR2A mRNA in Hela cell pellet. FIG. 18A(a) represents the signal generated using POLR2A target probe. FIG. 18A(a') represents the background level generated using a target probe against dapB, a negative control gene. In FIG. 18B, a single SGC with a configuration similar to that shown in FIG. 11A was used to detect the same target in the same sample type. FIG. 18B(b) represents the signal generated using one TP pair targeting the same sequence of POLR2A mRNA. FIG. 18B(b') represents the background level generated targeting dapB, a negative control gene.

The target probe pair in the previously disclosed methods and the method shown in FIG. 18B have the same configuration, that is, each probe comprises a segment binding to the target sequence and another segment binding to a member of the amplification system. In previously disclosed methods, this member is the preamplifier/amplifier (that is, two target probes in the pair bind to the same preamplifier/amplifier molecule). In the specific embodiment of the invention used in FIG. 18B, one member of the probe pair binds to NPM, the other binds to SPM. The target binding segments of the probe pair in both methods are the same. The difference occurs in the other segment. In the previously disclosed methods, the other segment (binding to the preamplifier/amplifier) is short, so that the preamplifier/amplifier binds to a single probe in the pair unstably. When and only when both members of the target probe pair are present next to each other, the preamplifier/amplifier would bind to both probes collaboratively in a stable status. In this specific embodiment for the method of the invention, the other section is longer, providing for NPM or SPM to bind NP and SP stably. No collaborative hybridization occurs between SP-SPM or NP-NPM. The collaborative hybridization in the method of the invention in this particular example shown in FIG. 18B occurs between COM and SPM+NPM.

Figure 19:
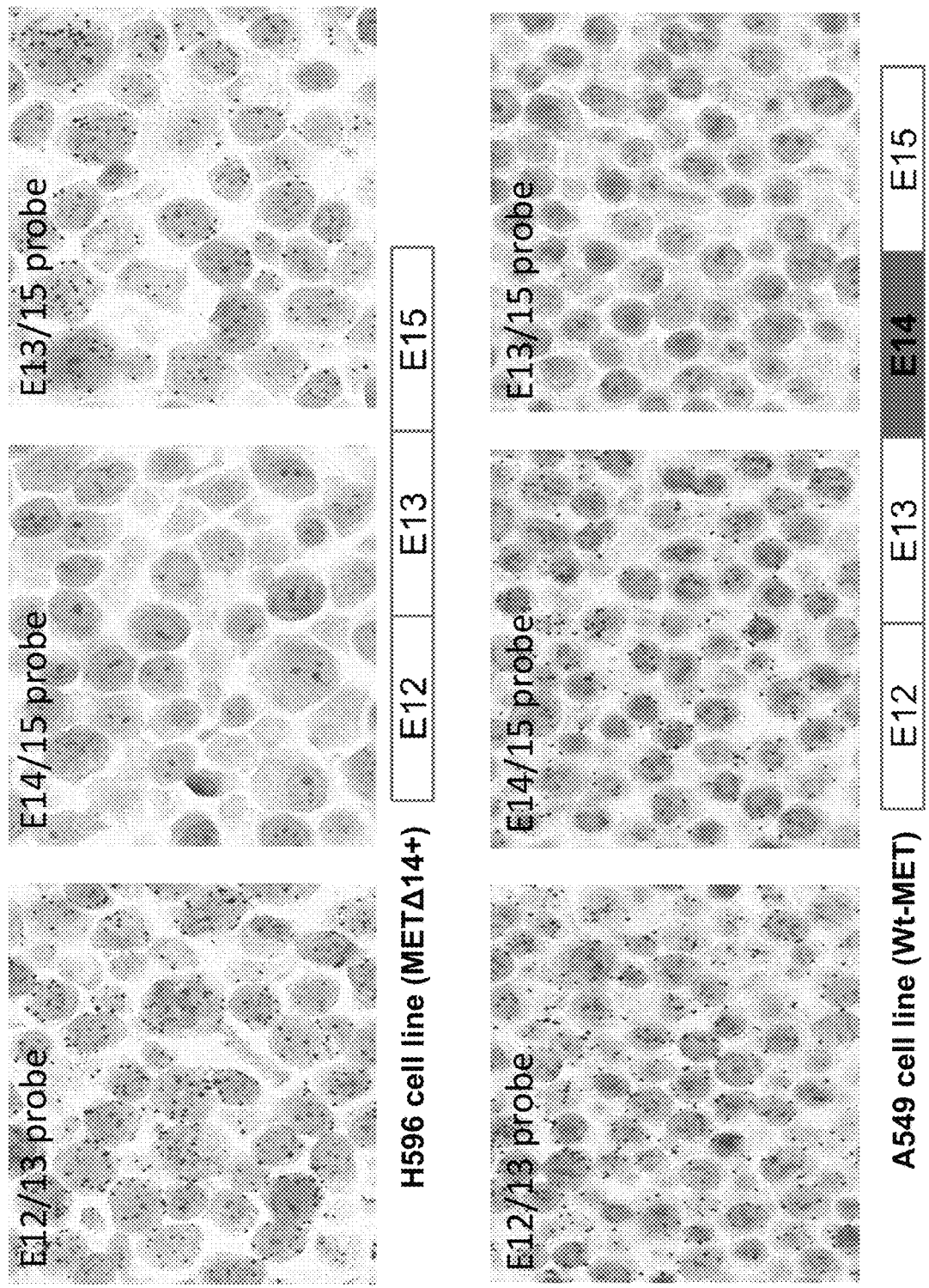
FIG. 19 demonstrates in situ detection of specific splice junctions, which can be used to identify a specific splice variant. Cell line H596 is known to be METΔ14 positive, that is, exon 14 in the MET gene is "skipped", resulting in exon 15 splicing with exon 13 in MET RNA. Cell line A549 is the wild-type having all exons 12-15 in MET RNA. Probes targeting splicing junctions E12/13, E13/14 and E14/15 were used to detect the presence of corresponding junctions in FFPE (formalin fixed and paraffin embedded) cell pellets of H596 and A549 cells. The staining images are shown in FIG. 19, which shows sensitive and specific detection of targeted splice junctions of E13/15 in H596 cells and E14/15 in A549 cells, showing that the METΔ14 splice variant was correctly identified.

FIG. 19 demonstrates in situ detection of specific splice junctions, which can be used to identify a specific splice variant. Cell line H596 is known to be METΔ14 positive, that is, exon 14 in the MET gene is "skipped", resulting in exon 15 splicing with exon 13 in MET RNA. Cell line A549 is the wild-type having all exons 12-15 in MET RNA. Probes targeting splicing junctions E12/13, E13/14 and E14/15 were used to detect the presence of corresponding junctions in FFPE (formalin fixed and paraffin embedded) cell pellets of H596 and A549 cells. The staining images are shown in FIG. 19, which show sensitive and specific detection of targeted splice junctions of E13/15 in H596 cells and E14/15 in A549 cells, showing that the METΔ14 splice variant was correctly identified.

These results demonstrate that the methods of utilizing collaborative hybridization can be used to detect single nucleotide variations in a target nucleic acid in an in situ assay.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of in situ detection of a single nucleotide variation of a target nucleic acid in a sample of cells, comprising:
   (A) contacting the sample, wherein the cells of the sample are fixed and permeabilized, with a single nucleotide variation probe and a neighbor probe, wherein the single nucleotide variation probe comprises: (i) a single nucleotide variation probe target anchor segment that can specifically hybridize to a region of the target nucleic acid comprising the single nucleotide variation but does not hybridize to a corresponding wild type or non-targeted single nucleotide variation sequence, and (ii) a single nucleotide variation probe pre-amplifier anchor segment; and wherein the neighbor probe comprises: (i) a neighbor probe target anchor segment that can hybridize to a region of the target nucleic acid adjacent to the binding site of the single nucleotide variation probe, and (ii) a neighbor probe pre-amplifier anchor segment;
   (B) contacting the sample with a single nucleotide variation probe pre-amplifier and a neighbor probe pre-amplifier, wherein the single nucleotide variation probe pre-amplifier comprises a segment complementary to the single nucleotide variation probe pre-amplifier anchor segment and further comprises two or more single nucleotide variation probe collaboration anchors, and wherein the neighbor probe pre-amplifier comprises a segment complementary to the neighbor probe pre-amplifier anchor segment and further comprises two or more neighbor probe collaboration anchors;

(C) contacting the sample with a collaboration amplifier, wherein the collaboration amplifier comprises a first segment complementary to the single nucleotide variation probe collaboration anchor, a second segment complementary to the neighbor probe collaboration anchor, and a third segment comprising a plurality of label amplifier anchor segments, wherein the collaboration amplifier cannot bind stably to either the single nucleotide variation probe collaboration anchor or the neighbor probe collaboration anchor alone;

(D) contacting the sample with a label probe system, wherein the label probe system comprises a plurality of label amplifiers and a plurality of label probes, wherein each label amplifier comprises: (i) a segment complementary to a label amplifier anchor segment of the collaboration amplifier, and (ii) a plurality of label probe anchor segments; wherein each label probe comprises a detectable label and a segment that hybridizes to the label probe anchor segment of label amplifier, wherein the aforesaid hybridizations form a signal generating complex comprising a target nucleic acid with the single nucleotide variation, a single nucleotide variation probe, a neighbor probe, a single nucleotide variation probe pre-amplifier, a neighbor probe preamplifier, a plurality of collaboration amplifiers, a plurality of label amplifiers, and a plurality of label probes;

(E) removing unbound probes, pre-amplifiers and amplifiers from the sample; and (F) detecting in situ signal from the signal generating complex on the sample, thereby detecting the single nucleotide variation of the target nucleic acid in the sample of cells.

2. The method of claim 1, wherein the target nucleic acid is RNA.

3. The method of claim 1, wherein the fixed and permeabilized cells are on a tissue slide.

4. The method of claim 1, wherein the single nucleotide variation probe target anchor segment is 10 to 20 nucleotides in length.

5. The method of claim 1, wherein the single nucleotide variation probe pre-amplifier anchor segment is 14 to 28 nucleotides in length.

6. The method of claim 1, wherein the single nucleotide variation probe comprises a spacer between the single nucleotide variation probe target anchor segment and the single nucleotide variation probe pre-amplifier anchor segment, wherein the spacer is 1 to 10 nucleotides in length.

7. The method of claim 1, wherein the neighbor probe target anchor segment is 16 to 30 nucleotides in length.

8. The method of claim 1, wherein the neighbor probe preamplifier anchor segment is 14 to 28 nucleotides in length.

9. The method of claim 1, wherein the neighbor probe comprises a spacer between the neighbor probe target anchor segment and the neighbor probe pre-amplifier anchor segment, wherein the spacer is 1 to 10 nucleotides in length.

10. The method of claim 1, wherein the single nucleotide variation probe pre-amplifier is 50 to 500 nucleotides in length.

11. The method of claim 1, wherein the neighbor probe preamplifier is 50 to 500 nucleotides in length.

12. The method of claim 1, wherein the single nucleotide variation probe collaboration anchor is 10 to 20 nucleotides in length.

13. The method of claim 1, wherein the single nucleotide variation probe pre-amplifier comprises a spacer between the two or more single nucleotide variation probe collaboration anchor, wherein the spacer between the single nucleotide variation probe collaboration anchor is independently 1 to 10 nucleotides in length.

14. The method of claim 1, wherein the neighbor probe collaboration anchor is 10 to 20 nucleotides in length.

15. The method of claim 1, wherein the neighbor probe preamplifier comprises a spacer between the two or more neighbor probe collaboration anchor, wherein the spacer between the neighbor probe collaboration anchor is independently 1 to 10 nucleotides in length.

16. The method of claim 1, wherein the collaboration amplifier is 60 to 900 nucleotides in length.

17. The method of claim 1, wherein the collaboration amplifier comprises a spacer between the first, second and/or third segments, wherein the spacer between the first, second and/or third segments is independently 1 to 10 nucleotides in length.

18. The method of claim 1, wherein the third segment of the collaboration amplifier comprises a spacer between the plurality of label amplifier anchor segments, wherein the spacer is independently 1 to 10 nucleotides in length.

19. The method of claim 1, wherein the plurality of collaboration amplifiers bound to the single nucleotide variation probe pre-amplifier and neighbor probe pre-amplifier is in the range of 2 to 20.

20. The method of claim 1, wherein the plurality of label amplifiers bound to the collaboration amplifier is in the range of 2 to 20.

21. The method of claim 1, wherein the plurality of label probes bound to the label amplifier is in the range of 2 to 20.

* * * * *

SEQUENCE LISTING

```
<160> NUMBER OF SEQ ID NOS: 2

<210> SEQ ID NO 1
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: bridged nucleic acids

<400> SEQUENCE: 1
gagatttcac tgtagc                                                  16

<210> SEQ ID NO 2
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: bridged nucleic acids

<400> SEQUENCE: 2
gagatttctc tgtagc                                                  16
```